United States Patent
Nakade et al.

(10) Patent No.: US 7,300,917 B2
(45) Date of Patent: *Nov. 27, 2007

(54) REMEDY FOR CHRONIC DISEASE

(75) Inventors: Shinji Nakade, Mishima-gun (JP); Hiromu Habashita, Mishima-gun (JP); Takuya Seko, Osaka (JP)

(73) Assignee: Ono Pharmaceuticals Co., Ltd., Osaka (JP)

( * ) Notice: Subject to any disclaimer, the term of this patent is extended or adjusted under 35 U.S.C. 154(b) by 35 days.

This patent is subject to a terminal disclaimer.

(21) Appl. No.: 10/519,106

(22) PCT Filed: May 28, 2003

(86) PCT No.: PCT/JP03/06679

§ 371 (c)(1),
(2), (4) Date: Dec. 23, 2004

(87) PCT Pub. No.: WO2004/002530

PCT Pub. Date: Jan. 8, 2004

(65) Prior Publication Data

US 2006/0135577 A1   Jun. 22, 2006

(30) Foreign Application Priority Data

Jun. 26, 2002   (JP) .............................. 2002-185542

(51) Int. Cl.
*A61K 38/00*   (2006.01)
*C12P 13/06*   (2006.01)

(52) U.S. Cl. .......................................... 514/2; 435/106
(58) Field of Classification Search ...................... None
See application file for complete search history.

(56) References Cited

U.S. PATENT DOCUMENTS

| | | | |
|---|---|---|---|
| 2004/0067908 A1* | 4/2004 | Nakade et al. ............... | 514/54 |
| 2004/0167132 A1* | 8/2004 | Shankar et al. ............. | 514/241 |
| 2004/0171582 A1* | 9/2004 | Nakade et al. ............... | 514/54 |
| 2004/0224941 A1* | 11/2004 | Seko et al. ............ | 514/217.04 |
| 2005/0256160 A1* | 11/2005 | Habashita et al. .......... | 514/317 |
| 2006/0148830 A1* | 7/2006 | Terakado et al. ......... | 514/264.1 |

FOREIGN PATENT DOCUMENTS

| | | |
|---|---|---|
| WO | WO 01/60819 A1 | 8/2001 |
| WO | WO 01/71022 A2 | 9/2001 |
| WO | WO 03/101978 | * 12/2003 |

OTHER PUBLICATIONS

Contos et al. "Lysophosphatidic Acid Receptors," Mol. Pharm., 2000, 58, 1188-96.*
Pages et al. "Endothelial differentiation gene-2 receptor is involved in lysophosphatidic acid-dependent control of 3T3F442A preadipocyte proliferation and spreading," J. Biol. Chem., 2001, 276, 11599-05.*
Adolfsson et al. "Lysophosphatidic acid stimulates proliferation of cultured smooth muscle cells from human BPH tissue: sildenafil and papaverin generate inhibition," Prost., 2002, 51, 50-8.*
Vacherot et al., "Induction of apoptosis and inhibition of cell proliferation by the lipido-sterolic extract of Serenoa repens (LSESr, Permixon in benign prostatic hyperplasia," Prost., 2000, 45, 259-66.*
Dixon "Weight loss medications," Austr. Fam. Phys., 2006, 35, 576-9.*
Rindfleisch et al. "Diagnosis and management of rheumatoid arthritis.," Am. Fam. Phys., 2005, 72, 1037-47.*
Parada-Turska et al. "Effect of glutamate receptor antagonists and antirheumatic drugs on proliferation of synoviocytes in vitro," Eur. J. Pharm., 2006, 535, 95-7.*
Svetlov, S. I. et al ., EDG receptors and hepatic pathophysiology of LPA and SIP : EDG-ology of liver injury , Biochim . Biophys . Acta . , May 23, 2002, 1582 (1-3) : 251-6. , ISSN : 0006-3002.
International Search Report for PCT/JP03/06679 dated Jul. 29, 2003.

* cited by examiner

*Primary Examiner*—Cecilia J. Tsang
*Assistant Examiner*—Christina M. Bradley
(74) *Attorney, Agent, or Firm*—Sughrue Mion Pllc.

(57) ABSTRACT

A remedy and/or a preventive for a chronic disease which contains an EDG-2 antagonist. Because of binding to a subtype EDG-2 of LPA receptor, an EDG-2 antagonist is useful in treating and/or preventing chronic diseases (for example, diseases caused by the progress of chronic asthma, glomerular nephritis, obesity, arteriosclerosis, rheumatoid and atopic diseases) induced and made chronic by tissue cells whose proliferation is accelerated by LPA mediated by EDG-2.

6 Claims, 6 Drawing Sheets

REMEDY FOR CHRONIC DISEASE

TECHNICAL FIELD

The present invention relates to a remedy and/or a preventive for a chronic disease comprising an EDG (Endothelial differentiation gene)-2 antagonist. More specifically, the present invention relates to a remedy and/or a preventive for a chronic disease selected from diseases induced by the progress of chronic asthma, glomerular nephritis, obesity, prostate hyperplasia, arteriosclerosis which are induced and made chronic by the sthenia of cell proliferation, rheumatoid, atopic dermatitis, comprising an EDG-2 antagonist.

BACKGROUND ART

It is known that various lipid mediators such as eicosanoid and platelet activating factor (PAF) are produced by the activity of phospholipase from cell membranes.

Lysophosphatidic acid of formula

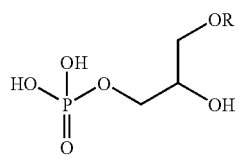

(wherein R is acyl, alkenyl or alkyl) is a lipid which is produced in cell membranes or in blood of living organisms, and it acts as a signal transduction substance and delivers various signals into cells. Among them, L-α-LPA exists naturally And it is also known that R in the formula migrates into the hydroxy group at the 2-position.

Recently, three subtypes of LPA receptors have been identified and it is gradually proved that their various physiological activities are via these LPA receptors. These three subtypes of LPA receptor are called EDG (Endothelial differentiation gene)-2, 4 and 7, and they form EDG receptor family together with EDG-1, 3, 5, 6 and 8 ($S1P_1$, $S1P_3$, $S1P_2$, $S1P_4$, $S1P_5$), which are sphingosine-1-phosphate receptors. EDG-2 is called $LPA_1$ or VZG-1, too (*Mol Pharmacol Dec*; 58(6): 1188-96(2000)). LPA binds to EDG-2, 4 or 7 (LPA receptors) and it transmits a signal into the cells via G-protein coupled to the receptors. Gs, Gi, Gq and $G_{12/13}$, etc. are known as G-proteins which can bind to the LPA receptors, and the varieties are involved with the effect mechanism of LPA. And EDG-2, 4 and 7 are distributed extensively in a body, but since different subtypes have different ways of localization, it is considered that each receptor has different roles depending on the organs. However, the kinds of receptor subtypes localized in each organ are not specified yet.

It is known that LPA is concerned with the proliferation of airway smooth muscle cells, mesangium cells and fat cells [*Am. J. Physiol. Lung Cell Mol. Physiol.* 2002 282(1): L91; *Clin. Science* 1999 96 431; *J. Clin. Invest*.1998 101 1431; *Am. J. Physiol.* (267 Cell Physiol. 36): C204, 1994]. It is also known that LPA is concerned with the activation of dendritic cells (*J Immunol* 2002 Oct. 15; 169(8), 4129). However, it was not revealed via which subtype of LPA receptors these effects were evoked.

In the specification of WO 01/60819, it is disclosed that a compound having an antagonistic activity against the LPA receptor inhibits the proliferation of brain tumor cells and ovarian cancer cells. However, the specification discloses only the experiment of inhibition of proliferation using cancer cells. In cancer cells, innate phenotype of differentiated cells is lost and cancer cells repeat multiplication permanently. A cultured cell line derived from normal organs has different properties from cancer cells. Therefore, the same result is not expected in the cultured cell line derived from normal organs as the result of inhibition of proliferation of cancer cells, and so these results are not to be associated easily and directly.

DISCLOSURE OF THE INVENTION

The present inventors have energetically investigated on the cells which is concerned with LPA except airway smooth muscle cells, mesangium cells and fat cells, so that the present inventors have found that LPA promotes the proliferation of precursor fat cells, prostate stroma cells, coronary artery smooth muscle cells, synovial cells, dendritic cells, etc.

It was not revealed at all via which LPA receptor subtype the proliferation of airway smooth muscle cells, mesangium cells and fat cells was promoted, which had been known to be concerned with LPA, nor the above cells with which the relationship of LPA was revealed now.

The present inventors have energetically investigated to find via which subtype of LPA receptors LPA has effect on the above tissue culture cell line, so that the present inventors have found that it was EDG-2. The present inventors have demonstrated that for the first time that these promotions of cell proliferation were carried out via EDG-2 among the LPA receptor subtypes. These facts are not to be anticipated from prior arts at all and it was confirmed by the present inventors for the first time. From this, it is conceivable that the EDG-2 antagonist is effective for the diseases which are induced and made chronic by the sthenia of cell proliferation as a result of transmission of LPA effect to tissue cells via EDG-2. The present inventors have found that the EDG-2 antagonist is effective for the treatment and/or prevention of chronic diseases, i.e. the diseases induced by the progress of chronic asthma, glomerular nephritis, obesity, prostate hypertrophy, arteriosclerosis, or rheumatoid or atopic dermatitis, etc.

The present invention relates to 1. a remedy and/or a preventive of a chronic disease comprising an EDG-2 antagonist, 2. the remedy and/or the preventive according to the above 1, wherein the chronic disease is chronic asthma, glomerular nephritis, obesity, prostate hyperplasia, a disease induced by the progress of arteriosclerosis, rheumatoid or atopic dermatitis, 3. the remedy and/or the preventive according to the above 2; wherein the chronic disease is prostate hyperplasia, 4. the remedy and/or the preventive according to the above 1, wherein the EDG-2 antagonist is a β-alanine derivative of formula (I)

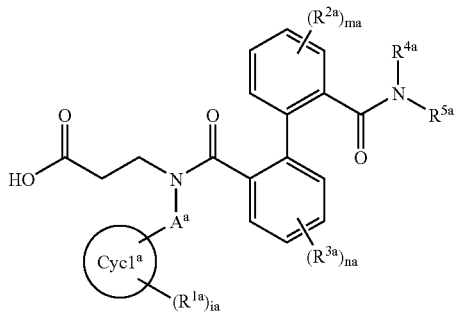

(I)

wherein $A^a$ is, (1) C1-6 alkylene, (2) C2-6 alkenylene, or (3) C2-6 alkynylene (wherein $A_a$ may be substituted with 1-3 of C1-4 alkyl.), $Cyc1^a$ is, (1) C3-15 carboring, or (2) 3-15 membered heteroring having 1-4 of nitrogen, 1-2 of oxygen and/or 1-2 of sulfur, $R^{1a}$ is (1) C1-4 alkyl, (2) halogen, (3) cyano, (4) trihalomethyl, (5) —$OR^{6a}$, (6) —$SR^{7a}$, (7) —$NR^{8a}R^{9a}$, (8) nitro, (9) —$COOR^{10a}$, (10) —$CONR^{11a}R^{12a}$, (11) —$NR^{13a}COR^{14a}$, (12) —$SO_2NR^{15a}R^{16a}$, (13) —$NR^{17a}SO_2R^{18a}$, (14) —$S(O)R^{19a}$, or (15) —$SO_2R^{20a}$, $R^{6a}$, $R^{7a}$, $R^{8a}$, $R^{9a}$, $R^{10a}$, $R^{11a}$, $R^{12a}$, $R^{13a}$, $R^{14a}$, $R^{15a}$, $R^{16a}$, $R^{17a}$, $R^{18a}$, $R^{19a}$ and $R^{20a}$ are each independently, (1) hydrogen, or (2) C1-4 alkyl, $R^{2a}$ and $R^{3a}$ are each independently, (1) C1-4 alkyl, (2) C1-4 alkoxy, or (3) halogen, $R^{4a}$ and $R^{5a}$ are each independently, (1) hydrogen, (2) C1-4 alkyl, (3) C2-4 alkenyl, (4) C2-4 alkynyl, (5) C1-4 alkyl substituted with —$OR^{21a}$, (6) C1-4 alkyl substituted with —$NR^{22a}R^{23a}$ or

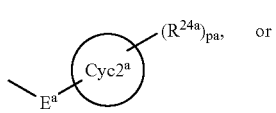

(7)

$R^{4a}$ and $R^{5a}$ are taken together with the nitrogen to which they are attached to form a 3-15 membered mono-, bi- or tri-cyclic heteroring (wherein the heteroring includes at least one nitrogen and it may be substituted with C1-4 alkyl substituted with —$OR^{25a}$.), $R^{21a}$, $R^{22a}$, $R^{23a}$ and $R^{25a}$ are each independently, (1) hydrogen, (2) C1-4 alkyl, (3) C2-6 acyl, or (4) trihaloacetyl, $E^a$ is (1) a bond, (2) C1-6 alkylene, (3) C2-6 alkenylene, or (4) C2-6 alkynylene (wherein $E^a$ may be substituted with 1-3 of (1) C1-4alkyl, or (2) C1-4 alkyl substituted with —$OR^{26a}$.), $R^{26a}$ is (1) hydrogen, (2) C1-4 alkyl, (3) C2-6 acyl, or (4) trihaloacetyl, $Cyc2^a$ is (1) C3-15 carboring, or (2) 3-15 membered heteroring having 1-4 of nitrogen, 1-2 of oxygen and/or 1-2 of sulfur, $R^{24a}$ is (1) C1-4 alkyl, (2) halogen, (3) cyano, (4) trihalomethyl, (5) —$OR^{27a}$, (6) —$SR^{28a}$, (7) —$NR^{29a}R^{30a}$, (8) nitro, (9) —$COOR^{31a}$, (10) —$CONR^{32a}R^{33a}$, (11) —$NR^{34a}COR^{35a}$, (12) —$SO_2NR^{36a}R^{37a}$, (13) —$NR^{38a}SO_2R^{39a}$, (14) —$S(O)R^{40a}$, or (15) —$SO_2R^{41a}$, $R^{27a}$, $R^{28a}$, $R^{29a}$, $R^{30a}$, $R^{31a}$, $R^{32a}$, $R^{33a}$, $R^{34a}$, $R^{35a}$, $R^{36a}$, $R^{37a}$, $R^{38a}$, $R^{39a}$, $R^{40a}$ and $R^{41a}$ are each independently (1) hydrogen, or (2) C1-4 alkyl, ia is 0 or an integer of 1 to 5, ma is 0 or an integer of 1 to 4, and na is 0 or an integer of 1 to 4, pa is 0 or an integer of 1 to 5, and wherein when ia is 2 or more, $R^{1a}$'s are the same or different, when ma is 2 or more, $R^{2a}$'s are the same or different, when na is 2 or more, $R^{3a}$'s are the same or different, and when pa is 2 or more, they are the same or different, or a prodrug thereof or a salt thereof, 5. the remedy and/or the preventive according to the above 1, wherein the EDG-2 antagonist is a compound of formula (II)

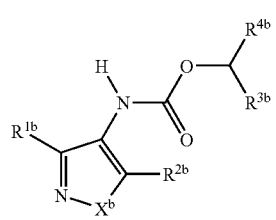

(II)

wherein $R^{1b}$, is C1-20 alkyl optionally having substituent(s), aryl, heteroring, alkyloxy, aryloxy, alkylthio, arylthio, or halogen, $R^{2b}$ is alkyl optionally having substituent(s), aryl, heteroring, alkyloxy, aryloxy or halogen, $R^{3b}$ is hydrogen, lower alkyl or halogenated alkyl, $R^{4b}$ is a group selected from (a) phenyl, aryl or heteroring optionally having substituent(s), (b) substituted or unsubstituted alkyl, and (c) substituted or unsubstituted alkenyl, and $X^b$ is oxygen or sulfur, and wherein $R^{3b}$ and $R^{4b}$ may be taken together with the carbon to which they are attached to form a 5-10 membered ring, and when $R^{3b}$ is hydrogen, $R^{4b}$ is not methyl, or a salt thereof, 6. the remedy and/or the preventive according to the above 1, wherein the EDG-2 antagonist is a compound of formula (III)

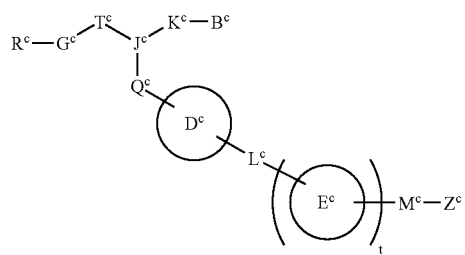

(III)

wherein $R^c$ is optionally substituted aliphatic hydrocarbon or a ring group optionally having substituent(s), $G^c$ is a bond or a spacer having a main chain of 1 to 8 atoms, $T^c$ is —CH$_2$— or a spacer having a main chain of 1 atom having a hydrogen bond—accepting group optionally having substituent(s), $J^c$ is nitrogen or carbon, $B^c$ is optionally substituted aliphatic hydrocarbon or a ring group optionally having substituent(s), $K^c$ is (1) a bond or (2) a spacer having a main chain of 1 to 8 atoms which may form a ring together with the substituent of the ring group represented by $R^c$, ring $D^c$ or the substituent of the ring $D^c$, $Q^c$ is (1) a bond or (2) a spacer having a main chain of 1 to 8 atoms which may form a ring together with the ring group represented by $R^c$, a substituent of the ring group represented by $R^c$, or $K^c$, ring $D^c$ is a ring optionally having more substituent(s), $L^c$ is a bond or a spacer having a main chain of 1 to 3 atoms, ring $E^c$ is, a ring group optionally having substituent(s), $M^c$ is a bond or a spacer having a main chain of 1 to 8 atoms, $Z^c$ is an acidic group, and t is 0 or 1, or a salt thereof, 7. a method for the treatment and/or prevention of a chronic disease characterized by administering to a mammal an effective amount of an EDG-2 antagonist, 8. use of an EDG-2 antagonist for the manufacture of a remedy and/or preventive of a chronic disease, 9. a remedy and/or preventive according to the above 3, comprising an EDG-2 antagonist in combination with one or more selected from LPA receptor antagonist, anti-androgenergic agent, α1 receptor blocker or 5α-reductase inhibitor,

DETAILED DESCRIPTION OF THE PRESENT INVENTION

In the formula (I), C1-4 alkyl is methyl, ethyl, propyl, butyl and isomers thereof.

In the formula (I), C1-8 alkyl is methyl, ethyl, propyl, butyl, pentyl, hexyl, heptyl, octyl and isomers thereof.

In the formula (I), C2-4 alkenyl is ethenyl, propenyl, butenyl and isomers thereof.

In the formula (I), C2-4 alkynyl is ethynyl, propynyl, butynyl and isomers thereof.

In the formula (I), C1-4 alkoxy is methoxy, ethoxy, propoxy, butoxy and isomers thereof.

In the formula (I), C1-6 alkylene is methylene, ethylene, trimethylene, tetramethylene, pentamethylene, hexamethylene and isomers thereof.

In the formula (I), C2-6 alkenylene is ethenylene, propenylene, butenylene, pentenylene, hexenylene and isomers thereof.

In the formula (I), C2-6 alkynylene is ethynylene, propynylene, butynylene, pentynylene, hexynylene and isomers thereof.

In the formula (I), C2-6 acyl is ethanoyl, propanoyl, butanoyl, pentanoyl, hexanoyl and isomers thereof.

In the formula (I), halogen is fluorine, chlorine, bromine and iodine atom.

In the formula (I), trihalomethyl is a methyl group substituted with 3 halogen atoms, e.g. trifluoromethyl, trichloromethyl, tribromomethyl, triiodomethyl.

In the formula (I), trihaloacetyl is acetyl group substituted with 3 halogen atoms, e.g. trifluoroacetyl, trichloroacetyl, tribromoacetyl, triiodoacetyl.

In the formula (I), C3-15 carboring includes, C3-15 mono-, bi- or tri-cyclic unsaturated carboring, partially or completely saturated carboring thereof, spiro bi-cyclic carboring and bridged bi-cyclic carboring, e.g. cyclopropane, cyclobutane, cyclopentane, cyclohexane, cycloheptane, cyclooctane, cyclononane, cyclodecane, cycloundecane, cyclododecane, cyclotridodecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, tetrahydronaphthalene, perhydronaphthalene, heptalene, perhydroheptalene, biphenylene, as-indacene, s-indacene, acenaphthylene, acenaphthene, fluorene, phenalene, phenanthrene, anthracene, spiro[4.4]nonane, spiro[4.5]decane, spiro[5.5]undecane, bicyclo[2.2.1]heptane, bicyclo[2.2.1]hepta-2-ene, bicyclo[3.1.1]heptane, bicyclo[3.1.1]hept-2-ene, bicyclo[2.2.2]octane, bicyclo[2.2.2]octa-2-ene, adamantan, noradamantan, etc.

In the formula (I), 3-15 membered heteroring having 1-4 of nitrogen, 1-2 of oxygen and/or 1-2 of sulfur includes 3-15 membered mono-, bi- or tri-cyclic unsaturated heteroring having 1-4 of nitrogen, 1-2 of oxygen and/or 1-2 of sulfur and partially or completely saturated one thereof, e.g. pyrrole, imidazole, triazole, tetrazole, pyrazole, pyridine, pyrazine, pyrimidine, pyridazine, azepine, diazepine, furan, pyran, oxepin, thiophene, thiopyran, thiepine, oxazole, isoxazole, thiazole, isothiazole, furazane, oxadiazole, oxazine, oxadiazine, oxazepine, oxadiazepine, thiadiazole, thiazine, thiadiazine, thiazepine, thiadiazepine, indole, isoindole, indolidine, benzofuran, isobenzofuran, benzothiophene, isobenzothiophene, dithianaphthalene, indazole, quinoline, isoquinoline, quinolidine, purine, phthalazine, pteridine, naphthyridine, quinoxaline, quinazoline, cinnoline, benzoxazole, benzothiazole, benzimidazole, chromene, benzoxepin, benzoxazepine, benzoxadiazepine, benzothiepine, benzothiazepine, benzothiadiazepine, benzazepine, benzodiazepine, benzofurazane, benzothiadiazole, benzotriazole, carbazole, β-carboline, acridine, phenazine, dibenzofuran, xanthene, dibenzothiophene, phenothiazine, phenoxazine, phenoxathiin, thianthrene, phenantrizine, phenanthroline, perimidine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepin, tetrahydrooxepin, perhydrooxepin, thiirane, thietane, dihydrothiophene, tetrahydrothiophene, dihydrothiopyran, tetrahydrothiopyran, dihydrothiepine, tetrahydrothiepine, perhydrothiepine, dihydroxazole, tetrahydroxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazane, tetrahydrofurazane, dihydrooxadiazole, tetrahydroxadiazole (oxadiazolidine), dihydroxazine, tetrahydroxazine, dihydrooxadiazine, tetrahydrooxadiazine, dihydrooxazepine, tetrahydrooxazepine, perhydrooxazepine, dihydroxadiazepine, tetrahydroxadiazepine, perhydroxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuiran, perhydrodibenzothiophene, dioxolane, dioxane, dithiolane, dithiane, dioxaindan, benzodioxane, chroman, benzodithiolane, benzodithian ring, etc.

In the formula (I), 3-15 membered mono-, bi- or tri-cyclic heteroring which $R^{4a}$ and $R^{5a}$ are taken together with the nitrogen to which they are attached includes, 3-15 membered mono-, bi- or tri-cyclic unsaturated heteroring having at least one nitrogen atom and partially or completely saturated heteroring, e.g. pyrrole, imidazole, triazole, tetrazole, pyrazole, indole, isoindole, indazole, purine, benzimidazole, benzazepine, benzodiazepine, benzotriazole, carbazole, β-carboline, 1,2,3,4-tetrahydro-β-carboline, phenothiazine, phenoxazine, perimidine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, tetrahydroxazole (oxazolidine), tetrahydroisoxazole (isoxazolidine), tetrahydrothiazole (thiazolidine), tetrahydroisothiazole (isothiazolidine), dihydrofurazane, tetrahydrofurazane, dihydrooxadiazole, tetrahydrooxadiazole (oxadiazolidine), dihydrooxazine, dihydrooxadiazine, tetrahydrooxadiazine, perhydrooxazepine, tetrahydrooxadiazepine, perhydrooxadiazepine, dihydrothiadiazole, tetrahydrothiadiazole (thiadiazolidine), tetrahydrothiazine, dihydrothiadiazine, tetrahydrothiadiazine, perhydrothiazepine, tetrahydrothiadiazepine, perhydrothiadiazepine, morpholine, thiomorpholine, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, tetrahydrobenzoxazepine, dihydrocarbazole, tetrahydrocarbazole, perhydrocarbazole, dihydroacridine, perhydroacridine, etc.

In the formula (III), "aliphatic hydrocarbon" in "optionally substituted aliphatic hydrocarbon" represented by $R^C$ includes "straight or branched hydrocarbon", and "straight or branched hydrocarbon" includes "straight or branched alkyl, alkenyl or alkynyl.""Straight or branched alkyl" includes for example, straight or branched C1-10 alkyl, e.g. methyl, ethyl, propyl, isopropyl, butyl, isobutyl, sec-butyl, tert-butyl, pentyl, isopentyl, neopentyl, hexyl, heptyl, octyl, nonyl, decyl, etc. "Straight or branched alkenyl" includes for example, straight or branched C2-10 alkenyl, e.g. ethenyl, propenyl, butenyl, butadienyl, pentenyl, pentadienyl, hexenyl, hexadienyl, heptenyl, heptadienyl, octenyl, octadienyl, nonenyl, nonadienyl, decenyl, decadienyl, etc. "Straight or branched alkynyl" includes, for example, straight or branched C2-10 alkynyl, e.g. ethynyl, propynyl, butynyl, butadiynyl, pentynyl, pentadiynyl, hexynyl, hexadiynyl, heptynyl, heptadiynyl, octynyl, octadiynyl, nonynyl, nonadiynyl, decynyl, decadiynyl, etc.

The "ring group" in the "ring group optionally having substituent(s)" represented by $R^C$ includes for example, carboring or heteroring.

The carboring includes, for example, C3-15 mono-, bi- or tri-cyclic carboring, spiro bi-cyclic carboring or bridged bi-cyclic carboring, etc. C3-15 mono-, bi- or tri-cyclic carboring includes, C3-15 mono-, bi- or tri-cyclic unsaturated carboring, partially or completely saturated one thereof, e.g. cyclopropane, cyclobutane, cyclopentane, cyclohexane, cycloheptane, cyclooctane, cyclononane, cyclodecane, cycloundecane, cyclododecane, cyclotridodecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, tetrahydronaphthalene, perhydronaphthalene, heptalene, perhydroheptalene, biphenylene, as-indacene, s-indacene, acenaphthylene, acenaphthene, fluorene, phenalene, phenanthrene, anthracene, spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[3.2.1]octane, bicyclo[2.2.2]octane, bicyclo[2.2.2]oct-2ene, adamantan, noradamantan, etc. Among them, C3-15 mono-, bi- or tri-cyclic aromatic carboring includes, e.g. benzene, azulene, naphthalene, phenanthrene, anthracene, etc.

The heteroring includes 3-15 membered mono-, bi- or tri-cyclic heteroring, spiro bi-cyclic heteroring or bridged bi-cyclic heteroring, etc. having 1-5 of heteroatom selected from oxygen, nitrogen and sulfur. 3-15 membered mono-, bi- or tri-cyclic heteroring having 1-5 of heteroatom selected from oxygen, nitrogen and sulfur includes, 3-15 membered mono-, bi- or tri-cyclic unsaturated heteroring having 1-5 of heteroatom selected from oxygen, nitrogen and sulfur, partially or completely saturated heteroring thereof, e.g. pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazane, oxadiazole, oxazine, oxadiazine, oxazepin, oxadiazepine, thiadiazole, thiazine, thiadiazine, thiazepine, thiadiazepine, indole, isoindole, indolidine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiaze pine, benzofurazdane, benzothiadiazole, benzotriazole, carbazole, β-carboline, acridine, phenazine, dibenzofuran, xanthene, dibenzothiophene, phenothiazine, phenoxazine, phenoxathiin, thianthrene, phenanthridine, phenanthroline, perimidine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydroxepine, tetrahydrooxepin, perhydroxepine, thiiran, thietan, dihydrothiophene, tetrahydrothiophene, dihydrothiopyran, tetrahydrothiopyran, dihydrothiepine, tetrahydrothiepine, perhydrothiepine, dihydroxazole, tetrahydroxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazane, tetrahydrofurazane, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydroxazepine, perhydrooxazepine, dihydrooxadiazepine, tetrahydroxadiazepine, perhydroxadiazepine, dihydrothiadiazole, tetrahydrothiadiazole (thiadizolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathian, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathian, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepan, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindan, benzodioxane, chroman, benzodithiolane, benzodithiane ring, etc.

The spiro bi-cyclic heteroring includes, e.g. azaspiro[4.4]nonane, azaspiro[4.5]decane, azaspiro[5.5]undecane, etc.

The bridged bi-cyclic heteroring includes, e.g. azabicyclo[2.2.1]heptane, azabicyclo[3.1.1]heptane, azabicyclo[3.2.1]octane, azabicyclo[2.2.2]octane, etc. Among them, 3-15 membered mono-, bi- or tri-cyclic aromatic heteroring having 1-5 of heteroatom selected from oxygen, nitrogen and sulfur includes, e.g. pyrrole, imidazole, triazole, tetrazole, pyrazole, pyridine, pyrazine, pyrimidine, pyridazine, furan, thiophene, oxazole, isoxazole, thiazole, isothiazole, furazane, oxadiazole, thiadiazole, indole, isoindole, benzofuran, isobenzofuran, benzothiophene, isobenzothiophene, indazole, quinoline, isoquinoline, purine, phthalazine, pteridine, naphthyridine, quinoxaline, quinazoline, cinnoline, benzoxazole, benzothiazole, benzoimidazole, benzofurazane, benzothiadiazole, benzotriazole, carbazole, β-carboline, acridine, phenazine, dibenzofuran, dibenzothiophene, phenanthridine, phenanthroline, perimidine ring, etc.

The "substituent" in the, "optionally substituted aliphatic hydrocarbon" or the "ring optionally having substituent(s)" represented by $R^c$, includes for example, (a) optionally substituted alkyl, (b) optionally substituted alkenyl, (c) optionally substituted alkynyl, (d) carboring optionally having substituent(s), (e) heteroring optionally having substituent(s), (f) optionally substituted hydroxy, (g) optionally substituted thiol, (h) optionally substituted amino, (i) optionally substituted carbamoyl, (j) optionally substituted sulfamoyl, (k) carboxy, (l) alkoxycarbonyl (e.g. C1-6 alkoxycarbonyl group such as methoxycarbonyl, ethoxycarbonyl, t-butoxycarbonyl, etc.), (m) sulfo (—$SO_3H$), (n) sulfino, (o) phosphono, (p) nitro, (q) oxo, (r) thioxo, (s) cyano, (t) amidino, (u) imino, (v) —$B(OH)_2$, (w) halogen (e.g. fluorine, chlorine, bromine, iodine), (x) alkylsulfynyl (e.g. C1-6 alkylsulfynyl such as methylsulfynyl, ethylsulfynyl, etc.), (y) arylsulfinyl (e.g. C6-10 arylsulfonyl such as phenylsulfynyl etc.), (z) alkylsulfonyl (e.g. C1-6 alkylsulfonyl such as methylsulfonyl, ethylsulfonyl, etc.), (aa) arylsulfonyl (e.g. C6-10 arylsulfonyl such as phenylsulfonyl etc.), (bb) acyl (e.g. C1-6 alkanoyl such as formyl, acetyl, propanoyl, pivaolyl, etc. and C6-10 arylcarbonyl such as benzoyl etc.), etc. and 1 to 5 groups of these optional substituents may be placed in the acceptable position. As the substituent "alkyl" in the "optionally substituted alkyl" includes, for example, C1-10 alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc. Here the substituent of alkyl includes, hydroxy, amino, carboxy, nitro, mono- or di-C1-6 alkylamino (e.g. methylamino, ethylamino, propylamino, dimethylamino, diethylamino, etc.), C1-6 alkoxy (e.g. methoxy, ethoxy, propoxy, hexyloxy, etc.), C1-6 alkylcarbonyloxy (e.g. acetoxy, ethylcarbonyloxy, etc.), phenyl and halogen (e.g. fluorine, chlorine, bromine, iodine), etc., and 1 to 4 groups of these substituents may be placed in the acceptable position. As the substituent "alkenyl" in the "optionally substituted alkenyl" includes, for example, straight or branched C2-10 alkenyl, etc. such as ethenyl, propenyl, butenyl, butadienyl, pentenyl, pentadienyl, hexenyl, hexadienyl, heptenyl, heptadienyl, octenyl, octadienyl, nonenyl, nonadienyl, decenyl, decadienyl. Here the substituent of alkenyl has the same meaning as the above substituent in the "optionally substituted alkyl". As the substituent "alkenyl" in the "optionally substituted alkynyl" includes, for example, straight or branched C2-10 alkynyl such as ethynyl, propynyl, butynyl, butadiynyl, pentynyl, pentadiynyl, hexynyl, hexadiynyl, heptynyl, heptadiynyl, octynyl, octadiynyl, nonynyl, nonadiynyl, decynyl, decadiynyl. Here the substituent of alkyl has the same meaning as the substituent in the above "optionally substituted alkyl". As the substituent carboring in the "carboring optionally having substituent(s)" has the same meaning as the above carboring in the "ring group" in the "ring group optionally having substituent(s)". Here the substituent of the carboring includes, for example, straight or branched C1-10 alkyl (it has the same meaning as alkyl in the above "optionally substituted alkyl"), straight or branched C2-10 alkenyl (the same meaning as alkenyl in the "optionally substituted alkenyl" described hereinbefore.), straight or branched C2-10 alkynyl (the same meaning as alkynyl in the "optionally substituted alkynyl" described hereinbefore.), hydroxy, C1-6 alkoxy (e.g. methoxy, ethoxy, propoxy, isopropoxy, butoxy, isobutyloxy, tert-butyloxy, pentyloxy, hexyloxy, etc.), thiol, C1-6 alkylthio (e.g. methylthio, ethylthio, propylthio, isopropylthio, butylthio, isobutylthio, tert-butylthio, pentylthio, hexylthio, etc.), amino, mono- or di-C1-6 alkylamino (e.g. methylamino, ethylamino, propylamino, isopropylamino, butylamino, isobutylamino, tert-butylamino, pentylamino, hexylamino, dimethylamino, diethylamino, dipropylamino, N-methyl-N-ethylamino, etc.), halogen (the same meaning as described hereinbefore), cyano, nitro, trifluoromethyl, trifluoromethoxy, etc., and 1-5 groups of these substituents may be placed in the acceptable position. As the substituent, the heteroring in the "heteroring optionally having substituent(s)" has the same meaning as the heteroring in the "ring group" in the "ring group optionally having substituent(s)." Here the substituent of the heteroring has the same meaning as the substituent in the "carboring optionally having substituent(s)" described hereinbefore. As the "substituent" in the "optionally substituted hydroxy", "optionally substituted thiol" and "optionally substituted amino" include, for example, (i) optionally substituted alkyl (the same meaning as described hereinbefore), (ii) optionally substituted alkenyl (the same meaning as described hereinbefore), (iii) optionally substituted alkynyl (the same meaning as described hereinbefore), (iv) carboring optionally having substituent(s) (the same meaning as described hereinbefore), (v) heteroring optionally having substituent(s) (the same meaning as described hereinbefore), (vi) acyl(e.g. C1-6 alkanoyl such as formyl, acetyl, propanoyl, pivaloyl, butanoyl, pentanoyl, hexanoyl, etc. or isomers thereof, e.g. C6-10 aromatic carboring carbonyl such as benzoyl etc.), (vii) optionally substituted carbamoyl (the same meaning as hereafter described.), (viii) alkylsulfonyl (e.g. C1-6 alkylsulfonyl e.g. methylsulfonyl, ethylsulfonyl, etc.), (ix) arylsulfonyl (e.g. C6-10 arylsulfonyl such as phenylsulfonyl etc.). As a substituent "optionally substituted carbamoyl" includes unsubstituted carbamoyl such as N-mono-C1-6 alkylcarbamoyl (e.g. N-mono-C6-10 arylcarbamoyl such as N-methylcarbamoyl, N-ethylcarbamoyl, N-propylcarbamoyl, N-isopropylcarbamoyl, N-butylcarbamoyl, N-isobutylcarbamoyl, N-(tert-butyl)carbamoyl, N-pentylcarbamoyl, N-hexylcarbamoyl, etc.), N-phenylcarbamoyl such as N,N-di-C1-6 alkylcarbamoyl (e.g. N,N-dimethylcarbamoyl, N,N-diethylcarbamoyl, N,N-dipropylcarbamoyl, N,N-dibutylcarbamoyl, N,N-dipentylcarbamoyl, N,N-dihexylcarbamoyl, N-methyl-N-ethylcarbamoyl, etc.), N-di-C6-10 arylcarbamoyl such as N,N-diphenylcarbamoyl, etc., N-C6-10 aryl-N-C1-6 alkylcarbamoyl (e.g. N-phenyl-N-methylcarbamoyl, N-phenyl-N-ethylcarbamotyl, N-phenyl-N-propylcarbamoyl, N-phenyl-N-butylcarbamoyl, N-phenyl-N-pentylcarbamoyl, N-phenyl-N-hexylcarbamoyl, etc.), etc. As the substituent "optionally substituted sulfamoyl" includes unsaturated sulfamoyl, N-mono-C1-6alkylsulfamoyl (e.g. N-methylsulfamoyl, N-ethylsulfamoyl, N-propylsulfamoyl, N-isopropylsulfamoyl, N-butylsulfamoyl, N-isobutylsulfamoyl, N-(tert-butyl)sulfamoyl, N-pentylsulfamoyl, N-hexylsulfamoyl, etc.), N-mono-C6-10 arylsulfamoyl such as N-phenylsulfamoyl, etc., N,N-di-C1-6 alkylsulfamoyl (e.g. N,N-dimethylsulfamoyl, N,N-diethylsulfamoyl, N,N-dipropylsulfamoyl, N,N-dibutylsulfamoyl, N,N-dipentylsulfamoyl, N,N-dihexylsulfamoyl, N-methyl-N-ethylsulfamoyl, etc.), N-di-C6-10 arylsulfamoyl such as N,N-diphenylsulfamoyl, etc., N-C6-10 aryl-N-C1-6alkylsulfamoyl (e.g. N-phenyl-N-methylsulfamoyl, N-phenyl-N-ethylsulfamoyl, N-phenyl-N-propylsulfamoyl, N-phenyl-N-butylsulfamoyl, N-phenyl-N-pentylsulfamoyl, N-phenyl-N-hexylsulfamoyl, etc.), etc.

The "spacer having a main chain of 1 to 8 atoms" represented by $G^c$ means a space in which 1 to 8 atoms are linked. Here, "the number of atoms in the main chain" is counted so that the number of atoms in the main chain is minimum. The "spacer having a main chain of 1 to 8 atoms" represented by $G^c$ includes, for example, C1-8 alkylene optionally having substituent(s) (e.g. methylene, ethylene, trimethylene, tetramethylene, pentamethylene, hexamethylene, heptamethylene, octamethylene, etc.), C2-8 alkenylene optionally having substituent(s) (e.g. ethenylene, propenylene, butenylene, butadienylene, pentenylene, pentadienylene, hexenylene, hexadienylene, heptenylene, heptadienylene, octenylene, octadienylene, etc.), C2-8 alkynylene optionally having substituent(s) (e.g. ethynylene, propynylene, butynylene, butadiynylene, pentynylene, pentadiynylene, hexynylene, hexadiynylene, heptynylene, heptadiynylene, octynylene, octadiynylene, etc.), etc. Here the carbon atom in C1-8 alkylene, C2-8 alkenylene and C2-8 alkynylene may be replaced by, oxygen, optionally oxidized sulfur (e.g. S, SO, $SO_2$, etc.) or optionally substituted nitrogen [As the substituent, (i) optionally substituted alkyl (the same meaning as hereinbefore.), (ii) optionally substituted carboring (the same meaning as hereinbefore.), (iii) optionally substituted heteroring (the same meaning as hereinbefore.), (iv) acyl (the same meaning as hereinbefore.), etc.]. Here the "substituent" in the "C1-8 alkylene optionally having substituent(s)", "C2-8 alkenylene optionally having substituent(s)" and "C2-8 alkynylene optionally having substituent(s)" include, for example, optionally substituted alkyl (the same meaning as hereinbefore.), halogen (e.g. fluorine, chlorine, bromine, iodine), optionally substituted hydroxy (the same meaning as hereinbefore.), optionally substituted amino (the same meaning as hereinbefore.), oxo, optionally substituted imino (e.g. C1-6 alkylimino, hydroxyimino, C1-6 alkoxyimino, cyanoimino, etc.), etc., and 1-3 of these groups may be placed in the acceptable position.

The "hydrogen bond-accepting group" in the "spacer having a main chain of 1 atom having a hydrogen bond-accepting group optionally having substituent(s)" is a group containing an atom having unshared electron pair. The atom means one spacer. Here, the "number of atoms in the main chain" is counted so that the number of atoms in the main chain is minimum. The "spacer having a main chain of 1 atom having a hydrogen bond-accepting group optionally having substituent(s)" includes, for example, carbonyl (e.g. —CO— etc.), thiocarbonyl (e.g. —CS— etc.), optionally substituted imino (the same meaning as hereinbefore.), sulfonyl (e.g. —$SO_2$— etc.), sulfonyl (e.g. —SO— etc.), methylene substituted with hydroxy (e.g. —CHOH— etc.), etc.

The "optionally substituted aliphatic hydrocarbon" represented by $B^c$ has the same meaning as the "optionally substituted aliphatic hydrocarbon" described hereinbefore. The "ring optionally having substituent(s)" has the same meaning as the "ring optionally having substituent(s)" described hereinbefore.

The "spacer having a main chain of 1 to 8 atoms" in the "spacer having a main chain of 1 to 8 atoms which may form a ring together with the ring group represented by $R^c$, ring $D^c$ or the substituent of the ring $D^{C}$" represented by $K^c$ has the same meaning as the "spacer having a main chain of 1 to 8 atoms" as described hereinbefore. The ring which is formed with the substituent of ring represented by $R^c$, ring $D^c$ or the substituent of ring $D^c$ in the "spacer having a main chain of 1 to 8 atoms which may form a ring together with the substituent of the ring represented by $R^c$, ring $D^c$ or the substituent of the ring $D^c$" has the same meaning as the "ring group" described hereinbefore.

The "spacer having a main chain of 1 to 8 atoms" in the "spacer having a main chain of 1 to 8 atoms which may form a ring together with the ring group represented by $R^c$, the substituent of the ring group represented by $R^c$ or $K^c$" has the same meaning as the "spacer having a main chain of 1 to 8 atoms" as described hereinbefore. The ring which forms together with the ring group represented by $R^c$, the substituent of the ring group represented by $R^c$ or $K^c$ in "the spacer having a main chain of 1 to 8 atoms in the ring represented by $R^c$, the substituent of the ring represented by $R^c$ or $K^c$" represented by $Q^c$ has the same meaning as the "ring group" as described hereinbefore.

The "ring optionally having substituent(s)" represented by ring $D^c$ has the same meaning as the "ring optionally having substituent(s)" as described hereinbefore.

The "spacer of 1 to 3 atoms in the main chain" represented by $L^c$ means a space in which 1 to 3 atoms are linked. Here, the "number of atoms in the main chain" is counted so that the number of atoms in the main chain is minimum. The "spacer of 1 to 3 atoms in the main chain" represented by $L^c$ includes, for example, C1-3 alkylene optionally having a substituent (e.g. —CH$_2$-, —(CH$_2$)$_2$-, —(CH$_2$)$_3$-, etc.), —O—, —S—, —SO—, —SO$_2$-, —NR$^{6c}$—, —CONR$^{6c}$—, —NR$^{6c}$CO—, —SO$_2$NR$^{6c}$—, —NR$^{6c}$SO$_2$-, —NR$^{6c}$CONR$^{7c}$— [wherein $R^{6c}$ and $R^{7c}$ are each independently, hydrogen, optionally substituted aliphatic hydrocarbon (the same meaning as hereinbefore.) or ring optionally having substituent(s) (the same meaning as hereinbefore.).], etc. Here the substituent of C1-3 alkylene includes, for example, halogen (e.g. fluorine, chlorine, bromine, iodine), hydroxy, amino, oxo, etc., and 1-3 of these substituents may be placed in the acceptable position.

The "ring group optionally having substituent(s)" represented by ring $E^c$ has the same meaning as the "ring group optionally having substituent(s)" as described hereinbefore.

The "spacer of 1 to 8 atoms in the main chain" represented by $M^c$ has the same meaning as the "spacer of 1 to 8 atoms in the main chain" as described hereinbefore.

The "acidic group" represented by $Z^c$ includes, for example, various kinds of Brönsted acid such as —COOR$^{5c}$ ($R^{5c}$ is hydrogen, optionally substituted aliphatic hydrocarbon or ring group optionally having substituent(s).), sulfo (—SO$_3$H), —SO$_2$NHR$^{5c}$ ($R^{5c}$ has the same meaning as hereinbefore.), —NHSO$_2$R$^{5c}$ ($R^{5c}$ has the same meaning as hereinbefore.), phosphono (—PO(OH)$_2$), phenol (—C$_6$H$_4$OH) or a ring group having nitrogen having a deprotonatable hydrogen atom, etc. "Brönsted acid" shows a substance which gives hydrogen ion to another substance.

The "ring group having nitrogen having a deprotonatable hydrogen" includes

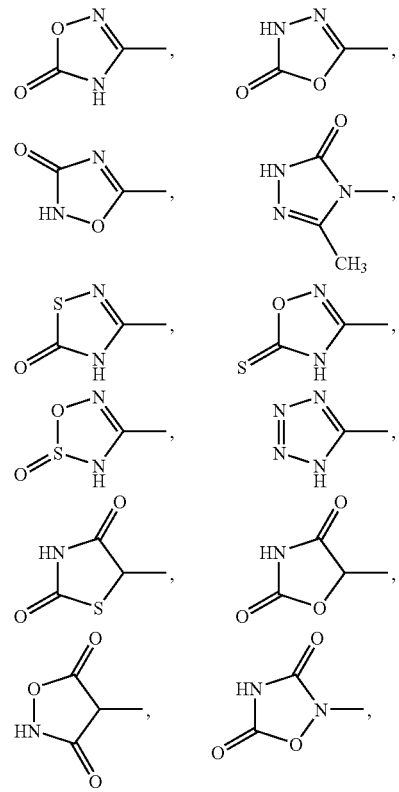

etc.

The "optionally substituted aliphatic hydrocarbon" represented by $R^{5c}$ has the same meaning as the "optionally substituted hydrocarbon" described hereinbefore. The "ring group optionally having substituent(s)" represented by $R^{5c}$ has the same meaning as the "ring group optionally having substituent(s)" described hereinbefore.

In the formula (III), $R^c$ is preferably, e.g. ring group optionally having substituent(s) etc., and more preferably, e.g. C3-15 mono-, bi- or tri-cyclic aromatic carboring optionally having substituent(s), and 3-15 membered mono-, bi- or tri-cyclic aromatic heteroring having 1-5 of hetero atom selected arbitrary from oxygen, nitrogen and sulfur optionally having substituent(s), etc., particularly preferably e.g., cyclopentane optionally having substituent(s), cyclopentene optionally having substituent(s), benzene optionally having substituent(s), naphthalene optionally having substituent(s), furan optionally having substituent(s), isoxazole optionally having substituent(s), thiophene optionally having substituent(s), 1,2,3-thiadiazole optionally having substituent(s), pyrrole optionally having substituent(s), pyrazole optionally having substituent(s), benzothiophene optionally having substituent(s), indole optionally having substituent(s), 1,3-dioxaindan optionally having substituent(s), pyridine optionally having substituent(s), cinnoline optionally having substituent(s), etc.

Moreover, the ring group optionally having substituent(s) is preferably, for example, C3-15 mono-, bi- or tri-cyclic aromatic carboring optionally having a substituent, 3-15 membered mono-, bi- or tri-cyclic aromatic heteroring having 1-5 of hetero atom selected from oxygen, nitrogen and sulfur optionally having substituent(s), etc., most preferably, for example, C5-6 monocyclic aromatic carboring optionally having substituent(s), 5-6 membered mono-, bi- or tri-cyclic aromatic heteroring having 1-5 of hetero atom selected from oxygen, nitrogen and sulfur optionally having substituent(s), etc., particularly preferably, for example, benzene optionally having substituent(s), pyridine optionally having substituent(s), etc. Here the substituent is preferably, optionally substituted alkyl, carboring optionally having substituent(s), heteroring optionally having substituent(s), optionally substituted hydroxy, optionally substituted thiol, optionally substituted amino, optionally substituted sulfamoyl, carboxy, nitro, halogen, alkylsulfonyl, acyl, etc., more preferably, for example, optionally substituted alkyl, optionally substituted hydroxy, halogen, etc., most preferably, methyl, fluorine, chlorine, methoxy, ethoxy, difluoromethoxy, hydroxy, etc. 1-5 of these substituents may be placed in the acceptable position and 0 or 1-3 of substituents is preferable.

$G^c$ is preferably, for example, a bond, C1-8 alkylene optionally having substituent(s), C2-8 alkenylene optionally having substituent(s), etc., more preferably, a bond, a spacer having a main chain of 1 to 4 atoms (e.g. C1-4 alkylene optionally having substituent(s), C2-4 alkenylene optionally having substituent(s), etc.), etc. particularly preferably, a bond, methylene optionally having substituent(s), ethylene optionally having substituent(s), ethenylene optionally having substituent(s), etc., the carbon atom thereof may be replaced by oxygen, optionally oxidized sulfur (e.g. S, SO, $SO_2$, etc.) or optionally substituted nitrogen, preferably, e.g. optionally substituted nitrogen, etc., more preferably, e.g. —NH— etc. The substituent in $G^c$ is preferably, e.g. optionally substituted alkyl, halogen, optionally substituted hydroxy, oxo, etc., more preferably, e.g. methyl, ethyl, fluorine, methoxy, oxo. 1-3 of the optional substituents may be placed in the acceptable position, preferably e.g. 1-2 of substituents, etc., above all preferable $G^c$ is, e.g. a bond etc.

$T^c$ is preferably, e.g. —CO—, —CS—, optionally substituted imino, —$SO_2$—, —SO—, —CHOH—, etc., and more preferably e.g. —CHOH—, —CO—, etc.

$J^c$ is preferably e.g. nitrogen or carbon.

$K^c$ is preferebly, e.g. a bond, C1-8 alkylene optionally having substituent(s), C2-8 alkenylene optionally having substituent(s), etc., more preferably, e.g. a bond, a spacer having a main chain of 1 to 4 atoms (e.g. C1-4 alkylene optionally having substituent(s), C2-4 alkenylene optionally having substituent(s), etc.), etc., particularly preferably, e.g. a bond, methylene, ethylene, trimethylene, tetramethylene, ethenylene, propenylene, etc. Here the carbon atom may be replaced by oxygen, optionally oxidized sulfur (e.g. S, SO, $SO_2$, etc.) or optionally substituted nitrogen, more preferably, oxygen, optionally oxidized sulfur (e.g. S, SO, $SO_2$, etc.), etc., more preferably, e.g. oxygen or sulfur, etc. The substituent in $K^c$ is preferably, e.g., optionally substituted alkyl, halogen, optionally substituted hydroxy, oxo, etc., more preferably, e.g. methyl, fluorine, hydroxy, oxo. 1-3 of these substituents may be placed in the acceptable position, and 1 or 2 substituents are preferable. Particularly preferable $K^c$ is, for example, trimethylene, 1,1-difluorotrimethylene, etc.

$B^c$ is preferably, e.g. optionally substituted C1-6 alkyl or C3-15 mono-, bi- or tri-cyclic carboring optionally having substituent(s), 3-15 membered mono-, bi- or tricyclic heteroring having 1-5 of hetero atom arbitrary selected from oxygen, nitrogen and sulfur optionally having substituent(s), etc., more preferably, optionally substituted propyl, cyclohexane optionally having substituent(s), benzene optionally having substituent(s), indan optionally having substituent(s), tetrahydronaphthalene optionally having substituent(s), naphthalene optionally having substituent(s), pyrrolidine optionally having substituent(s), piperidine optionally having substituent(s), piperazine optionally having substituent(s), morpholine optionally having substituent(s), pyridine optionally having substituent(s), thiazole optionally having substituent(s), imidazole optionally having substituent(s), indole optionally having substituent(s), thiophene optionally having substituent(s), etc. Moreover, preferable $B^c$ is, for example, C3-15 mono-, bi- or tri-cyclic aromatic carboring optionally having substituent(s), 3-15 membered mono-, bi- or tri-cyclic aromatic heteroring having 1-5 of hetero atom arbitrary selected from oxygen, nitrogen and sulfur optionally having substituent(s), etc., particularly preferably, e.g. C5-6 monocyclic carboring, 5-6 membered monocyclic aromatic heteroring having 1-5 of heteroatom selected from oxygen, nitrogen and sulfur optionally having substituent(s), most preferably, e.g. benzene optionally having substituent(s), thiophene optionally having substituent(s), etc. Here preferable substituent is, optionally substituted alkyl, carboring optionally having substituent(s), optionally substituted hydroxy, nitro, halogen, oxo, etc., more preferably, e.g. optionally substituted alkyl, halogen, etc., most preferably, methyl, fluorine, chlorine, etc. 1-5 of these substituents may be placed in the acceptable position and 0 or 1-2 substituents are preferable.

$Q^c$ is preferably, e.g. a bond, C1-8 alkylene optionally having substituent(s) or C2-8 alkenylene optionally having substituent(s), etc., more preferably, for example, a bond, a spacer having a main chain of 1 to 4 atoms (e.g. C1-4 alkylene optionally having substituent(s), C2-4 alkenylene optionally having substituent(s), etc.), etc., particularly preferably, for example, a bond, methylene, ethylene, trimethylene, tetramethylene, etc., here the carbon atom may be replaced by oxygen, optionally oxidized sulfur (e.g. S, SO, $SO_2$, etc.) or optionally substituted nitrogen, preferably, for example, oxygen or sulfur, etc. The substituent of $Q^c$ is preferably, for example, optionally substituted alkyl, more preferably, for example, methyl. 1-3 of these arbitrary substituents may be placed in the acceptable position, preferably one substituent. Particularly preferable $Q^c$ is for example, methylene etc.

Ring $D^c$ is preferably, for example, C3-15 mono-, bi- or tri-cyclic aromatic carboring optionally having substituent(s), 3-15 membered mono-, bi- or tri-cyclic aromatic heteroring having 1-5 of hetero atom selected from oxygen, nitrogen and sulfur optionally having substituent(s), etc., more preferably, for example, benzene optionally having substituent(s), cyclohexane optionally having substituent(s), piperidine optionally having substituent(s), pyrrole optionally having substituent(s), pyrazole optionally having substituent(s), pyridine optionally having substituent(s), 1,3,4-oxadiazole optionally having substituent(s), thiazole optionally having substituent(s), dihydrobenzoxazine, indole optionally having substituent(s), etc. $D^c$ is more preferably, e.g. C3-15 mono-, bi- or tri-cyclic aromatic carboring optionally having substituent(s), 3-15 membered mono-, bi- or tri-cyclic aromatic heteroring having 1-5 of hetero atom selected from oxygen, nitrogen and sulfur optionally having substituent(s), etc., particularly preferably, for example, benzene optionally having substituent(s), pyrrole optionally having substituent(s), indole optionally having substituent(s), etc. Here the substituent is preferably optionally substituted alkyl, optionally substituted hydroxy, carboxy, halogen, etc., more preferably, for example, optionally substituted alkyl, halogen, etc., most preferably, methyl, fluorine, chlorine, etc. 1-5 of these substituents may be placed in the acceptable position, 0 or 1 substituent is preferable.

$L^c$ is preferably, e.g. a bond, —CH$_2$—, —O—, —S—, —SO—, —SO$_2$— or —NH—, etc., more preferably, a bond, —O—, —S—.

$E^c$ is preferably, e.g. C3-15 mono-, bi- or tri-cyclic aromatic carboring optionally having substituent(s), and 3-15 membered mono-, bi- or tri-cyclic aromatic heteroring having 1-5 of hetero atom selected from oxygen, nitrogen optionally having substituent(s), etc., more preferably, e.g. benzene optionally having substituent(s), piperidine optionally having substituent(s), isoxazole optionally having substituent(s), pyrazole optionally having substituent(s), pyridine optionally having substituent(s), thiazole optionally having substituent(s), imidazole optionally having substituent(s), thiophene optionally having substituent(s), pyrrole optionally having substituent(s), pyrrolidine optionally having substituent(s), etc. More preferable ring $E^c$ is, e.g. C3-15 mono-, bi- or tri-cyclic aromatic carboring optionally having substituent(s), 3-15 membered mono-, bi- or tri-cyclic aromatic heteroring having 1-5 of hetero atom selected from oxygen, nitrogen and sulfur optionally having substituent(s), etc. and particularly preferably, for example, C5-6 monocyclic aromatic carboring optionally having substituent(s), mono-, bi- or tri-cyclic aromatic heteroring comprising 1-5 of heteroatom selected from oxygen, nitrogen and sulfur optionally having substituent(s), etc., most preferably, for example, benzene optionally having substituent(s), etc. Here as the substituent, preferably, optionally substituted alkyl, optionally substituted hydroxy, halogen, etc., more preferably, for example, methyl, chlorine, fluorine, methoxy, ethoxy, etc. 1-5 of these substituents may be placed in the acceptable position, and 0 or 1 substituent is preferable.

t is preferably 0 or 1.

$M^c$ is preferably, for example, a bond, C1-8 alkylene optionally having substituent(s) or C2-8 alkenylene optionally having substituent(s), etc., more preferably, for example, a bond, a spacer having a main chain of 1 to 4 atoms (e.g. C1-4 alkylene optionally having substituent(s), C2-4 alkenylene optionally having substituent(s), etc.), etc., particularly preferably, for example, a bond, methylene, ethylene, trimethylene, etc., the substituent in $M^c$ is preferably, for example, optionally substituted alkyl, more preferably, for example, methyl. 1-3 of these substituents may be placed in the acceptable position, and 1-2 substituents are preferable. Above all, $M^c$ is preferably, for example, a bond or methylene, etc.

$Z^c$ is preferably, for example, —COOR$^{5c}$ or tetrazole, etc.

$R^{5c}$ is preferably, for example, hydrogen or C1-8 alkyl, etc., more preferably, e.g. hydrogen or C1-4 alkyl etc., particularly preferably, e.g. hydrogen, methyl or ethyl, etc.

The ring which $K^c$ forms with the substituent of $R^c$ is ring group, and preferably, for example, a compound of formula (III-J)

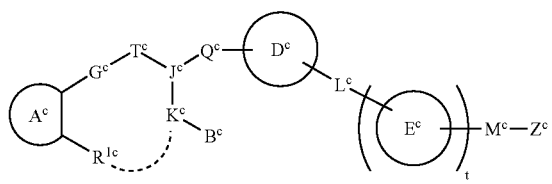

(wherein ring $A^c$ is a ring group optionally having substituent(s) in $R^c$, $R^{1c}$ is the substituent of the ring group in $R^c$, and the other symbols have the same meaning as hereinbefore.), etc., more preferably, for example, the compound of formula (III-J-1)

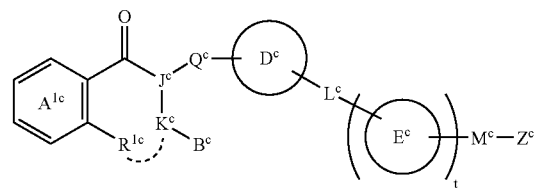

(wherein ring $A^{1c}$ has the same meaning as ring $A^c$, with the proviso that it represents a benzene optionally having substituent(s), and the other symbols have the same meaning as hereinbefore.), etc., particularly preferably, for example, the compound of formula (III-J-1-1)

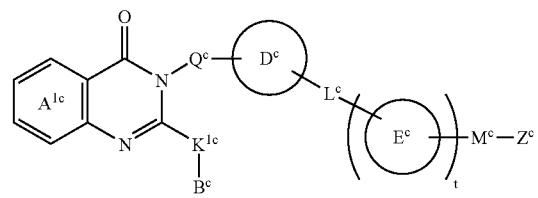

($K^{1c}$ has the same meaning as $K_c$, with the proviso that it represents a spacer having a main chain of 1 to 7 atoms, and the other symbols have the same meaning as hereinbefore.), etc.

The ring which $K^c$ forms together with the ring $D^c$ or the substituent of ring $D^c$ is a ring group, preferably, e.g. a compound selected from the formula (III-K) or (III-N)

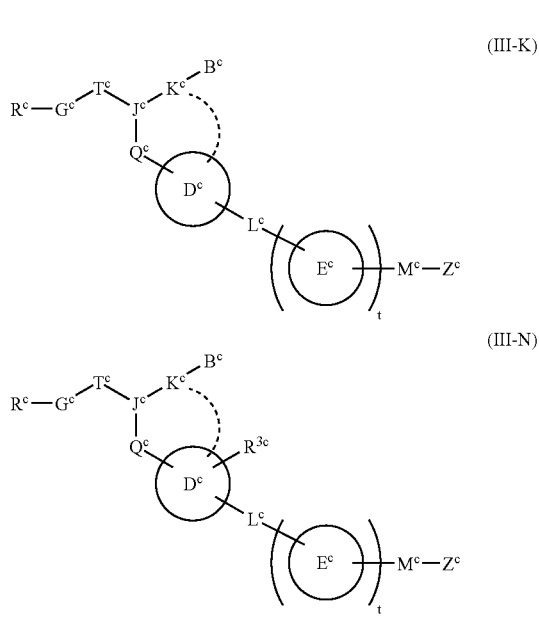

(III-K)

(III-N)

(wherein all symbols have the same meaning as described hereinbefore.), etc., more preferably, the compound selected from the formula (III-K-1) or (III-N-1)

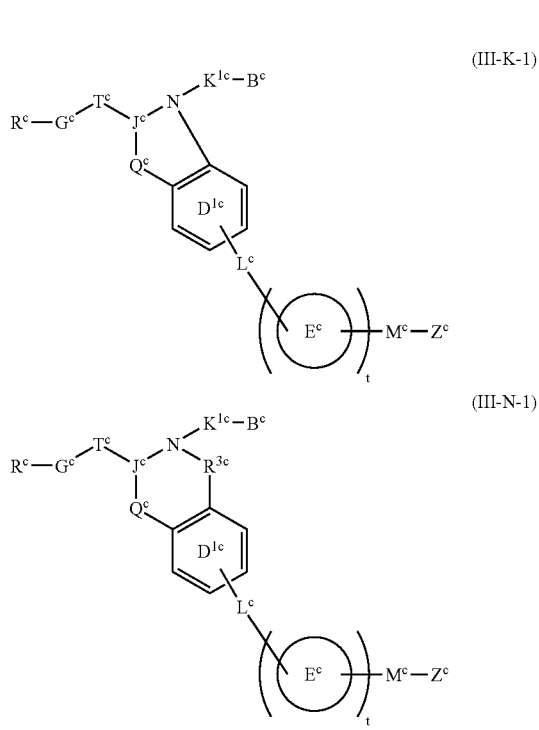

(III-K-1)

(III-N-1)

(wherein ring $D^{1c}$ has the same meaning as ring $D^c$, with the proviso that it represents benzene optionally having substituent(s), $R^{3c}$ represents a substituent of ring $D^c$ and the other symbols have the same meaning as hereinbefore.), etc., particularly preferably, for example, the compound selected from the following formula (III-K-1-1), (III-K-1-2) or (III-N-1-1)

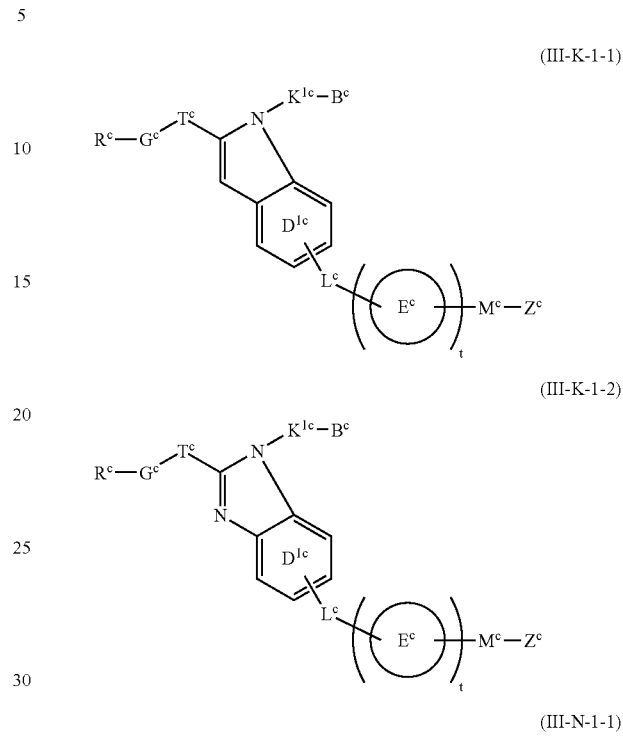

(III-K-1-1)

(III-K-1-2)

(III-N-1-1)

(wherein all symbols have the same meaning as described hereinbefore.), etc.

The ring which $Q^c$ forms with the ring represented by $R^c$ or the substituent of ring group represented by $R^c$, represented by $Q^c$ is a ring group, preferably, for example, a compound of formula (III-L) or (III-O)

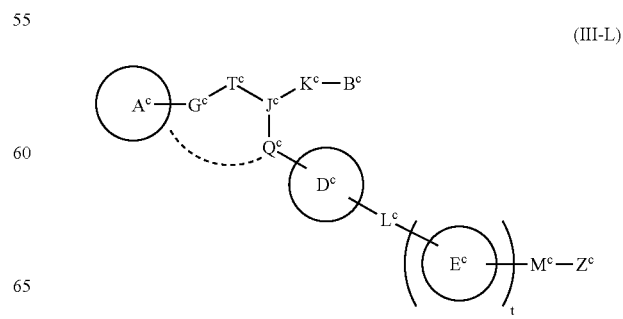

(III-L)

(III-O)

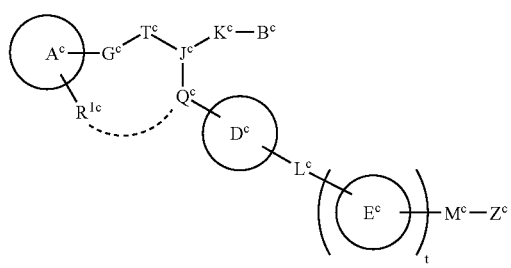

(wherein all symbols have the same meaning as described hereinbefore.), etc., more preferably a compound of formula (III-L-1) or (III-O-1)

(III-L-1)

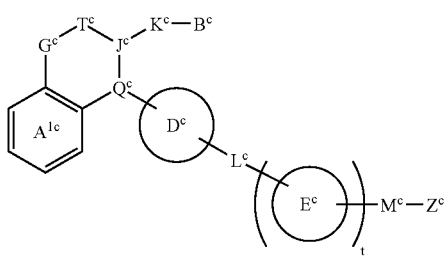

(III-O-1)

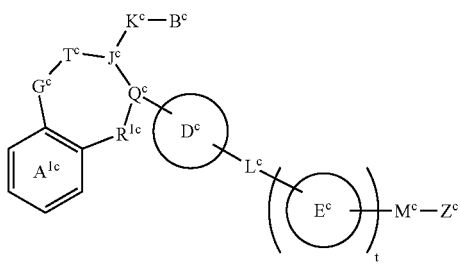

(wherein all symbols have the same meaning as described hereinbefore.), etc., particularly preferably, for example, the compounds described in the following formula (III-L-1-1), (III-O-1-1), (III-O-1-2), (III-O-1-3), (III-O-1-4) or (III-O-1-5)

(III-L-1-1)

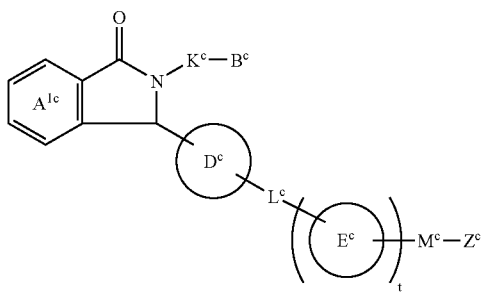

(III-O-1-1)

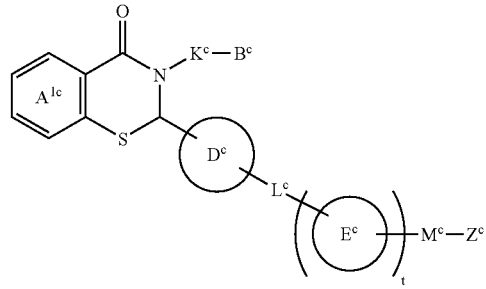

(III-O-1-2)

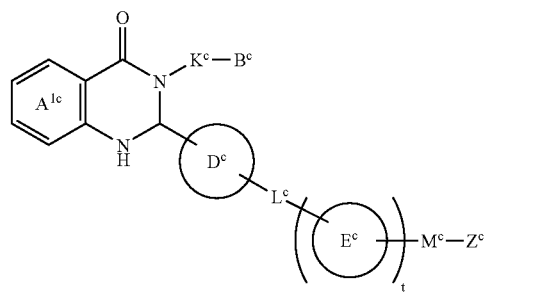

(III-O-1-3)

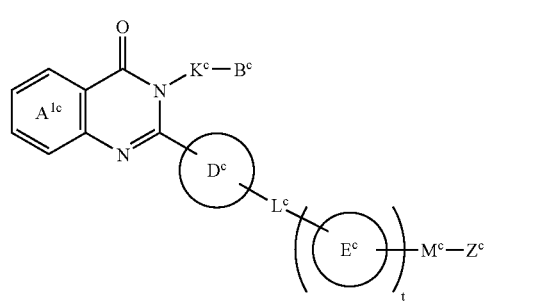

(III-O-1-4)

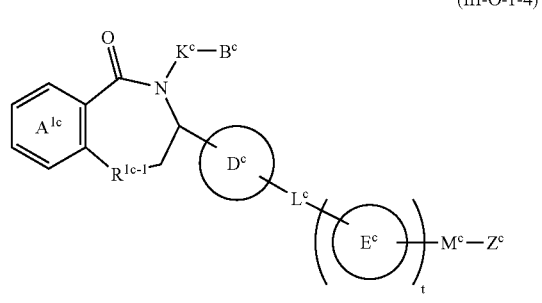

(III-O-1-5)

(wherein, $R^{1c-1}$ is $-CH_{2}-$, $-O-$, $-S-$, $-NH-$, and the other symbols have the same meaning as hereinbefore.), etc.

The ring which $Q^c$ forms together with $K^c$ is ring, and preferably, for example, a compound of formula (III-M)

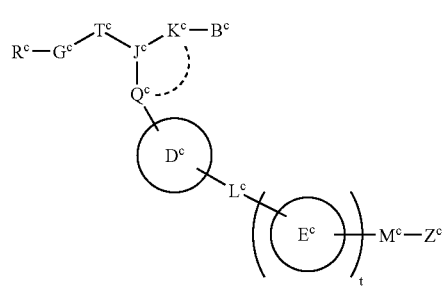

(III-M)

(wherein all symbols have the same meaning as described hereinbefore.), etc., and more preferably, for example, a compound of formula (III-M-1)

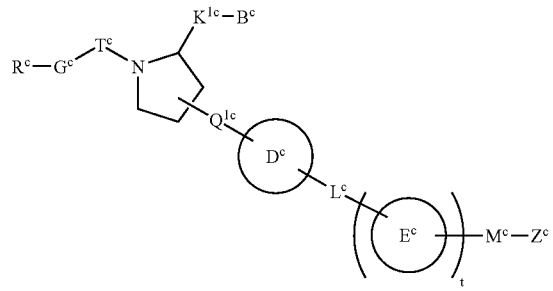

(III-M-1)

($Q^{1c}$ has the same meaning as $Q^c$, with the proviso that it represents a spacer having a main chain of 1 to 7 atoms and the other symbols have the same meaning as hereinbefore.) etc., and particularly preferably, a compound selected from the following formula. (III-M-1-1), (III-M-1-2) or (III-M-1-3)

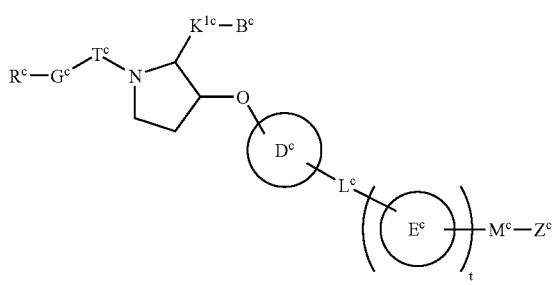

(III-M-1-1)

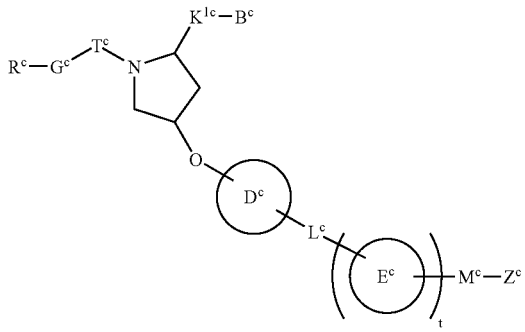

(III-M-1-2)

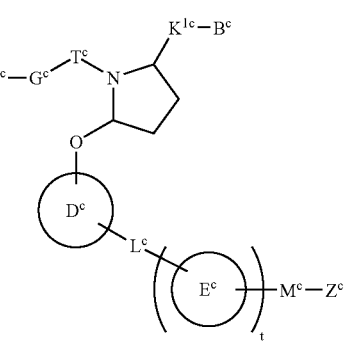

(III-M-1-3)

(all symbols have the same meaning as hereinbefore.), etc.

In the present invention, whatever EDG-2 antagonist will be accepted in the present invention that acts on and inactivates EDG-2. For example, the compounds of formula (I), (II) and (III) are preferably used.

The compounds of formula (I), (II) and (III) may be converted into salts by conventional methods. Pharmaceutically acceptable and water-soluble salts are preferable.

In the present invention, preferable salts include, for example, a salt of alkali metals (potassium, sodium, lithium, etc.), a salt of alkaline earth metals (calcium, magnesium, etc.), an ammonium salt (tetramethylammonium salt, tetrabutylammonium salt, etc.), an organic amine salt (triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.), acid addition salt (inorganic acid salt (hydrochloride, hydrobromide, hydroiodide, sulfate, phosphate, nitrate, etc.), organic acid salt (acetate, trifluoroacetate, lactate, tartarate, oxalate, fumarate, maleate, benzoate, citrate, methanesulfonate, ethanesulfonate, benzenesulfonate, toluenesulfonate, isethionate, glucuronate, gluconate, etc.), etc.).

In the present invention, solvates, or solvates of salts of alkali (earth) metals, ammonium salts, organic amine salts, acid addition salts.

The solvates are preferably non-toxic and water soluble ones. Appropriate solvates include, for example, ones of water, alcohol solvents (ethanol, etc.).

In the compound of formula (I) or (III), preferable compounds include, (1) 3-(N-((2-(2-((4-chlorobenzylamino)carbonyl)phenyl)phenyl)carbonyl)-N-(2-(2-methoxyphenyl)ethyl)amino)propanoic acid, (2) 3-(N-((2-(2-((4-chlorobenzylamino)carbonyl)phenyl)phenyl)carbonyl)-N-(2-(2,4-dichlorophenyl)ethyl)amino)propanoic acid, (3) 3-(N-((2-(2-(((1R)-1-(4-methylphenyl)ethylamino)carbonyl)phenyl)phenyl)carbonyl)-N-(2-(2,4-dichlorophenyl)ethyl)amino)propanoic acid, (4) 3-(N-((2-(2-((pyridin-3-ylmethylamino)carbonyl)phenyl)phenyl)carbonyl)-N-(2-(4-ethoxyphenyl)ethyl)amino)propanoic acid, (5) 3-(N-((2-(2-((4-chlorobenzylamino)carbonyl)phenyl)phenyl)carbonyl)-N-(2-(4-ethoxyphenyl)ethyl)amino)propanoic acid, (6) 3-(N-((2-(2-((4-chlorobenzylamino)carbonyl)phenyl)phenyl)carbonyl)-N-(2-(2-methylphenyl)ethyl)amino)propanoic acid, (7) 3-(N-((2-(2-((pyridin-3-ylmethylamino)carbonyl)phenyl)phenyl)carbonyl)-N-(2-(2,5-dimethoxyphenyl)ethyl)amino)propanoic acid, (8) 3-(N-((2-(2-((4-chlorobenzylamino)carbonyl)phenyl)phenyl)carbonyl)-N-(2-(2,5-dimethoxyphenyl)ethyl)amino)propanoic acid, (9) 3-(N-((2(2-((4-methoxybenzylamino)carboxyl)phenyl)phenyl)carbonyl)-N-(2-(2,5-dimethoxyphenyl)ethyl)amino)propanoic acid,

(10) 3-(N-((2-(2-((4-methylbenzylamino)carbonyl)phenyl)phenyl)carbonyl)-N-(2-(2,5-dimethoxyphenyl)ethyl)amino)propanoic acid,

(11) 3-(N-((2-(2-((N-(1-methylethyl)-N-benzylamino)carbonyl)phenyl)phenyl)carbonyl)-N-(2-(2,5-dimethoxyphenyl)ethyl)amino)propanoic acid,

(12) 3-(N-((2-(2-((4-(tert-butyl)benzylamino)carbonyl)phenyl)phenyl)carbonyl)-N-(2-(2,5-dimethoxyphenyl)ethyl)amino)propanoic acid,

(13) 3-(N-((2-(2-((3-fluorobenzylamino)carbonyl)phenyl)phenyl)carbonyl)-N-(2-(2,5-dimethoxyphenyl)ethyl)amino)propanoic acid,

(14) 3-(N-((2-(2-((2-chlorobenzylamino)carbonyl)phenyl)phenyl)carbonyl)-N-(2-(2,5-dimethoxyphenyl)ethyl)amino)propanoic acid,

(15) 3-(N-((2-(2-((4-fluorobenzylamino)carbonyl)phenyl)phenyl)carbonyl)-N-(2-(2,5-dimethoxyphenyl)ethyl)amino)propanoic acid,

(16) 3-(N-((2-(2-((3-chlorobenzylamino)carbonyl)phenyl)phenyl)carbonyl)-N-(2-(2,5-dimethoxyphenyl)ethyl)amino)propanoic acid,

(17) 3-(N-((2-(2-(((1R)-1-(4-methylphenyl)ethylamino)carbonyl)phenyl)phenyl)carbonyl)-N-(2-(2,5-dimethoxyphenyl)ethyl)amino)propanoic acid,

(18) 3-(N-((2-(2-((1-(4-fluorophenyl)ethylamino)carbonyl)phenyl)phenyl)carbonyl)-N-(2-(2,5-dimethoxyphenyl)ethyl)amino)propanoic acid,

(19) 3-(N-((2-(2-((pyridin-3-ylmethylamino)carbonyl)phenyl)phenyl)carbonyl)-N-(2-(3-ethoxy-4-methoxyphenyl)ethyl)amino)propanoic acid,

(20) 3-(N-((2-(2-((pyridin-3-ylmethylamino)carbonyl)phenyl)phenyl)carbonyl)-N-(2-(3-methoxy-4-ethoxyphenyl)ethyl)amino)propanoic acid,

(21) 3-(N-((2-(2-((4-chlorobenzylamino)carbonyl)phenyl)phenyl)carbonyl)-N-(2-(3-methoxy-4-ethoxyphenyl)ethyl)amino)propanoic acid,

(22) 3-(N-((2-(2-((4-methoxybenzylamino)carbonyl)phenyl)phenyl)carbonyl)-N-(2-(3-methoxy-4-ethoxyphenyl)ethyl)amino)propanoic acid,

(23) 3-(N-((2-(2-((4-methylbenzylamino)carbonyl)phenyl)phenyl)carbonyl)-N-(2-(3-methoxy-4-ethoxyphenyl)ethyl)amino)propanoic acid,

(24) 3-(N-((2-(2-((4-fluorobenzylamino)carbonyl)phenyl)phenyl)carbonyl)-N-(2-(3-methoxy-4-ethoxyphenyl)ethyl)amino)propanoic acid,

(25) 3-(N-((2-(2-(((1R)-1-(4-methylphenyl)ethylamino)carbonyl)phenyl)phenyl)carbonyl)-N-(2-(3-methoxy-4-ethoxyphenyl)ethyl)amino)propanoic acid,

(26) 3-(N-((2-(2-((1-(4-fluorophenyl)ethylamino)carbonyl)phenyl)phenyl)carbonyl)-N-(2-(3-methoxy-4-ethoxyphenyl)ethyl)amino)propanoic acid,

(27) 3-(N-((2-(2-((pyridin-3-ylmethylamino)carbonyl)phenyl)phenyl)carbonyl)-N-(2-(3,5-dimethoxyphenyl)ethyl)amino)propanoic acid,

(28) 3-(N-((2-(2-((4-chlorobenzylamino)carbonyl)phenyl)phenyl)carbonyl)-N-(2-(3,5-dimethoxyphenyl)ethyl)amino)propanoic acid,

(29) 3-(N-((2-(2-(((1R)-1-(4-methylphenyl)ethylamino)carbonyl)phenyl)phenyl)carbonyl)-N-(2-(3,5-dimethoxyphenyl)ethyl)amino)propanoic acid,

(30) 3-(N-((2-(2-((4-chlorobenzylamino)carbonyl)phenyl)phenyl)carbonyl)-N-(2-(2-ethoxyphenyl)ethyl)amino)propanoic acid,

(31) 3-(N-((2-(2-((4-chlorobenzylamino)carbonyl)phenyl)phenl)carbonyl)-N-(2-(3-ethoxyphenyl)ethyl)amino)propanoic acid,

(32) 3-(N-((2-(2-(((1S)-1-phenyl-2-hydroxyethylamino)carbonyl)phenyl)phenyl)carbonyl)-N-(benzyl)amino)propanoic acid,

(33) 3-(N-((2-(2-((4-methylbenzylamino)carbonyl)phenyl)phenyl)carbonyl)-N-(2-(4-ethoxyphenyl)ethyl)amino)propanoic acid,

(34) 3-{[(2'-{[(3-chlorobenzyl)amino]carbonyl}-2-biphenylyl)carbonyl][2-(4-ethoxy-3-methoxyphenyl)ethyl]amino}propanoic acid,

(35) N-[2-(4-ethoxyphenyl)ethyl]-N-[(2'-{[(pyridin-3-ylmethyl)amino]carbonyl]biphenyl-2-yl)carbonyl}-β-alanine,

(36) 2-(3,5-dimethyl-4-{[(3-phenylpropyl)(2-propylpentanoyl)amino]methyl}-1H-pyrazol-1-yl)benzoate hydrochloride,

(37) (4'-{[(3-phenylpropyl)(3,4,5-trimethoxybenzoyl)amino]methyl}-2-biphenylyl)acetic acid,

(38) 2-(4-{[(3,5-dimethoxybenzoyl)(3-phenylpropyl)amino]methyl}phenoxy)benzoic acid,

(39) 4'-{[(3-phenylpropyl)(3,4,5-trimethoxybenzoyl)amino]methyl}-2-biphenylcarboxylic acid,

(40) 4'-({(2,5-dichlorobenzoyl)[3-(4-methoxyphenyl)propyl]amino}methyl)-2-biphenylcarboxylic acid,

(41) 4'-{[(3,5-dimethoxybenzyl)(3-phenylpropanoyl)amino]methyl}-2-biphenylcarboxylic acid,

(42) 4'-{[(3,5-dichlorobenzyl)(3-phenylpropanoyl)amino]methyl}-2-biphenylcarboxylic acid,

(43) 4'-{[(3,5-dimethoxybenzyl)(3-phenylpropyl)amino]carbonyl}-2-biphenylcarboxylic acid,

(44) 4'-{[(2,5-dichlorobenzyl)(3-phenylpropyl)amino]carbonyl}-2-biphenylcarboxylic acid,

(45) (4-{[(3,5-dimethoxy-4-methylbenzoyl)(3-phenylpropyl)amino]methyl}phenyl)acetic acid,

(46) 2-(4-{[(3,5-dimethoxy-4-methylbenzoyl)(3-phenylpropyl)amino]methyl}phenoxy)-4-methylbenzoic acid,

(47) 2-[2-(3,5-dimethoxybenzoyl)-1-(2-phenylethyl)-1H-benzimidazol-6-yl]benzoic acid,

(48) 2-{[2-(3,5-dimethoxybenzoyl)-1-(2-phenylethyl)-1H-benzimidazole-6-yl]oxy}benzoic acid, prodrugs of the compounds as mentioned above (1) to (48) or salts thereof.

The compound of formula (II) is described in detail in the specification of WO 01/60819. In the compound of formula (II), preferable ones are described in the examples of the specification of WO 01/60819.

Above all the preferable is methyl 3-({4-[4-({[1-(2-chlorophenyl)ethoxy]carbonyl}amino)-3-methyl-5-isoxazolyl]benzyl}sulfanyl)propanoate, which is described in the example 115.

In the present invention, all isomers are included unless specified. For example, alkyl, alkoxy, alkylthio, alkenyl, alkynyl and alkylene include straight and branched ones. Furthermore, the present invention includes isomers in double bond, ring, fused ring (E, Z, cis, trans), isomers by the existence of asymmetric carbon etc. (R, S, α, β, enantiomer, diastereomer), optical isomers having optical rotation (D, L, d, l), polars by chromatography separation (more polar, less polar), equilibrium compounds, rotational isomers, compounds of arbitrary ratios of those and racemic mixture.

The effect of LPA which mediates EDG-2 accelerates the proliferation of airway smooth muscle cells, mesangium cells, fat cells, prostate stroma cells, coronary artery cells, synovial cells, dendritic cells, etc., so that various chronic diseases are induced. Concretely, chronic asthma, glomerular nephritis, obesity, prostate hyperplasia, diseases induced by the progress of arteriosclerosis (e.g. arteriosclerosis, cardiac failure, angina, unstable angina, myocardial infarction, cerebral infarction, aortic aneurysm, renal infarction, etc.) rheumatoid and atopic dermatitis, etc. Therefore, an EDG-2 antagonist is useful for the treatment and/or prevention of chronic diseases such as chronic asthma, glomerular nephritis, obesity, prostate hyperplasia, diseases induced by the progress of arteriosclerosis (e.g. arteriosclerosis, cardiac failure, angina, unstable angina, myocardial infarction, cerebral infarction, aortic aneurysm, renal infarction, etc.) rheumatoid and atopic dermatitis, etc. Therefore the compounds of formula (I), (II) and (III), possessing an EDG-2 antagonistic effect, are useful for the treatment and/or prevention of chronic diseases such as chronic asthma, glomerular nephritis, obesity, prostate hyperplasia, diseases induced by the progress of arteriosclerosis (e.g. arteriosclerosis, cardiac failure, angina, unstable angina, myocardial infarction, cerebral infarction, aortic aneurysm, renal infarction, etc.) rheumatoid and atopic dermatitis, etc.

The compound of formula (I) and a prodrug thereof may be prepared according to the following method.

The compound of formula (I) may be prepared by subjecting to a deprotection reaction of protective groups of carboxy the compound of formula (I-1)

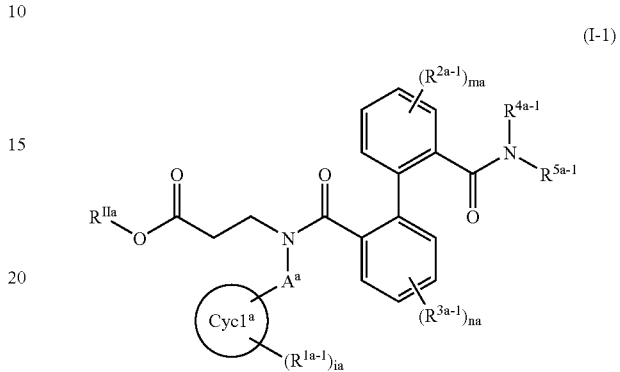

(I-1)

(wherein $R^{IIa}$ is a protective group of carboxy, $R^{1a-1}$, $R^{2a-1}$, $R^{3a-1}$, $R^{4a-1}$, and $R^{5a-1}$ have the same meaning as $R^{1a}$, $R^{2a}$, $R^{3a}$, $R^{4a}$, and $R^{5a}$, and hydroxy, amino or thiol group included in a group represented by $R^{1a-1}$, $R^{2a-1}$, $R^{3a-1}$, $R^{4a-1}$ and $R^{5a-1}$ and the other symbols have the same meaning as hereinbefore.), further optionally followed by subjecting to a deprotection reaction of the protective groups.

Protective groups of carboxy include, for example, methyl, ethyl, allyl t-butyl, trichloroethyl, benzyl (Bn), phenacyl, p-methoxybenzyl, trityl, 2-chlorotrityl or a solid carrier to which the structure thereof is attached, etc.

Deprotection reactions of the protective groups of carboxy are well known, for example, 1) a deprotection reaction by alkali hydrolysis, 2) a deprotection reaction under acidic conditions, 3) a deprotection reaction by hydration, 4) a deprotection reaction by using a metal, 5) a deprotection reaction by using a metal complex, etc. may be included.

To explain these methods concretely;

1) The deprotection reaction by alkali hydrolysis is carried out, for example, in an organic solvent (methanol, tetrahydrofuran, dioxane, etc.) using a hydroxide of alkali metals (sodium hydroxide, potassium hydroxide, lithium hydroxide, etc.), hydroxide of alkaline earth metals (barium hydroxide, calcium hydroxide, etc.), carbonate (sodium carbonate, potassium carbonate, etc.) or a solution thereof or a mixture thereof at a temperature of 0 to 40° C.;

2) The deprotection reaction under acidic conditions is carried out, for example, in an organic solvent (dichloromethane, chloroform, dioxane, ethyl acetate, anisole, etc.), using an organic acid (acetic acid, trifluoroacetic acid, methanesulfonic acid, p-toluenesulfonic acid, etc.) or an inorganic acid (hydrochloric acid, sulfuric acid, etc.) or a mixture thereof (hydrobromic acid/acetic acid, etc.) at a temperature of 0 to 100° C.;

3) The deprotection reaction by hydration is, for example, carried out in a solvent (ethers (tetrahydrofuran, dioxane, dimethoxyethane, diethyl ether, etc.), alcohols (methanol, ethanol, etc.), benzenes (benzene, toluene, etc.), ketones (acetone, methyl ethyl ketone, etc.), nitriles (acetonitrile etc.), amides (dimethylformamide etc.), water, ethyl acetate, acetic acid or a mixture of more than two from above, etc.) in the presence of a catalyst (palladium-carbon, palladium black, palladium hydroxide, platinum oxide, Raney nickel, etc.) under the atmosphere of hydrogen of normal or suppressed pressure, or in the presence of ammonium formate at a temperature of 0 to 200° C.

As easily understood by those skilled in the art, the compounds of the present invention may be easily prepared by selecting these reactions.

4) The deprotection reaction by using a metal is carried out, for example, in an acidic solvent (acetic acid, a buffer of pH 4.2 to 7.2 or a mixture of the solution thereof and an organic solvent such as tetrahydrofuran etc.) in the presence of zinc powder optionally under sonication at a temperature of 0 to 40° C.

5) The deprotection reaction by using a metal complex is carried out, for example, in an organic solvent (dichloromethane, dimethylformamide, tetrahydrofuran, ethyl acetate, acetonitrile, dioxane, ethanol, etc.), water or a mixture thereof, in the presence of a trap reagent (tributyltin hydride, triethylsilane, dimedone, morpholine, diethylamine, pyrrolidine, etc.), an organic acid (acetic acid, formic acid, 2-ethylhexane, etc.) and/or a salt of an organic acid (sodium 2-ethylhexanoate, potassium 2-ethylhexanoate, etc.) in the presence or absence of phosphine reagent (triphenylphosphine etc.) using a metal complex (palladium tetrakistriphenylphosphine (0), palladium bis(triphenylphosphine) dichloride (II), palladium acetate (II), rhodium tris(triphenylphosphine) chloride (I), etc. at a temperature of 0 to 40° C.

As easily understood by those skilled in the art, the compounds of the present invention may be easily prepared by selecting these reactions.

In addition to the above, deprotection reactions are carried out according to the methods described in T. W. Greene, Protective Groups in Organic Synthesis, Wiley, N.Y., 1999 are used.

As easily understood by those skilled in the art, the compound of the present invention is easily prepared by selecting these deprotection reactions.

Protective groups for carboxy include, for example, methyl, ethyl, t-butyl, benzyl, etc.

Protective groups for hydroxy include, for example, methyl, trityl, methoxymethyl (MOM), 1-ethoxyethyl (EE), methoxyethoxymethy (MEM), 2-tetrahydropyranyl (THP), trimethylsilyl (TMS), triethylsilyl (TES), t-butyldimethylsilyl (TBDMS), t-butyldiphenylsilyl (TBDPS), acetyl (Ac), pivaloyl, benzoyl, benzyl (Bn), p-methoxybenzyl, allyloxycarbonyl (Alloc), 2,2,2-trichloroethoxycarbonyl (Troc), etc.

Protective groups for amino include, for example, benzyloxycarbonyl, t-butoxycarbonyl, allyloxycarbonyl (Alloc), 1-methyl-1-(4-biphenyl)ethoxycarbonyl (Bpoc), trifluoroacetyl, 9-fluorenylmethoxycarbonyl (Fmoc), benzyl (Bn), p-methoxybenzyl, benzyloxymethyl (BOM), 2-(trimethylsilyl)ethoxymethyl(SEM), etc.

Protective groups for thiol include, for example, benzyl, methoxybenzyl, methoxymethyl (MOM), 2-tetrahydropyranyl (THP), diphenylmethyl, acetyl (Ac), etc.

Protective groups for hydroxy, amino or thiol are not limited to the above groups, but those groups eliminated easily and selectively are also allowed. For example, the ones described in T. W. Greene, Protective Groups in Organic Synthesis, Wiley, N.Y., 1999 are used.

The deprotection reactions of protective groups for hydroxy, amino or thiol are well known, for example, 1) a deprotection reaction by alkali hydrolysis, 2) a deprotection reaction under acidic conditions, 3) a deprotection reaction by hydration, 4) a deprotection reaction of silyl group, 5) a deprotection reaction by using a metal, 6) a deprotection reaction by using a metal complex, etc. may be included.

The methods of 1)-3), 5) and 6) may be carried out as described hereinbefore.

4) The deprotection reaction of silyl group is carried out, for example, tetrabutylammonium fluoride at a temperature of 0 to 40° C.

The compound of formula (IA), which is a prodrug of the compound of formula (I) may be prepared by subjecting to an esterification reaction the compound of formula (IA-1)

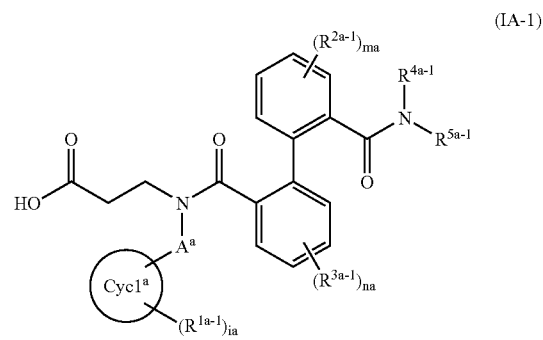

(wherein all symbols have the same meaning as described hereinbefore.) and the compound of formula (IV)

$R^{42a-1}$—OH (IV)

(wherein $R^{42a-1}$ has the same meaning as $R^{42a}$, and hydroxy or amino included in the group represented by $R^{42a-1}$ is protected if required, and the other symbols have the same meaning as described hereinbefore.), further optionally followed by subjecting to a deprotection reaction of the protective groups.

The esterification reaction is known, for example, 1) a method using acid halide, 2) a method using mixed anhydride, 3) a method using a condensing agent (EDC, DCC, etc.), etc.

To explain these methods concretely;

1) The method using acid halide is carried out, for example, by subjecting to a reaction carboxylic acid and acid-halogenating agent (oxalyl chloride, thionyl chloride, etc.) in an organic solvent (chloroform, dichloromethane, diethyl ether, tetrahydrofuran, etc.) or without a solvent, between −20° C. and refluxing temperature, and then subjecting to a reaction thus obtained acid halide in the presence of a tertiary amine (pyridine, triethylamine, dimethylaniline, dimethylaminopyridine, diisopropylethylamine, etc.) in an inert organic solvent (chloroform, dichloromethane, diethyl ether, tetrahydrofuran, etc.) at a temperature of 0 to 40° C. And, the reaction may also be carried out by subjecting to a reaction in an organic solvent (dioxane, tetrahydrofuran, etc.) using an alkali aqueous solution (an aqueous solution of sodium bicarbonate or sodium hydroxide, etc.) with an acid halide at a temperature of 0 to 40° C.;

2) The method using mixed anhydride is carried out, for example, by subjecting to a reaction in an organic solvent (chloroform, dichloromethane, diethyl ether, tetrahydrofuran, etc.) or without a solvent, in the presence of a base (pyridine, triethylamine, dimethylaniline, dimethylaminopyridine, dilsopropylethylamine, etc.), carboxylic acid with acid halide (pivaloyl chloride, tosyl chloride, mesylchloride, etc.) or an acid derivative (chloroethyl formate, chloroisobutyl formate, etc.) at a temperature of 0 to 40° C., and then subjecting to a reaction thus obtained mixed anhydride with amine in an organic solvent (chloroform, methylene chloride, diethyl ether, tetrahydrofuran, etc.) at a temperature of 0 to 40° C.;

3) The method using a condensing agent is carried out, for example, in an organic solvent (chloroform, methylene chloride, dimethylformamide, diethyl ether, tetrahydrofuran, etc.) or without a solvent, in the presence or absence of a tertiary amine (pyridine, triethylamine, dimethylaniline, dimethylaminopyridine, etc.), using a condensing agent (1,3-dicyclohexylcarbodiimide (DCC), 1-ethyl-3-[3-(dimethyl amino)propyl]carbodiimide (EDC), 1,1'-carbonyldiimidazole (CDI), 2-chloro-1-methylpyridinium iodide, 1-propylphosphonic acid cyclic anhydride (PPA), etc.) in the presence or absence of 1-hydroxybenzotriazole (1-HOBt), by subjecting to a reaction carboxylic acid and amine at a temperature of 0 to 40° C.

The reactions 1), 2) and 3) are desirably carried out under atmosphere of inert gas (argon, nitrogen, etc.) and anhydrous conditions.

The deprotection reaction of the protective groups for hydroxy, amino or thiol may be carried out by the same method described hereinbefore.

The compound of formula (IA) may be prepared by subjecting to an amidation reaction the compound of formula (IC-1)

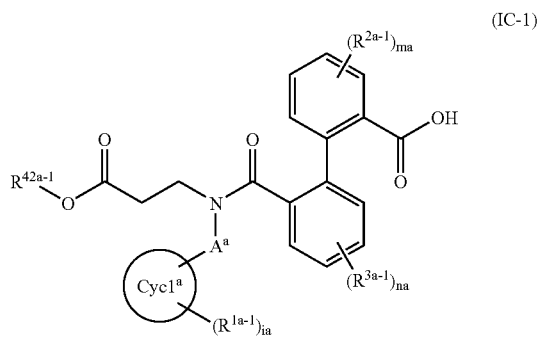

(wherein all symbols have the same meaning as described hereinbefore.) and the compound of formula (V)

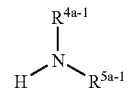

(V)

(wherein all symbols have the same meaning as described hereinbefore.), further optionally followed by subjecting to deprotection reaction of protective groups.

The amidation reaction is known, for example, 1) a method using acid halide, 2) a method using mixed anhydride, 3) a method using a condensing agent (EDC, DCC, etc.), etc.

To explain these methods concretely, 1) the method using acid halide is carried out, for example, by subjecting to a reaction carboxylic acid and acid-halogenating agent (oxalyl chloride, thionyl chloride, etc.) in an organic solvent (chloroform, dichloromethane, diethyl ether, tetrahydrofuran, etc.) or without a solvent, between −20° C. and refluxing temperature, and then subjecting to a reaction thus obtained acid halide in the presence of a tertiary amine (pyridine, triethylamine, dimethylaniline, dimethylaminopyridine, diisopropylethylamine, etc.) in an inert organic solvent (chloroform, dichloromethane, diethyl ether, tetrahydrofuran, etc.) at a temperature of 0 to 40° C. And, the reaction may also be carried out by subjecting to a reaction in an organic solvent (dioxane, tetrahydrofuran, etc.) using an alkali aqueous solution (an aqueous solution of sodium bicarbonate or sodium hydroxide, etc.) with an acid halide at a temperature of 0 to 40° C.

2) The method using mixed anhydride is carried out, for example, by subjecting to a reaction in an organic solvent (chloroform, dichloromethane, diethyl ether, tetrahydrofuran, etc.) or without a solvent, in the presence of a base (pyridine, triethylamine, dimethylaniline, dimethylaminopyridine, diisopropylethylamine, etc.), carboxylic acid with acid halide (pivaloyl chloride, tosyl chloride, mesylchloride, etc.) or acid derivative (chloroethyl formate, chloroisobutyl formate, etc.) at a temperature of 0 to 40° C., and then subjecting to a reaction thus obtained mixed anhydride with amine in an organic solvent (chloroform, methylene chloride, diethyl ether, tetrahydrofuran, etc.) at a temperature of 0 to 40° C.

3) The method using a condensing agent is carried out, for example, in an organic solvent (chloroform, methylene chloride, dimethylformamide, diethyl ether, tetrahydrofuran, etc.) or without a solvent, in the presence or absence of a tertiary amine (pyridine, triethylamine, dimethylaniline, dimethylaminopyridine, etc.), using a condensing agent (1,3-dicyclohexylcarbodiimide (DCC), 1-ethyl-3-[3-(dimethyl amino)propyl]carbodiimide (EDC), 1,1'-carbonyldiimidazole (CDI), 2-chloro-1-methylpyridinium iodide, 1-propylphosphonic acid cyclic anhydride (PPA), etc.) in the presence or absence of 1-hydroxybenzotriazole (1-HOBt), by subjecting to a reaction carboxylic acid and amine at a temperature of 0 to 40° C.

The reactions 1), 2) and 3) are desirably carried out under atmosphere of inert gas (argon, nitrogen, etc.) and anhydrous conditions.

The deprotection reaction of the protective groups of hydroxy or amino may be carried out by the same method as described hereinbefore.

The compound of formula (IB) which is a prodrug of the compound of formula (I) may be prepared by subjecting to an amidation reaction the compound of formula (IA-1) and the compound of formula (VI)

(VI)

(wherein $R^{43a-1}$ andn $R^{44a-1}$ has the same meaning as $R^{43a}$ and $R^{44a}$, and hydroxy or amino included in the group represented by $R^{43a-1}$ and $R^{44a-1}$ are protected if required. And the other symbols have the same meaning as described hereinbefore.), further optionally followed by subjecting to a deprotection reaction of the protective groups.

The amidation reaction may be carried out by the same method as described hereinbefore.

The deprotection reaction of the protective groups of hydroxy, amino or thiol may be carried out by the same method described hereinbefore.

The compound of formula (IC), which is a prodrug of the compound of formula (I) may be prepared by subjecting to a reduction reaction the compound of formula (IA-1), further optionally followed by subjecting to a deprotection reaction of the protective groups.

The reduction reaction is known, for example, carried out (1) in an organic solvent (chloroform, dichloromethane, diethyl ether, tetrahydrofuran, etc.) or without a solvent, in the presence or absence of a base (pyridine, triethylamine, dimethylaniline, dimethylaminopyridine, diisopropylethylamine, N-methylmorpholine, etc.), by subjecting to a reaction carboxylic acid with acid halide (oxalyl chloride, thionyl chloride, etc.), acid anhydride (acetic anhydride etc.), or acid derivative (chloroethylformate, chloroisobutylformate, etc.) at a temperature of −20-60° C., and then subjecting thus given compound in an solvent (methanol, tetrahydrofuran, water, etc.), with a reducing agent (sodium borohydride, tetrabutylammonium borohydride, calcium borohydride, etc.) at a temperature of 0-60° C., or (2)in an organic solvent (tetrahydrofuran, toluene, etc.), by subjecting to a reaction carboxylic acid with a reducing agent (diborane, borane-pyridine complex, borane-methylsulfide complex, diisobutylaluminum hydride, etc.) at a temperature of −80-0° C.

The deprotection reaction of the protective groups of hydroxy, amino or thio may be carried out by the same method described hereinbefore.

The compounds of formula (I-1), (IA-1) and (IC-1) are known per se or they may be prepared easily by known methods. For example, they may be prepared by the methods described in the following reaction scheme 1.

In the reaction scheme, X represents a leaving group (the leaving group represents halogen, mesyloxy, tosyloxy, etc.) and the other symbols have the same meaning as hereinbefore.

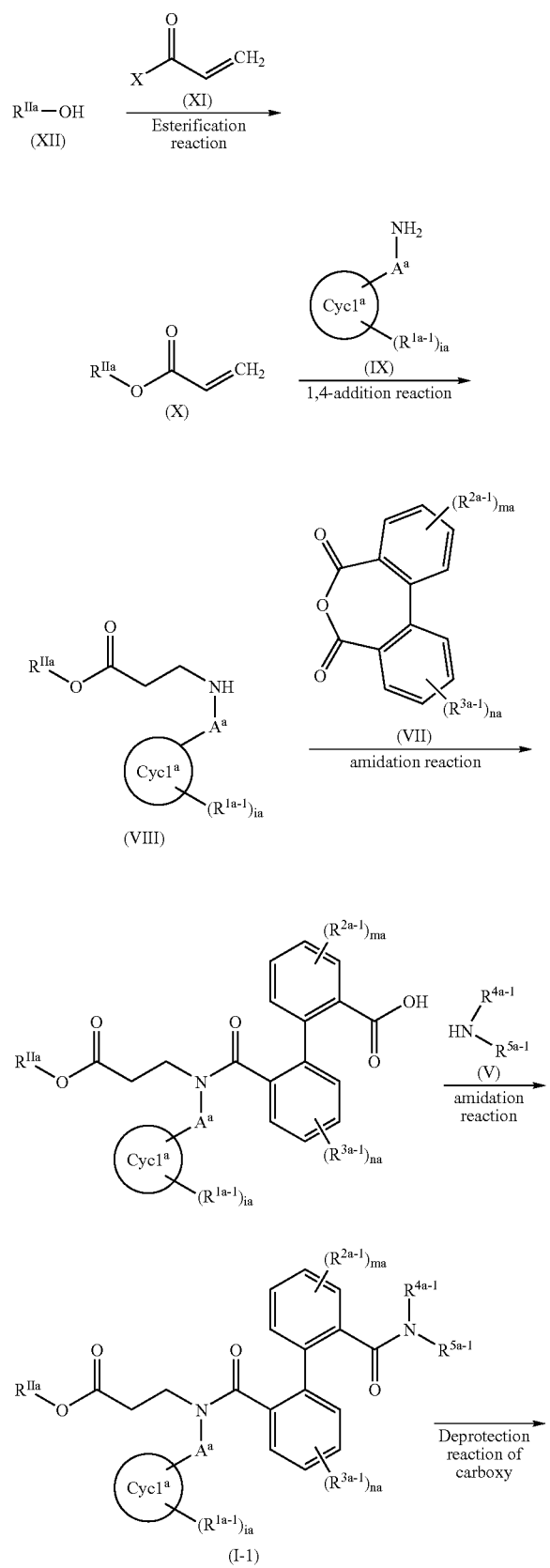

Reaction Scheme 1

-continued

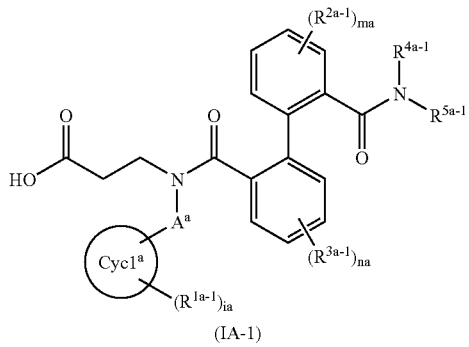

(IA-1)

In the reaction scheme 1, the compounds used as starting materials or reagents are known or may be prepared easily by known methods.

The compound of formula (III) may be prepared by known methods per se, for example the following methods, methods according to them or the methods described in the examples. In the method for the preparation as described hereafter, salts of the starting materials may be used. As such salts, the salts of the compound of formula (III) as described hereinbefore may be used.

In the compound of formula (III), the compound wherein $T^c$ is carbonyl and $J^c$ is nitrogen, i.e. the compound of formula (III-1)

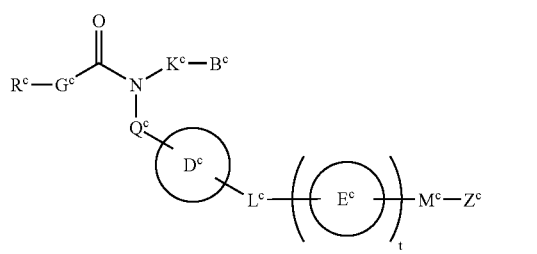

(III-1)

[wherein all symbols have the same meaning as described hereinbefore.] may be prepared by the following methods.

The compound of formula (III-1) may be prepared by subjecting to an amidation reaction the compound of formula (2)

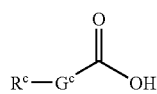

(2)

[wherein all symbols have the same meaning as described hereinbefore.] and the compound of formula (3)

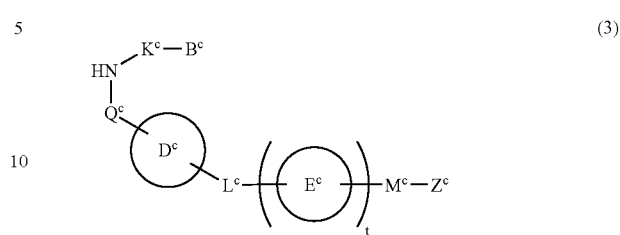

(3)

[wherein all symbols have the same meaning as described hereinbefore.].

The amidation reaction is known, for example, 1) a method using acid halide, 2) a method using mixed anhydride, 3) a method using a condensing agent, etc.

To explain these methods concretely, 1) the method using acid halide is carried out, for example, by subjecting to a reaction carboxylic acid and acid-halogenating agent (oxalyl chloride, thionyl chloride, phosphorous oxychloride, phosphorus trichloride, phosphorus pentachloride, etc.) in an organic solvent (chloroform, dichloromethane, diethyl ether, tetrahydrofuran, etc. alone or a mixture thereof of arbitrary ratio) or without a solvent, at a temperature of −20° C. to refluxing temperature, and then subjecting to a reaction thus obtained acid halide in the presence or absence of a base (pyridine, triethylamine, N,N-dimethylaniline, N,N-dimethylaminopyridine, diisopropylethylamine, etc.) in an organic solvent (chloroform, dichloromethane, diethyl ether, tetrahydrofuran, etc. alone or a mixture thereof of arbitrary ratio) at a temperature of −20 to 40° C. And, it may also be carried out by subjecting to a reaction thus given acid halide in an organic solvent (dioxane, tetrahydrofuran, etc. alone or a mixture thereof of arbitrary ratio) using an alkali aqueous solution (an aqueous solution of sodium bicarbonate or sodium hydroxide, etc.) with an amine at a temperature of −20 to 40° C.

2) The method using mixed anhydride is carried out, for example, by subjecting to a reaction in an organic solvent (chloroform, dichloromethane, diethyl ether, tetrahydrofuran, etc.) or without a solvent, in the presence of a base (pyridine, triethylamine, dimethylaniline, dimethylaminopyridine, diisopropylethylamine, etc.), carboxylic acid with acid halide (pivaloyl chloride, tosyl chloride, mesylchloride, etc.) or acid derivative (chloroethyl formate, chloroisobutyl formate, etc.) at a temperature of −20 to 40° C.; and then subjecting to a reaction thus obtained mixed anhydride with amine in an organic solvent (chloroform, methylene chloride, diethyl ether, tetrahydrofuran, etc.) at a temperature of −20 to 40° C.

3) The method using a condensing agent is carried out, for example, in an organic solvent (chloroform, methylene chloride, dimethylformamide, diethyl ether, tetrahydrofuran, etc.) or without a solvent, in the presence or absence of a tertiary amine (pyridine, triethylamine, dimethylaniline, dimethylaminopyridine, etc.), using a condensing agent (1,3-dicyclohexylcarbodiimide (DCC), 1-ethyl-3-[3-(dimethyl amino)propyl]carbodiimide (EDC), 1,1'-carbonyldiimidazole (CDI), 2-chloro-1-methylpyridinium iodide, 1-propylphosphonic acid cyclic anhydride (PPA), etc.) in the presence or absence of 1-hydroxybenzotriazole (1-HOBt), by subjecting to a reaction carboxylic acid and amine at a temperature of 0 to 40° C.

The reactions 1), 2) and 3) are desirably carried out under atmosphere of inert gas (argon, nitrogen, etc.) and anhydrous conditions.

In addition to the above described methods, sulfonamidation reaction is, for example, carried out by the methods described in "Comprehensive Organic Transformations: A Guide to Functional Group Preparations, 2nd Edition (Richard C. Larock, John Wiley & Sons Inc, 1999)."

The amidation reaction is known, for example, (1) a method using an acid halide, (2) a method using a mixed anhydride, (3) a method using a condensing agent, etc.

To explain these methods concretely, (1) the method using an acid halide is carried out, for example, by subjecting to a reaction carboxylic acid and acid-halogenating agent (oxalyl chloride, thionyl chloride, phosphoryl chloride, phosphorus trichloride, phosphorus pentachloride, etc.) in an organic solvent (chloroform, dichloromethane, diethyl ether, tetrahydrofuran, etc. alone or a mixture thereof of arbitrary ratios) or without a solvent, at a temperature of −20° C. to refluxing temperature, and then subjecting to a reaction thus obtained acid halide in the presence of an amine (pyridine, triethylamine, N,N-dimethylaniline, N,N-dimethylaminopyridine, diisopropylamine, etc.) in an inert organic solvent (chloroform, dichloromethane, diethyl ether, tetrahydrofuran, etc. or a mixture thereof of arbitrary ratios) at a temperature of −20 to 40° C. Further thus given acid halide may further be subjected to a reaction with amine in an organic solvent (1,4-dioxane, tetrahydrofuran, etc. or a mixture thereof of arbitrary ratio) using an aqueous alkali solution (an aqueous solution of sodium bicarbonate or sodium hydroxide, etc.) at a temperature of −20 to 40° C.

(2) The method using a mixed anhydride is carried out, for example, by subjecting to a reaction in an organic solvent (chloroform, dichloromethane, diethyl ether, tetrahydrofuran, etc. alone or a mixture thereof of arbitrary ratios) or without a solvent, in the presence of a base (pyridine, triethylamine, N,N-dimethylaniline, N,N-dimethylaminopyridine, diisopropylethylamine, etc.), carboxylic acid with acid halide (pivaloyl chloride, tosyl chloride, mesyl chloride, etc.) or an acid derivative (chloroethyl formate, chloroisobutyl formate, etc.) at a temperature of −20 to 40° C., and then subjecting to a reaction thus obtained mixed anhydride with an amine in an organic solvent (chloroform, dichloromethane, diethyl ether, tetrahydrofuran, etc. alone or a mixture thereof of arbitrary ratios) at a temperature of −20 to 40° C.

3) The method using a condensing agent is carried out, for example, in an organic solvent (chloroform, methylene chloride, dimethylformamide, diethyl ether, tetrahydrofuran, etc.) or without a solvent, in the presence or absence of a tertiary amine (pyridine, triethylamine, dimethylaniline, dimethylaminopyridine, etc.), using a condensing agent (1,3-dicyclohexylcarbodiimide (DCC), 1-ethyl-3-[3-(dimethyl amino)propyl]carbodiimide (EDC), 1,1'-carbonyldiimidazole (CDI), 2-chloro-1-methylpyridinium iodide, etc.) in the presence or absence of 1-hydroxybenzotriazole (1-HOBt), by subjecting to a reaction carboxylic acid and amine at a temperature of 0 to 40° C.

The reactions 1), 2) and 3) are desirably carried out under atmosphere of inert gas (argon, nitrogen, etc.) and anhydrous conditions.

In addition to the above described methods, amidation reaction is, for example, carried out by the methods described in "Comprehensive Organic Transformations: A Guide to Functional Group Preparations, 2nd Edition (Richard C. Larock, John Wiley & Sons Inc, 1999). "

In the compound of formula (III-1), the compound wherein at least one group includes carboxy, hydroxy, amino or thiol, may be prepared by subjecting to a deprotection reaction the compound each group is protected by protective groups.

Protective groups for carboxy include, for example, methyl, ethyl, allyl, t-butyl, trichloroethyl, benzyl (Bn), phenacyl, etc.

Protective groups for hydroxy include, for example, methyl, trityl, methoxymethyl (MOM), 1-ethoxyethyl (EE), methoxyethoxymethyl (MEM), 2-tetrahydropyranyl (THP), trimethylsilyl (TMS), triethylsilyl (TES), t-butyldimethylsilyl (TBDMS), t-butyldiphenylsilyl (TBDPS), acetyl (Ac), pivaloyl, benzoyl, benzyl (Bn), p-methoxybenzyl, allyloxycarbonyl (Alloc), 2,2,2-trichloroethoxycarbonyl (Troc) etc.

Protective groups for amino include, for example, benzyloxycarbonyl, t-butoxycarbonyl, allyloxycarbonyl (Alloc), 1-methyl-1-(4-biphenyl)ethoxycarbonyl (Bpoc), trifluoroacetyl, 9-fluorenylmhethoxycarbonyl, benzyl (Bn), p-methoxybenzyl, benzyloxymethyl (BOM), 2-(trimethylsilyl)ethoxymethyl (SEM), etc.

Protective groups for thiol include, for example, benzyl, methoxybenzyl, methoxymethyl (MOM), 2-tetrahydropyranyl (THP), diphenylmethyl, acetyl (Ac), etc.

Protective groups for carboxy, hydroxy, amino or thiol are not limited to the above groups, but those groups eliminated easily and selectively are also allowed. For example, the ones described in Protective Groups in Organic Synthesis (T. W. Greene, John Wiley & Sons Inc, 1999) are used.

Deprotection reactions of the protective groups for carboxy, hydroxy, amino or thiol are well known, for example, (1) alkaline hydrolysis, (2) a deprotection reaction under acidic conditions, (3) a deprotection reaction by hydration, (4) a deprotection reaction of silyl-containing groups, (5) a deprotection reaction using a metal, (6) a deprotection reaction using an organic metal, etc. may be included.

To explain these methods concretely;

(1) The deprotection reaction under alkaline conditions is carried out, for example, in an organic solvent (methanol, tetrahydrofuran, 1,4-dioxane, etc. alone or a mixture thereof of arbitrary ratio) using a hydroxide of alkali metals (sodium hydroxide, potassium hydroxide, lithium hydroxide, etc.), hydroxide of alkaline earth metals (barium hydroxide, calcium hydroxide, etc.) or a carbonate (sodium carbonate, potassium carbonate, etc.) or an aqueous solution thereof or a mixture thereof at a temperature of 0 to 40° C.;

(2) The deprotection reaction under acidic conditions is carried out, for example, in an organic solvent (dichloromethane, chloroform, 1,4-dioxane, ethyl acetate, anisole, etc. alone or a mixture thereof of arbitrary ratios), using an organic acid (acetic acid, trifluoroacetic acid, methanesulfonic acid, p-toluenesulfonic acid, etc.) or inorganic acid (hydrochloric acid, sulfuric acid, etc.) or a mixture thereof (hydrobromic acid/acetic acid, etc.) at a temperature of 0 to 100° C.;

(3) The deprotection reaction by hydration is, for example, carried out in a solvent (ethers (tetrahydrofuran, 1,4-dioxane, dimethoxyethane, diethyl ether, etc.), alcohols (methanol, ethanol, etc.), benzenes (benzene, toluene, etc.), ketones (acetone, methyl ethyl ketone, etc.), nitriles (acetonitrile etc.), amides (N,N-dimethylformamide etc.), water, ethyl acetate, acetic acid or a mixture of more than two from above, etc.) in the presence of a catalyst (palladium-carbon, palladium black, palladium hydroxide, platinum oxide, Raney nickel, etc.) under the atmosphere of hydrogen of normal or suppressed pressure, or in the presence of ammonium formate at a temperature of 0 to 200° C.

(4) The deprotection reaction of silyl group is carried out, for example, in a water-miscible organic solvent (tetrahydrofuran, acetonitrile, etc. alone or a mixture thereof of arbitrary ratios) using tetrabutylammonium fluoride at a temperature of 0 to 40° C.

(5) The deprotection reaction using a metal is, for example, carried out in an acidic solvent (acetic acid, a mixture of a buffer of pH 4.2 to 7.2 or a solution thereof and an organic solvent such as tetrahydrofuran etc.) in the presence of powder zinc under sonication or not at a temperature of 0 to 40° C.

(6) The deprotection reaction by using a metal complex is carried out, for example, in an organic solvent (dichloromethane, dimethylformamide, tetrahydrofuran, ethyl acetate, acetonitrile, dioxane, ethanol, etc.), water or a mixture thereof, in the presence of trap reagent (tributyltin hydride, triethylsilane, dimedone, morpholine, diethylamine, pyrrolidine, etc.), an organic acid (acetic acid, formic acid, 2-ethylhexane, etc.) and/or a salt of an organic acid (sodium 2-ethylhexanoate, potassium 2-ethylhexanoate, etc.) in the presence or absence of phosphine reagent (triphenylphosphine etc.) using a metal complex (palladium tetrakistriphenylphosphine (0), palladium bis(triphenylphosphine) dichloride (II), palladium acetate (II), rhodium tris(triphenylphosphine) chloride (I), etc. at a temperature of 0 to 40° C.

The deprotection reaction using a metal complex is carried out, for example, in an organic solvent (dichloromethane, N,N-dimethylformamide, tetrahydrofuran, ethyl acetate, acetonitrile, 1,4-dioxane, ethanol, etc.), water or a mixture thereof;

(a) Elimination of C1-2 alkyl is carried out by subjecting to a reaction in an organic solvent (chloroform etc.), using halogenated trimethylsilyl (e.g. trimethylsilyl chloride, trimethylsilyl bromide, trimethylsilyl iodide, etc.) as a reagent, in the presence or absence of alkali metal iodide (e.g. sodium iodide, potassium iodide, etc.) at a temperature of 0 to 40° C.

(b) Elimination of phenyl is carried out by subjecting to a reaction under atmosphere of hydrogen, in an organic solvent (methanol, ethanol, tetrahydrofuran, pyridine, acetic acid, etc.) or without a solvent, in the presence or absence of a catalyst (platinum oxide etc.) and an organic acid (acetic acid etc.) or inorganic acid (hydrochloric acid, etc.) at a temperature of 0 to 50° C. for 24 hours to 3 days.

(c) Elimination of benzyl is carried out by subjecting to a reaction in an organic solvent (methanol, ethanol, tetrahydrofuran, pyridine, acetic acid, etc.) in the presence or absence of a catalyst (palladium-carbon, palladium black, palladium hydroxide, etc.) at a temperature of 0 to 50° C.

(d) Elimination of 2,2,2-trichloroethyl is carried out in an organic solvent (methanol, ethanol, tetrahydrofuran, etc.) or without a solvent, using fine powder of zinc etc and an organic acid (acetic acid etc.) or an inorganic acid (hydrochloric acid etc.) at a temperature of 0 to 50° C.

(e) Elimination of cyanoethyl is carried out in a solvent (water, methanol, ethanol, tetrahydrofuran, pyridine, etc.) or without a solvent in the presence of a base (trimethylamine, dimethylamine, t-butylamine, etc.) at a temperature of 0 to 100° C.

The compound of formula (II), an intermediate of the compound of the present invention may be prepared according to the method described in the reaction scheme 3.

In addition to the above described methods, deprotection reaction is, for example, carried out by the methods described in "Protective Groups in Organic Synthesis (T. W. Greene, John Wiley & Sons Inc, 1999)."

As is easily understood by those skilled in the art, the target compounds of the present invention may be prepared easily by these deprotection reactions.

Optionally, converting into non-toxic salts may be carried out by known methods, following the above reactions.

In the compound of formula (III-1), the compound wherein $Z^c$ is —COOR$^{5c}$ and R$^{5c}$ is hydrogen, i.e. the compound of formula (III-1-2)

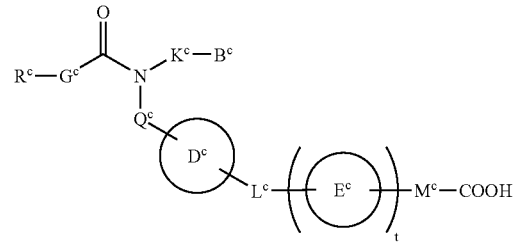

(III-1-2)

[wherein all symbols have the same meaning as described hereinbefore.] may be prepared by subjecting to a deprotection reaction of the protective group of carboxy the compound wherein $Z^c$ is —COOR$^{5c}$ and R$^{5c}$ is not hydrogen, i.e. the compound of formula (III-1-1)

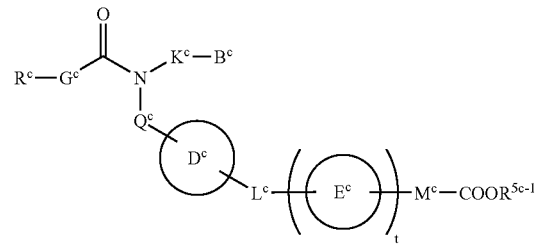

(III-1-1)

[wherein R$^{5c-1}$ has the same meaning as R$^{5c}$, with proviso that it does not represent hydrogen and the other symbols have the same meaning as described hereinbefore.], optionally followed by subjecting to a deprotection reaction of other protective groups.

In the compound of formula (III-1), the compound wherein $Z^c$ is —COOR$^{5c}$ and R$^{5c}$ is hydrogen, i.e. the compound of formula (III-1-2)

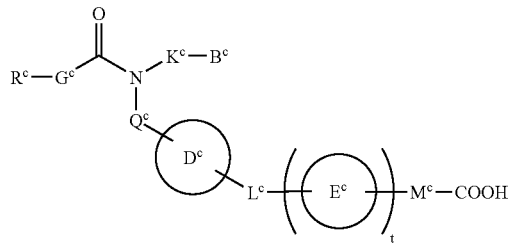

(III-1-2)

may be prepared by subjecting to a deprotection reaction of the protective groups of carboxy the compound wherein $Z^c$ is —COOR$^{5c}$ and R$^{5c}$ is not hydrogen atom, i.e. the compound of formula (III-1-1)

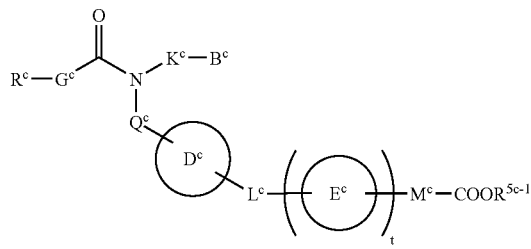

(III-1-1)

[wherein R$^{5c-1}$ has the same meaning as R$^{5c}$, with proviso that it does not represent hydrogen atom and the other symbols have the same meaning as described hereinbefore.].

Protective groups for carboxy includes, for example, methyl, ethyl, allyl, t-butyl, trichloroethyl, benzyl (Bn), phenacyl, p-methoxybenzyl, trityl, 2-chlorotrityl or a solid carrier to which the structures thereof are attached.

Deprotection reactions of protective groups for carboxy is well known, for example, (1) alkali hydrolysis, (2) a deprotection reaction under acidic conditions, (3) a deprotection reaction by hydration, (4) a deprotection reaction using a metal, (5) a deprotection reaction using an organic metal, etc.

These are carried out by the methods described hereinbefore.

The deprotection reaction of the protective groups may be carried out by the same method described hereinbefore.

In the compound of formula (III), the compound wherein $T^c$ is carbonyl, $J^c$ is nitrogen, a part of $Q^c$ is taken together with Kc to form five-membered ring, i.e. the compound of formula (III-2).

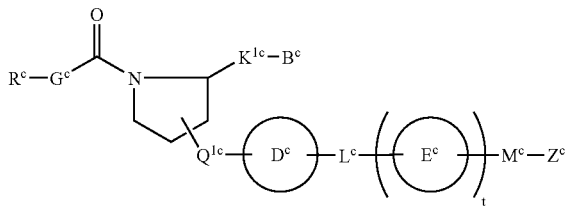

(III-2)

[wherein K$^{1c}$ has the same meaning as K$^c$, with proviso that it represents a spacer having a main chain of 1 to 7 atoms, Q$^{1c}$ has the same meaning as Q$^c$, with proviso that it represents a spacer having a main chain of 1 to 7 atoms and the other symbols have the same meaning as described hereinbefore.] may be prepared by subjecting to amidation reaction the compound of formula (2) above described and the compound of formula (4)

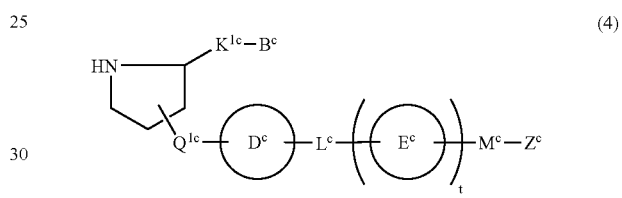

(4)

[wherein all symbols have the same meaning as described hereinbefore.], optionally followed by subjecting to a deprotection reaction of the protective groups.

The amidation reaction and the deprotection reaction of the protective groups may be carried out by the same method described hereinbefore.

In the compound of formula (III), the compound wherein $T^c$ is carbonyl, $J^c$ is nitrogen atom, $Q^c$ is methylene and a part of $K^c$ is taken together with a substituent of ring $D^c$ to form tetrahydroisoquinoline ring, i.e. the compound of formula (III-3)

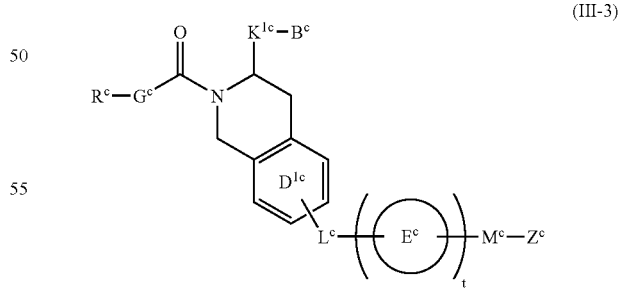

(III-3)

[wherein ring D$^{1c}$ has the same meaning as ring D$_c$, with a proviso that ring D$^{1c}$ represents benzene ring optionally having substituent(s), and the other symbols have the same meaning as described hereinbefore.] may be prepared by subjecting to an amidation reaction the compound of above formula (2) and the compound of formula (5)

(5)

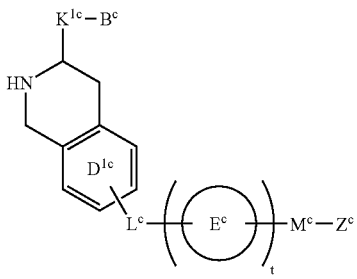

[wherein all symbols have the same meaning as described hereinbefore.], optionally followed by subjecting to a deprotection reaction of the protective groups.

The amidation reaction and the deprotection reaction of the protective groups may be carried out by the same method described hereinbefore.

In the compound of formula (III), the compound wherein $T^c$ is sulfonyl, $J^c$ is nitrogen, i.e. the compound of formula (III-4)

(III-4)

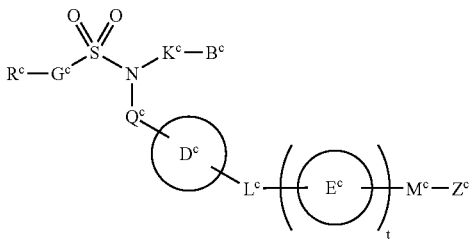

[wherein all symbols have the same meaning as described hereinbefore.] may be prepared by subjecting to a sulfonamidation reaction the compound of formula (6)

(6)

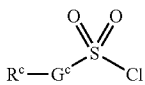

[wherein all symbols have the same meaning as described hereinbefore.] and the compound of above formula (3), optionally followed by subjecting to a deprotection reaction of the protective groups.

Sulfonamidation reaction is known, for example, it is carried out in an organic solvent (chloroform, dichloromethane, diethyl ether, tetrahydrdfuran etc. alone or a mixture thereof of arbitrary ratio) in the presence or absence of a base (pyridine, triethylamine, N,N-dimethylaniline, N,N-dimethylaminopyridine, diisopropylethylamine, etc.), by subjecting to a reaction sulfonyl chloride amine, at a temperature of 0-40° C. Further it may be carried out by subjecting to a reaction amine with sulfonyl chloride in an organic solvent (1,4-dioxane, tetrahydrofuran, etc. alone or a mixture thereof of arbitrary ratio) using an aqueous alkali solution (an aqueous solution of sodium bicarbonate or sodium hydroxide, etc.) at a temperature of 0 to 40° C.

Further, optionally the compound of the present invention may be prepared by subjecting to a deprotection reaction of the protective groups.

In addition to the above described methods, sulfonamidation reaction is, for example, carried out by the methods described in "Comprehensive Organic Transformations: A Guide to Functional Group Preparations, 2nd Edition (Richard C. Larock, John Wiley & Sons Inc, 1999)."

The deprotection reaction of the protective groups may be carried out by the same method described hereinbefore.

In the compound of formula (III), the compound wherein $G^c$ is nitrogen, $T^c$ is carbonyl, $J^c$ is nitrogen, i.e. the compound of formula (III-5)

(III-5)

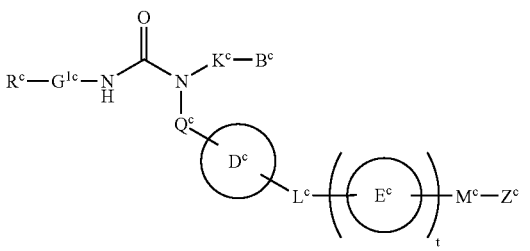

[wherein $G^{1c}$ has the same meaning as $G^c$, with proviso that it represents a bond or a spacer having a main chain of 1 to 7 atoms and the other symbols have the same meaning as described hereinbefore.] may be prepared by subjecting to a reaction of forming urea, optionally followed by subjecting to a deprotection reaction of the protective groups.

The reaction of forming urea is known, for example, it is carried out in an organic solvent (e.g. chloroform, dichloromethane, toluene, diethyl ether, tetrahydrofuran, etc. alone or a mixture thereof of arbitrary ratio) in the presence or absence of an amine (pyridine, triethylamine, N,N-dimethylaniline, N,N-dimethylaminopyridine, diisopropylethylamine, etc.) by subjecting to a reaction isocyanate derivative and a base (pyridine, triethylamine, N,N-dimethylaniline, N,N-dimethylaminopyridine, diisopropylethylamine, etc.), amine at a temperature of 0 to 130° C. Further, optionally the compound of the present invention may be prepared by subjecting to a deprotection reaction of the protective groups.

The deprotection reaction of the protective groups may be carried out by the same method described hereinbefore.

In the compound of formula (III), the compound wherein $T^c$ is methylene, $J^c$ is nitrogen and $Q^c$ is a group containing carbonyl (with proviso that the carbonyl is attached to $J^c$), i.e. the compound of formula (III-6)

(III-6)

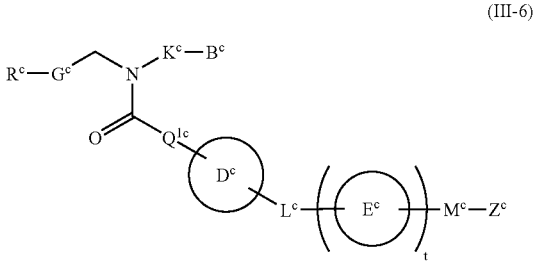

[wherein all symbols have the same meaning as described hereinbefore.] may be subjected to an amidation reaction the compound of formula (8)

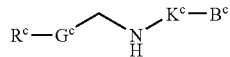
(8)

[wherein all symbols have the same meaning as described hereinbefore.] and the compound of formula (9)

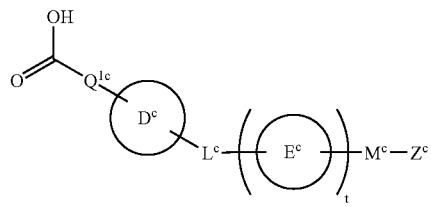
(9)

[wherein all symbols have the same meaning as described hereinbefore.], optionally followed by subjecting to a deprotection reaction of the protective groups.

The amidation reaction and the deprotection reaction of the protective groups may be carried out by the same method described hereinbefore.

In the compound of formula (III), the compound wherein $T^c$ is methylene, $J^c$ is nitrogen, i.e. the compound of formula (III-7)

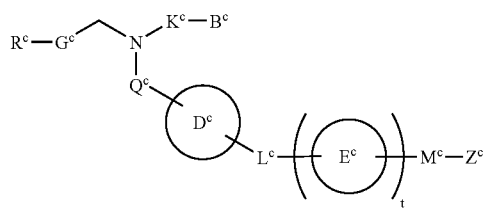
(III-7)

[wherein all symbols have the same meaning as described hereinbefore.] may be prepared by subjecting to reductiove amination reaction the compound of formula (10)

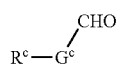
(10)

[wherein all symbols have the same meaning as described hereinbefore.] and the compound of the above (3), optionally followed by subjecting to a deprotection reaction of the protective groups.

Reductive amination reaction is known, for example, in an organic solvent (N,N-dimethylformamide, dichloromethane etc. alone or a mixture thereof of arbitrary ratio), in the presence or absence of an organic acid (acetic acid, etc.) or in the presence or absence of a base (triethylamine, sodium bicarbonate, etc.), using a reducing agent (sodium triacetoxyborohydride, sodium cyanoborohydride, ammonium tetrabutylborohydride, etc.), at a temperature of 0-100° C., optionally followed by subjecting to a deprotection reaction of the protective groups.

The deprotection reaction of the protective groups may be carried out by the same method described hereinbefore.

In the compound of formula (III), the compound wherein $T^c$ is carbonyl and $J^c$ is carbon, i.e. the compound of formula (III-8)

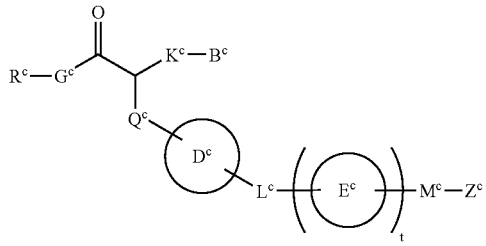
(III-8)

[wherein all symbols have the same meaning as described hereinbefore.] may be prepared by subjecting to a reaction the compound of formula (11)

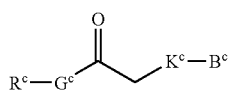
(11)

[wherein all symbols have the same meaning as described hereinbefore.] and the compound of formula (12)

(12)

[wherein, $X^c$ is a leaving group (leaving group means halogen, methanesulfonyloxy (OMs), p-toluenesulfonyloxy (OTs), trifluoromethanesulfonyloxy (OTf), etc.) and the other symbols have the same meaning as described hereinbefore.], optionally followed by subjecting to a deprotection reaction of the protective groups.

The reaction is known, for example, in an organic solvent (tetrahydrofuran, diethyl ether, acetonitrile, dimethylsulfoxide, etc. alone or a mixture thereof of arbitrary ratio), in the presence of a base (lithium diisopropylamine (optionally in the presence of an amine (N,N,N',N'',N''-pentamethyldiethylenetriamine, N,N,N',N'-tetramethylethylenediamine, etc.).) potassium carbonate, cesium carbonate, etc.), at a temperature of −78 to 40° C.

The deprotection reaction of the protective groups may be carried out by the same method described hereinbefore.

In the compound of formula (III), the compound wherein $T^c$ is —CHOH—, $J^c$ is carbon, i.e. the compound of formula (III-8-3)

(III-8-3)

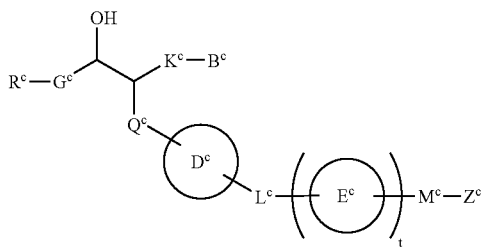

[wherein all symbols have the same meaning as described hereinbefore.] may be prepared by subjecting to reduction reaction the carbonyl group of the compound of formula (III-8), optionally followed by subjecting to a deprotection reaction of the protective groups.

The reduction reaction of carbonyl is known, for example, in an organic solvent (methanol, tetrahydrofuran or a mixture thereof etc.), using a reducing agent (sodium borohydride, sodium triacetoxyborohydride, sodium cyanoborohydride, tetrabutylammonium borohydride, etc.) at a temperature of 0 to 100° C.

The deprotection reaction of the protective groups may be carried out by the same method described hereinbefore.

In the compound of formula (III), the compound wherein, $T^c$ is carbonyl, $J^c$ is carbon, $Q^c$ is carbon and ring $D^c$ is taken together with $K^c$ to form indole ring, i.e. the compound of formula (III-9)

(III-9)

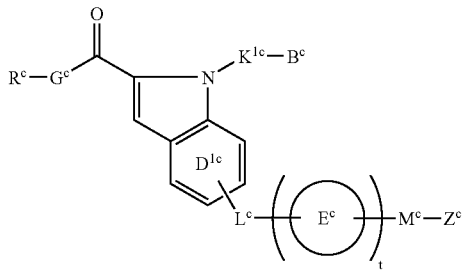

[wherein all symbols have the same meaning as described hereinbefore.] may be prepared by subjecting to a reaction the compound of formula (13)

(13)

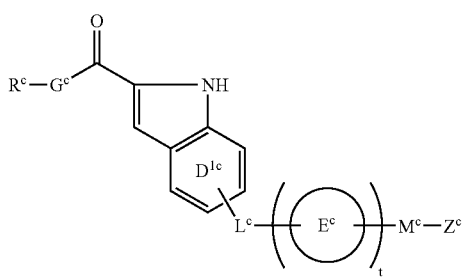

[wherein all symbols have the same meaning as described hereinbefore.] and the compound of formula (14)

(14)

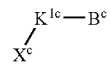

[wherein $X^c$ is a leaving group (the leaving group represents halogen, methanesulfonyloxy (OMs), p-toluenesulfonyloxy (OTs), trifluoromethanesulfonyloxy (OTf), etc.), and the other symbols have the same meaning as described hereinbefore.], optionally followed by subjecting to a deprotection reaction of the protective groups.

This reaction is known, for example, it is carried out in an organic solvent (tetrahydrofuran, diethyl ether, N,N-dimethylformamide, etc. alone or in a mixture thereof of arbitrary ratio), in the presence of a base (lithium diisopropylamine (optionally an amine (N,N,N',N'',N''-pentamethyldiethylenetriamine, N,N,N',N'-tetramethylethylenediamine, etc.).), sodium hydride, potassium carbonate, cesium carbonate, etc.) at a temperature of −78 to 40° C.

The deprotection reaction of the protective groups may be carried out by the same method described hereinbefore.

In the compound of formula (III), the compound wherein $T^c$ is carbonyl, $J^c$ is carbon, $Q^c$ is nitrogen, and ring $D^c$ is taken together with $K^c$ to form benzimidazole ring, i.e. the compound of formula (III-10)

(III-10)

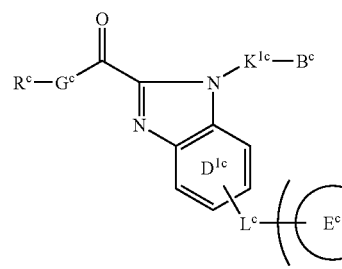

[wherein all symbols have the same meaning as described hereinbefore.] may be prepared by subjecting to a reaction the compound of formula (15)

(15)

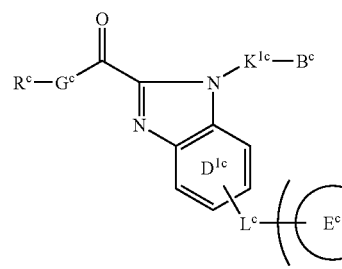

[wherein all symbols have the same meaning as described hereinbefore.] and the compound of formula (16)

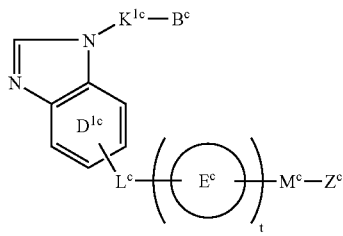

(16)

[wherein all symbols have the same meaning as described hereinbefore.], optionally followed by subjecting to a deprotection reaction of the protective groups.

The reaction is known, for example, it is carried out in an organic solvent (tetrahydrofuran, diethyl ether, etc. alone or a mixture thereof of arbitrary ratio), in the presence of a base (lithium diisopropylamine (optionally in the presence of an amine (N,N,N',N'',N''-pentamethyldiethylenetriamine, N,N,N',N'-tetramethyl ethylenediamine, etc.).), n-butyl lithium etc.), at a temperature of −78 to 40° C.

The deprotection reaction of the protective groups may be carried out by the method as described hereinbefore.

In the compound of formula (III), the compound wherein $Z^c$ is tetrazole group, i.e. the compound of formula (III-11)

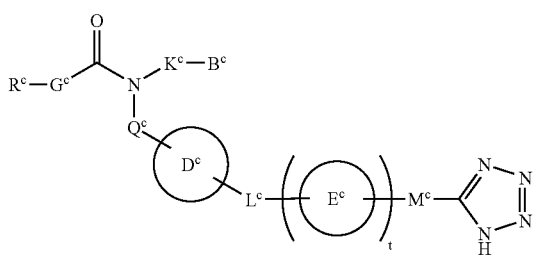

(III-11)

(all symbols have the same meaning as hereinbefore.) may be prepared by subjecting to a reaction the compound of formula (17)

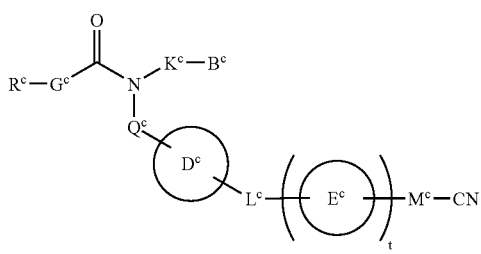

(17)

(all symbols have the same meaning as hereinbefore.) and an azide compound, optionally followed by subjecting to a deprotection reaction of protective groups.

The reaction is known, for example, it is carried out in water or an organic solvent (benzene, toluene, xylene, N,N-dimethylformamide, tetrahydrofuran, 1,4-dioxane, isopropanol, etc.) alone or a mixture thereof of arbitrary ratio, in the presence or absence of an additive agent (e.g. zinc bromide, lithium chloride, ammonium chloride, acetic acid, trifluoroacetic acid, triethylamine, pyridine, etc.), with an azide compound (for example, sodium azide, lithium azide, trimethylsilyl azide, trimethyltin azide, tributyltin azide, etc.) at a temperature of 20-150° C.

This reaction is known, for example, it is carried out in water or an organic solvent (benzene, toluene, xylene, N,N-dimethylformamide, tetrahydrofuran, 1,4-dioxane, isopropanol, etc.) alone, or a mixture consisting of arbitrary ratio of some selected from above, in the presence or absence of The compounds of formula (2) to (17), which are used as starting materials or reagents are known per se, or may be prepared according to the methods described in "Comprehensive Organic Transformation: A Guide to Functional Group Preparations, 2nd Edition (Richard C.Larock, John Wiley & Sons Inc, 1999)."

In the compound of formula (III), the compounds other than those described above may be prepared by the combination of Preparation Example described in the present specification and known methods, for example, those described in "Comprehensive Organic Transformations: A Guide to Functional Group Preparations, 2nd Edition (Richard C. Larock, John Wiley & Sons Inc, 1999)."

In each reaction of the present specification, reaction products may be purified by conventional techniques, for example, distillation under atmospheric or reduced pressure, high performance liquid chromatography, thin layer chromatography or column chromatography using silica gel or magnesium silicate, washing, recrystallization, etc. Purification may be carried out after each reaction, or after a series of reactions.

The compound of formula (II) may be prepared according to the methods described in the specification of WO01/60819.

[Toxicity]

The compound used in the present invention has low toxicity so that use of it as a pharmaceutical can be considered as safe enough.

INDUSTRIAL APPLICABILITY

[Application to Pharmaceuticals]

The EDG-2 antagonists used in the present invention bind to and antagonize EDG-2, and so it is useful for the treatment and/or prevention of diseases induced and made chronic by the acceleration of proliferation by LPA mediating EDG-2, e.g. chronic disease such as chronic asthma, glomerular nephritis, obesity, prostate hyperplasia, diseases induced by the progress of arteriosclerosis (e.g. arteriosclerosis, cardiac failure, angina, unstable angina, myocardial infarction, cerebral infarction, aortic aneurysm, renal infarction, etc.), rheumatoid and atopic diseases, etc.) induced and made chronic by tissue cells whose proliferation is accelerated by LPA mediated by EDG-2.

The EDG-2 antagonists used in the present invention are normally administered orally or parenterally, systemically or topically for the above purposes.

Moreover, in the present invention, the EDG-2 antagonist may also be administered as a concomitant agent in combination with other agents for 1) supplementing and/or reinforcement of preventive and/or treating effect(s) of the EDG-2 antagonist against chronic diseases, 2) improvement in kinetics and absorption of the EDG-2 antagonist and reduction of dose and/or 3) reduction of side effect of the EDG-2 antagonist.

Concomitant agents of the EDG-2 antagonist with other agents may be administered in a mode of compounded agent in which both components are compounded in a single preparation or in a mode of separate preparations. When administration is conducted using separate preparations, a simultaneous administration and administrations with time difference are included. In the case of administrations with time difference, the EDG-2 antagonist may be firstly administered and then the other drug may be administered, or the other drug may be firstly administered and then the EDG-2 antagonist may be administered. Each of the methods for the administration are the same or different.

Examples of the other drug for supplementing and/or reinforcing the preventive and/or treating effect of the EDG-2 antagonist against chronic asthma include, for example, steroidal agents, $\beta_2$ adrenergic receptor agonist, leukotriene receptor antagonist, thromboxane synthase inhibitor, thromboxane $A_2$ receptor antagonist, mediator liberation inhibitor, antihistamine agent, xanthine derivative, antichorinergic drug, cytokine inhibitor, prostaglandins, forskoline formulations, phosphddiesterase inhibitor, elastase inhibitor, metalloproteinase inhibitor, expectorant, antibiotics, etc.

Examples of the other drug for supplementing and/or reinforcing the preventive and/or treating effect of the EDG-2 antagonist against prostate hyperplasia include, for example, LPA receptor antagonist, antiandrogenic agent, (XI receptor blocker, 5α-reductase inhibor, etc.

Examples of the other drug for supplementing and/or reinforcing the preventive and/or treating effect of the EDG-2 antagonist against the diseases indeced by the progress of arteriosclerosis include, for example, HMG-CoA reductase inhibitors, fibrate preparations, probucol preparations, anion-exchange resin, EPA preparations, nicotinoic acid preparations, MTP (Microsomal Triglyceride Transfer Protein) inhibitors, PPAR agonist preparations, other antihypercholesterolemic agents.

Examples of the other drug for supplementing and/or reinforcing the preventive and/or treating effect of the EDG-2 antagonist against rheumatoid include, for example, non-steroidal anti-inflammatory drugs, disease-modifying antirheumatoidal drugs (slow-acting antirheumatic drugs), steroidal preparations, immunosuppressants, anti-inflammatory enzyme preparations, cartilage-protective agents, T cell inhibitors, TNFα inhibitors (protein preparations such as anti-TNFα antibody), prostaglandin synthase inhibitors, IL-6 inhibitors (inclusive of protein formuations such as anti-IL-6 receptor antibody, etc.), interferon γ-agonists, interferon γ agonists, IL-1 inhibitors, prostaglandins, phosphodiesterase inhibitors, metalloprotease inhibitors, etc.

Examples of the other drug for supplementing and/or reinforcing the preventive and/or treating effect of the EDG-2 antagonist against atopic dermatitis include, for example, steroidal preparations, non-steroidal anti-inflammatory drugs, immunosuppressants, prostaglandins, antiallergic agents, mediator liberation inhibitos, antihistamines, forscolin preparations, phosphodiesterase inhibitors, decoy preparations such as NF-κB, cannabinoid 2 receptor agonists, etc.

Steroidal preparations include, for example, as external medicines, clobetasol propionate, diflorasone acetate, fluocinonide, mometasone furoate, betamethasone dipropionate, betamethasone butyrate propionate, betamethasone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone lactate, hydrocortisone butyrate propionate, deprodone propionate, prednisolone valerate acetate, fluocinolone acetonid, beclomethasone dipropionate, triamcinolone acetonid, flumethasone pivalate, alclometasone dipropionate, beclomethasone lactate, prednisolone, beclomethasone dipropionate, fludroxycortide, etc.

Internal medicines and injections include, for example, cortisone acetate, hydrocortisone, sodium hydrocortisone phosphate, sodium hydrocortisone succinate, fludrocortisone acetate, prednisolone, prednisolone acetate, sodium prednisolone succinate, butyl prednisolone acetate, prednisolone sodium phosphate, halopredone acetate, methyl prednisolone, methyl prednisolone acetate, sodium methyl prednisolone succinate, triamcinolone, triamcinolone acetate, triamcinolone acetonid, dexamethasone, dexamethasone acetate, sodium dexamethasone phosphate, dexamethasone palmitate, paramethasone acetate, betamethasone, etc.

Inhalant medicines include, for example, beclometasone dipropionate, fluticasone propionate, budesonide, flunisolide, triamcinolone, ST-126P, ciclesonide, dexamethasone, paromitionate, mometasone furoate, prasterone sulfonate, deflazacort, methylprednisolone, sleptanate, methylprednisolone sodium succinate, etc.

$\beta_2$ adrenergic receptor agonists include, for example, fenoterol hydrobromide, salbutamol sulfate, terbutaline sulfate, formoterol fumarate, salmeterol xinafoate, isoproterenol sulfate, orciprenaline sulfate, clorprenaline sulfate, epinephrine, trimetoquinol hydrochloride, hexoprenalinemesyl sulfate, procaterol hydrochloride, tulobuterol hydrochloride, tulobuterol, pirbuterol hydrochloride, clenbuterol hydrochloride, mabuterol hydrochloride, ritodrine hydrochloride, bambuterol, dopexamine hydrochloride, meluadrine tartrate, AR-C68397, levosalbutamol, R,R-formoterol, KUR-1246, KUL-7211, AR-C89855, S-1319, etc.

Leukotriene receptor antagonists include, for example, pranlukast hydrate, montelukast, zafirlukast, seratrodast, MCC-847, KCA-757, CS-615, YM-158, L-740515, CP-195494, LM-1484, RS-635, A-93178, S-36496, BIIL-284, ONO-4057, etc.

Thromboxane synthase inhibitors include, for example, oxagrel hydrochloride, sodium imitrodast, etc.

Thromboxane $A_2$ receptor antagonists include, for example, seratrodast, ramatroban, domitroban calcium hydrate, KT-2-962, etc.

Mediator liberation inhibitors include, for example, tranilast, Sodium cromoglicate, amlexanox, repirinast, ibudilast, dazanolast, pemirolast potassium, etc.

Antihistamines includes, for example, ketotifen fumarate, mequitazine, azelastine hydrochloride, oxatomide, terphenadine, emedastine difumarate, epinastine hydrochloride, astemizole, ebastin, cetirizine hydrochloride, bepotastine, fexofenadine, loratadine, desloratadine, olopatadine hydrochloride, TAK-427, ZCR-2060, NIP-530, mometazone furoate, mizolastine, BP-294, andolast, auranofin, acrivastine, etc.

Xanthine derivatives include, for example, aminophylline, theophylline, doxophylline, cipamfylline, diprophylline, etc.

Anticholinergic agents include, for example, ipratropium bromide, oxitropiumu bromide, flutropium bromide, cimetropium bromide, temiverine, tiotropium bromide, revatropate (UK-112166), etc.

Cytokine inhibitors include, for example, suplatast tosylate (brand name: IPD), etc.

Prostaglandins (abbreviated as PG hereafter) include, PG receptor agonist, PG receptor antagonist, etc.

PG receptors include, PGE receptor ($EP_1$, $EP_2$, $EP_3$, $EP_4$), PGD receptor (DP, CRTH2), PGF receptor (FP), PGI receptor (IP), TX receptor (TP), etc.

Phosphodiesterase inhibitors include, for example, rolipram, cilomilast (brand name: Ariflo), Bayl9-8004, NIK-616, Roflumilast (BY-217), cipamfylline (BRL-61063), atizoram (CP-80633), SCH-351591, YM-976, V-11294A, PD-168787, D-4396, IC-485, etc.

Elastase inhibitors include, ONO-5046, ONO-6818, MR-889, PBI-1101, EPI-HNE-4, R-665, ZD-0892, ZD-8321, GW-311616, AE-3763, etc.

Expectorants include, for example, foeniculated ammonia spirit include, sodium bicarbonate, bromhexine hydrochloride, carbocysteine, ambroxol hydrochloride, ambroxol hydrochloride slow release formulation, methyl cysteine hydrochloride, acetylcysteine, L-ethylcysteine hydrochloride, tyloxapol, etc.

Antiandrogenergic agents include, for example, oxendolone, osaterone acetate, bicalutamide, etc.

$\alpha_1$ receptor blockers include, terazosin hydrochloride, bunazosin hydrochloride, urapidil, tamsulosin hydrochloride, doxazosin mesilate, prazosin hydrochloride, indolamine, naftopidil, alfuzosine hydrochloride, AIO-8507L, etc.

5α-reductase inhibitors include, for example, Finasteride, GI-998745, etc.

HMG-CoA reductase inhibitors include, simvastatin, lovastatin, pravastatin, fluvastatin, atorvastatin, pitavastatin, rosuvastatin.

Fibrates include, phenofibrate, clinofibrate, chlofibrate, chlofibrate aluminum, simfibrate, bezafibrate.

Probcol preparations include, probucol.

Nicotinic acid preparations include, tochoferol nicotinate, Nicomol, niceritorol.

The other antihypercholesterolemic drugs include, cholestyramine, soysterol, colestimide.

Non-steroidal anti-inflammatory drugs include, for example, sasapyrine, sodium salicylate, aspirin, aspirin dialuminate, diflunisal, indomethacin, suprofen, ufenamate, dimethylisopropylazulene, bufexamac, felbinac, dichlofenac, tolmetin sodium, clinoril, fenbufen, nabumetone, proglumetacin, indometacin farnesil, acemetacin, proglumetacin maleate, amfenac sodium, mofezolac, etodolac, ibuprofen, ibuprofenpiconol, naproxen, flurbiprofen, flurbiprofen axetil, ketoprofen, phenoprofen calcium, tiaprofenic acid, oxaprozin, pranoprofen, loxoprofen sodium, alminoprofen, zaltoprofen, mefenamic acid, aluminum mefenamate, tolfenamic acid, floctafenine, ketophenylbutazon, oxyfenbutazon, piroxicam, tenoxicam, ampiroxicam, napageln ointment, epirizole, tiaramide hydrochloride, tinoridine hydrochloride, emorfazone, sulpyrine, migrenin, saridon, cedes G, amipylo-N, sorbon, pyrine cold preparation, acetoaminofen, fenacetin, dimetotiazine mesilate, simetride, non-pyrine cold preparation, etc.

Disease-modifying antirheumatic drugs (slow-acting antirheumatic drugs) include, for example, gold preparation (e.g. aureus thioglucose, aureus thiomalate sodium), auranofin, actarit, D-penicillamine preparations, lobenzarit disodium, bucillamine, hydroxychloroquine sulphate, salazosulfapyridine, etc.

Cartilage-protecting agents include, for example, sodium hyaluronate, glucosamine, chondroitin sulfate, glycosaminoglycan sulfate, etc.

Prostaglandin synthase inhibitors include, for example, salazosulfapyridine, mesalazine, osalazine, 4-aminosalicylic acid, JTE-522, auranofin, carprofen, diphenpyramide, flunoxaprofen, flurbiprofen, indomethacin, ketoprofen, lornoxicam, loxoprofen, meloxicam, oxaprozin, parsalmide, piproxen, piroxicam, piroxicam betadex, piroxicam cinnamate, tropine indomethacinate, zaltoprofen, pranoprofen, etc.

There is no limitation for the ratio by weight of the compound of formula (I) to other agents.

With regard to other agents, two or more members of any agent may be administered in combination.

Such other agents which supplement and/or reinforce the preventive and/or treating effect of the EDG-2 antagonist include not only those which have been found on the basis of the above-mentioned mechanism but also those which will be found in future.

The EDG-2 antagonist, a combination of the EDG-2 antagonists and other drugs are generally administered systemically or topically and orally or parenterally when used for the above objects.

The dosages are determined depending on age, body weight, symptom, therapeutic effect, administration route, duration of the treatment and the like. Generally, 0.01 mg to 1000 mg, preferably 0.1 mg to 500 mg, more preferably 0.1 mg to 300 mg per adult is orally administered once to several times per day, or 0.01 mg to 500 mg, preferably. 0.1 mg to 100 mg, more preferably 0.1 mg to 50 mg per adult is parenterally administered once to several times per day, or continuously administered from vein for 1 to 24 hours per day.

Since the dose changes depending on various conditions as described above, there are cases in which doses lower than or greater than the above ranges may be used.

The EDG-2 antagonist and concomitant agent of the EDG-2 antagonist and other agents may be administered in the form of solid compositions, liquid compositions and other compositions for oral administration, and injections, external medicine (e.g. endermic liniments, transdermal agents, transmucomembranous agents, etc.), suppositories, eye lotions, inhalants and the like for parenteral administration.

Solid compositions for oral administration include tablets, pills, capsules, dispersible powders, granules and the like.

Capsules include hard capsules and soft capsules.

In such solid compositions, one or more active compound(s) are mixed with one or more of excipients (lactose, mannitol, glucose, microcrystalline cellulose, starch, etc.), binding agent (hydroxypropylcellulose, polyvinylpyrrolidone, magnesium aluminometasilicate, etc.), disintegrating agent (calcium glycolate cellulose, etc.), lubricating agents (magnesium stearate etc.), stabilizer, agents to assist resolution (glutamic acid, aspartic acid, etc.), etc. and formulated according to usual methods. If necessary, the tablets or pills may be coated with film of gastric- or enteric-coating agents such as sugar, gelatin, hydroxypropyl cellulose and hydroxypropyl cellulose phthalate, or be coated with two or more films. Furthermore, capsules of absorbable materials such as gelatin are included.

Liquid compositions for oral administration include pharmaceutically acceptable aqueous solutions, suspensions, emulsions, syrups, elixirs and the like. In such liquid compositions, one or more active compound(s) are dissolved, suspended or emulsified in an inert diluent commonly used (e.g., purified water, ethanol or a mixture thereof, etc.). Furthermore, such liquid compositions may also contain auxiliary materials such as wetting agents, suspending agents, emulsifying agents, sweetening agents, flavoring agents, aromatic agents, preserving agents, buffering agents, etc.

Other compositions of external medicines for parenteral administration include ointments, gels, creams, poultices, adhesive preparations, liniments, air sprays, inhalants, sprays, aerosols, eye drops, nasal preparations, etc. These include one or more of active substance and it may be formulated by known methods or usually used prescriptions.

Ointment compositions may be prepared by known or usually used prescriptions, for example, by levigating or fusing using one or more active substance as a base. Ointment base is selected from known or usually used ones, for example, higher fatty acid or higher fatty acid ester (adipic acid, myristic acid, palmitic acid, stearic acid, oleic acid, adipic acid ester, myristic acid ester, palmitic acid ester, stearic acid ester, oleic acid ester, wax (bees wax, whale wax, ceresin wax, etc.), surfactants (polyoxyethylenealkylether phosphate, etc.), higher alcohol (cetanol, stearylalcohol, cetostearylalcohol, etc.), silicon oil (dimethylpolysiloxane etc.), hydrocarbons (hydrophilic petrolatum, white petrolatum, purified lanoline, liquid paraffin, etc.), glycols (ethyleneglycol, diethyleneglycol, propyleneglycol, polyethyleneglycol, macrogol, etc.), salad oil (castor oil, olive oil, sesame oil, terepin oil, etc.), animal oil (mink oil, vitellus oil, squalene, squalene, etc.), water, absorption promoter, irritation preventives. And ointments may further include moisturizing agent, preserving agents, stabilizing agents, antioxidants, aromatic agents, etc.

Gels may be prepared by known or usually used prescriptions, for example, one or more of active substance is fused. Gel bases are selected from known or usually used ones, for example, one or more selected from lower alcohol (ethanol, isopropylalcohol, etc.), gelling agents (carboxymethylcellulose, hydroxyethylcellulose, hydroxypropylcellulose, ethylcellulose, etc.), neutralizing agents (triethanolamine, diisopropanolamine, etc.), surfactants (polyethyleneglycol monostearate, etc.), gums, water, absorption promoters, irritation preventives. It may further contain preserving agents, antioxidants, aromatic agents, etc.

Cream compositions may be manufactured by known or usually used prescriptions. For example, they may be prepared by fusing or emulsifying one or more active substance is in a base. Cream bases are selected from known or usually used ones, for example, one or more selected from higher fatty acid ester, lower alcohol, hydrocarbon, multiple alcohol (propyleneglycol, 1,3-butyleneglycol, etc.), higher alcohol (2-hexyldecanol, cetanol, etc.), emulsifying agents (polyoxyethylenealkyl ether, fatty acid ester, etc.), water, absorption promoter, irritation preventives, etc.

Poultices may be manufactured by known or usually used prescriptions. For example, one or more active substance is fused in a base, and it is beat out and coated over support medium to give a paste, which is beat out and coated on the support medium. The base for poultices are selected from known or usually used ones. For example, one or a mixture of more than one selected from thickening agents (polyacrylic acid, polyvinylpyrrolidone, Arabia gum, starch, methylcellulose, etc.), wetting agents (urea, glycerin, propyleneglycol, etc.), bilking agents (kaolin, zinc oxide, talc, calcium, magnesium, etc.), water, solubilizing agents, agents to assist adhesion, irritation preventives. And they may further include preserving agents, antioxidants, aromatic agents, etc.

Adhesive preparations may be manufactured by known or usually used prescriptions. For example, one or more active substance is fused in a base, and it is beat out and coated over support medium. The base for adhesive preparations are selected from known or usually used ones, for example, one or more selected from macromolecule base, grease, higher fatty acid, agents to assist adhesion, irritation preventives. And they may further include preserving agents, antioxidants, aromatic agents, etc.

Liniments may be manufactured by known or usually used prescriptions. For example, liniments may be prepared by dissolving one or more of active ingredients in water, alcohol (ethanol, polyethyleneglycol, etc.), higher fatty acid, glycerine, soaps, emulsifiers, suspenders, etc. They may also include preserving agents, antioxidants, aromatic agents, etc.

Air sprays, inhalants and sprays include, stabilizing agents such as sodium hydrogen sulfate, buffering agents to give isotonicity, isotonic solutions such as sodium chloride, sodium citrate or citric acid, except inert diluents. The processes for preparing sprays are described in U.S. Pat. Nos. 2,868,691 and 3,095,355.

Other compositions for oral administration include sprays containing one or more active compound(s) which are prepared by known methods. Such compositions may contain stabilizing agents such as sodium hydrogen sulfate, buffering agents to give isotonicity, isotonic solutions such as sodium chloride, sodium citrate or citric acid, in addition to inert diluents. The processes for preparing spray preparations are described in U.S. Pat. Nos. 2,868,691 and 3,095,355.

Injections for parenteral administration include solvents, suspensions, emulsions and solid composition for injection dissolved when used. Injections may be used by dissolving, suspending or emulsifying one or more active substance in a solvent. Solvents include, for example, distilled water for injection, physiological saline, vegetable oil, alcohols (e.g. propyleneglycol, polyethyleneglycol, ethanol, etc.), and combinations thereof. The injections may further include stabilizing agents, solubilizing agents (e.g. glutamic acid, aspartic acid, polysorbate 80 (registered trademark), suspending agents, emulsifying agents, soothing agents, buffering agents, preserving agents, etc. They are sterilized in the final step or prepared by aseptic manipulation. Or sterile solid composition, for example, freeze-dried product is manufactured and it may be sterilized or dissolved in sterile purified water or other solvents before use.

Eye drops for parenteral administration include, for example, eye drops, suspension eye drops, emulsion eye drops, eye drops which is dissolved in use and eye ointments.

Other compositions for oral administration include sprays containing one or more active compound(s) which are prepared by known methods. Such compositions may contain stabilizing agents such as sodium hydrogen sulfate, buffering agents to give isotonicity, isotonic solutions such as sodium chloride, sodium citrate or citric acid, in addition to inert diluents. The processes for preparing sprays are described in U.S. Pat. Nos. 2,868,691 and 3,095,355.

Injections for parenteral administration in the present invention include sterile aqueous or non-aqueous solutions, suspensions and emulsions. Aqueous solutions and suspensions include distilled water for injection and physiological saline. Non-aqueous solutions and suspensions include propylene glycol, polyethylene glycol, plant oil such as olive oil, alcohols such as ethanol, POLYSORBATE80 (registered trade mark), and the like. Sterile aqueous and non-aqueous solutions, suspensions and emulsions may be used as a mixture. Such compositions may further contain preserving agents, wetting agents, emulsifying agents, dispersing agents, stabilizing agents (e.g., lactose), auxiliary agents such as solubilizing auxiliary agents (e.g., glutamic acid, aspartic acid). They may be sterilized by filtration through a bacteria-retaining filter, incorporation of a sterilizing agent or irradiation. For example, they may also be manufactured in the form of sterile solid compositions which can be dissolved in sterile water or other sterile diluents for injection of the freeze-dried product before use.

The dosage form of eye-drops for parenteral administration include eye lotions, suspending eye lotions, emulsion eye lotions, eye lotions dissolved when used, and eye ointments.

These eye drops are manufactured according to known methods. For example, the eye drops are used by dissolving, suspending or emulsifying one or more active substance(s) in a solvent. Solvents used for eye drops include, for example, sterile purified water, physiological saline, other aqueous solvents or inaqueous solvents for injection (e.g. vegetable oil etc.), and combination thereof. Eye drops may further include, if necessary, isotonizing agents (e.g., sodium chloride, concentrated glycerine, etc.), buffering agents (e.g., sodium phosphate, sodium acetate, etc.), surfactants (e.g., POLYSORBATE80 (product name), polyoxyl 40 stearate, polyoxyethylene hydrogenated castor oil, etc.), stabilizing agents (e.g. sodium citrate, sodium edetate, etc.), antiseptic agents (e.g., benzalkonium chloride, paraben, etc.), and the like. They are sterilized in the final step or prepared by aseptic manipulation. Or sterile solid composition, for example, freeze-dried product is manufactured and it may be sterilized or dissolved in sterile purified water or other solvents before use.

The inhalants for parenteral administration include aerosols, powders for inhalation, and liquids for inhalation, and the liquid for inhalation may be in the form which is dissolved or suspended in water or an appropriate medium when used.

These inhalations can be produced according to known methods.

For example, the liquids for inhalation can be prepared, if necessary, by appropriately selecting preserving agents (e.g. benzalkonium chloride, paraben, etc.), coloring agents, buffering agents (e.g. sodium phosphate, sodium acetate, etc.), isotonizing agents (e.g. sodium chloride, concentrated glycerine, etc.), thickeners (e.g. carboxyvinyl polymer, etc.), absorption promoters, and the like.

The powders for inhalation can be prepared, if necessary, by appropriately selecting lubricants (e.g. stearic acid, salts thereof, etc.), binding agents (e.g. starch, dextrin, etc.), excipients (e.g. lactose, cellulose, etc.), coloring agents, preserving agents (e.g. benzalkonium chloride, paraben, etc.), absorption promoters, and the like.

When the liquids for inhalation are administered, a sprayer (e.g., atomizer, nebulizer) is usually used. When the powders for inhalation are used, an inhalation administration apparatus for powder agents is usually used.

Other compositions for parenteral administration include suppositories for intrarectal administration, pessaries for intravaginal administration and the like containing one or more active compound(s) which can be prepared by known methods.

The inhalants for parenteral administration include aerosols, powders for inhalation, and liquids for inhalation, and the liquid for inhalation may be in the form which is dissolved or suspended in water or an appropriate medium when used.

These inhalations can be produced according to known methods.

For example, the liquids for inhalation can be prepared, if necessary, by appropriately selecting preserving agents (e.g. benzalkonium chloride, paraben, etc.), coloring agents, buffering agents (e.g. sodium phosphate, sodium acetate, etc.), isotonizing agents (e.g. sodium chloride, concentrated glycerine, etc.), thickeners (e.g. carboxyvinyl polymer, etc.), absorbefacients, and the like.

The powders for inhalation can be prepared, if necessary, by appropriately selecting lubricants (e.g. stearic acid, salts thereof, etc.), binding agents (e.g. starch, dextrin, etc.), excipients (e.g. lactose, cellulose, etc.), coloring agents, preserving agents (e.g. benzalkonium chloride, paraben, etc.), absorbefacients, and the like.

When the liquids for inhalation are administered, a sprayer (e.g. atomizer, nebulizer) is usually used. When the powders for inhalation are used, an inhalation administration apparatus for powder agents is usually used.

Other compositions for parenteral administration include liquids for external use, endemic liniments, ointments, suppositories for intrarectal administration, pessaries for intravaginal administration and the like containing one or more active compound(s) which can be prepared by known methods.

The doses to be administered are determined depending upon, for example, age, body weight, symptom, the desired therapeutic effect, the route of administration, and the duration of the treatment. In the human adult, the doses per person are generally from 1 mg to 1000 mg, by oral administration, up to several times per day, and from 1 mg to 100 mg, by parenteral administration (preferably intravenous administration), up to several times per day, or continuous administration for from 1 to 24 hours per day from vein.

BEST MODE FOR CARRYING OUT THE INVENTION

Figure 1:
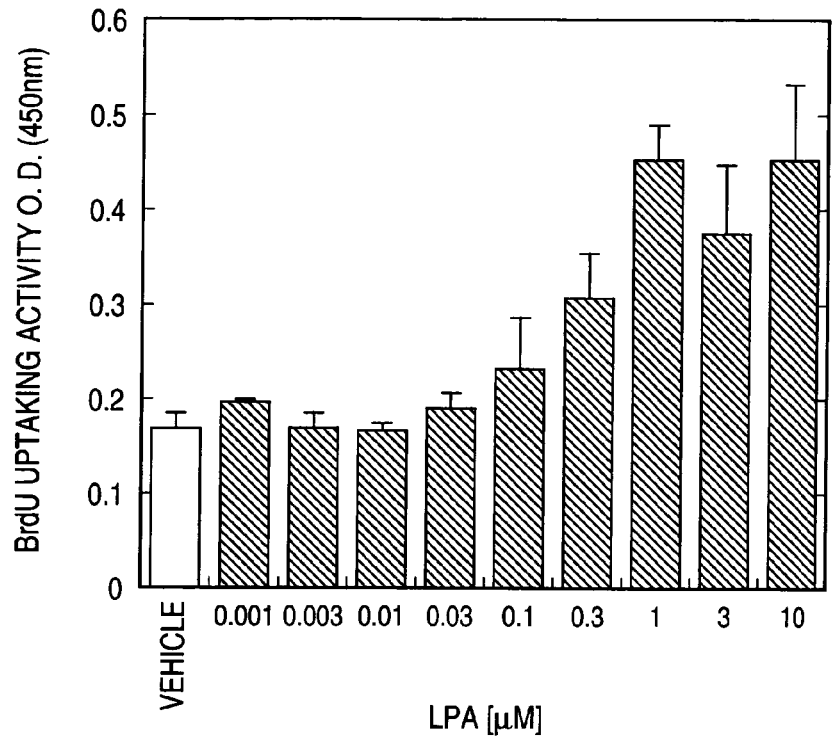
FIG. 1 shows the proliferation effect of normal human prostate stroma cells by LPA.

The present invention is explained below in detail based on the following reference examples, preparation examples and examples; but the present invention is not limited thereto.

The solvents in the parentheses show the developing or eluting solvents and the ratios of the solvents used are by volume in chromatographic separations or TLC. The solvents in the parentheses in NMR show the solvents for measurement.

The rules for naming the compound described in the present specification are explained as follows.

Naming used in the present specification is carried out according to IIPAC rules or ACD/Name (registered trademark)(ver. 6.00, Advanced Chemistry Development Inc.), which is a computerized system generating a name according to IUPAC rules.

REFERENCE EXAMPLE 1

3-(2-(4-ethoxyphenyl)ethyl)aminopropanoic acidethyl ester hydrochloride 4-ethoxyphenethylamine (2.2 g) and ethyl acrylate (1.5 g) were dissolved in ethanol (25 ml) and the mixture was stirred for 3 days at room temperature. Ethanol was evaporated under reduced pressure and thus given residue was added 4N hydrochloric acid-ethyl acetate. Under reduced pressure the solvent was evaporated and thus given residue was washed with diisopropyl ether to give the title compound (4.0 g) having the following physical data.

TLC:Rf 0.89 (chloroform: methanol=9:1);

NMR (DMSO-$d_6$): δ 9.10 (brs, 2H), 7.16 (d, J=8.7 Hz, 2H), 6.87 (d, J=8.7Hz, 2H), 4.11 (q, J=7.2 Hz, 2H), 3.99 (q, J=7.2 Hz, 2H), 3.40-3.00 (m, 4H), 3.00-2.85 (m, 2H), 2.79 (t, J=7.5 Hz, 2H), 1.31 (t, J=7.2 Hz, 3H), 1.21 (t, J=7.2Hz, 3H).

REFERENCE EXAMPLE 2

3-(N-((2-(2-carboxyphenyl)phenyl)carbonyl)-N-(2-(4-ethoxyphenyl)ethyl)amino)propanoic acidethyl ester The compound prepared in reference example 1 (600 mg), diphenic anhydride (538 mg) and triethylamine (0.85 ml) were dissolved in methylene chloride (10 ml) and the mixture was stirred overnight at room temperature. The reaction mixture was poured into a mixture of ethyl acetate and 1N hydrochloric acid, and the aqueous layer was extracted with ethyl acetate. The combined organic layer was washed with a saturated aqueous solution of sodium bicarbonate and brine successively and dried over anhydrous sodium sulfate. The solvent was evaporated to give the title compound (837 mg) having the following physical data.

TLC:Rf 0.50 (chloroform:methanol=9:1);

NMR (DMSO-$d_6$): δ 7.90-7.15 (m, 8H), 7.00-6.70 (m, 4H), 4.00-3.90 (m, 4H), 3.80-3.00 (m, 4H), 2.60-2.00 (m, 4H), 1.35-1.05 (m, 6H).

PREPARATION EXAMPLE 1

3-(N-((2-(2-((pyridin-3-ylmethylamino)carbonyl)phenyl) phenyl)carbonyl)-N-(2-(4-ethoxyphenyl)ethyl)amino)propanoic acid ethyl ester The compound prepared in reference example 2 (150 mg), 3-picolylamine (50 mg) and 1-ethyl-3-[3-(dimethylamino) propyl]carbodiimide hydrochloride (180 mg) were dissolved in methylene chloride (5 ml) and the mixture was stirred overnight at room temperature. The reaction mixture was poured into a mixture of ethyl acetate and 1N hydrochloric acid and the aqueous layer was extracted with ethyl acetate. Combined organic layer was washed with brine and dried over anhydrous magnesium sulfate. The solvent was evaporated and the residue was purified by column chromatography on silica gel (chloroform:ethyl acetate=1:2) to give the compound (147 mg) having the following physical data.

TLC:Rf 0.20 (chloroform:ethyl acetate=3:2);

NMR (DMSO-$d_6$): δ 9.00-8.10 (m, 2H), 7.60-6.75 (m, 17H), 4.40-3.90 (m, 4H), 3.80-3.10 (m, 4H), 2.80-2.05 (m, 4H), 1.40-1.30 (m, 3H), 1.20-1.10 (m, 3H).

PREPARATION EXAMPLE 2

N-[2-(4-ethoxyphenyl)ethyl]-N-[(2'-{[(pyridin-3-ylmethyl) amino]carbonyl}biphenyl-2-yl)carbonyl]-β-alanine (compound (35))

The compound prepared in preparation example 1 (110 mg) and 1N aqueous solution of sodium hydroxide (0.5 ml) were dissolved in a mixture of ethanol (1 ml) and tetrahydrofuran (2 ml) and the mixture was stirred for 2 hours at room temperature. The reaction mixture was poured into a mixture of ethyl acetate and 1N hydrochloric acid and the aqueous layer was extracted with ethyl acetate. The combined organic layer was washed with brine and dried over anhydrous magnesium sulfate. The solvent was evaporated to give the compound (77 mg) having the following physical data.

TLC:Rf 0.36 (chloroform:methanol=9:1);

NMR (DMSO-$d_6$): δ 9.00-8.30 (m, 2H), 7.60-6.70 (m, 15H), 4.60-4.10 (m, 2H), 4.00-3.90 (m, 2H), 3.90-3.00 (m, 4H), 2.80-2.65 (m, 2H), 2.20-2.00 (m, 2H), 1.40-1.20 (m, 3H).

REFERENCE EXAMPLE 3

Acrylic acid Ester Supported by Solid Phase

Under atmosphere of argon, to methylene chloride (198 ml) were added Lantern PS-Wang (registered trademark) (Mimotopes, code No. SPPSLHHP) (16.0 mcmol/Lantern, 1000 portions) and thereto were added N,N-diisopropylethylamine (77.9 ml) and acryloyl chloride (24.4 ml) at −78° C. The reaction mixture was stirred for 15 hours at room temperature. The solid phase carrier was filtrated from the reaction mixture and it was washed with methelene chloride (150 ml×5 times) and air-dried to give acrylic acid ester supported by the solid phase.

REFERENCE EXAMPLE 4

3-benzylaminopropanoic acid Ester Supported by Solid Phase

To a solution of benzylamine in N-methyl-2-pyrrolidone (1.0M, 15 ml) was added the compound prepared in reference example 3 (45 portions, 0.72 mmol) and the mixture was stirred for 16 hours at room temperature. The solid phase carrier was filtrated from the reaction mixture and washed with N-methyl-2-pyrrolidone (20 ml×4) to give 3-benzylaminopropanoic acid ester supported by the solid phase.

REFERENCE EXAMPLE 5

3-(N-((2-(2-carboxyphenyl)phenyl)carbonyl)-N-(benzyl) amino)propanoic acid ester Supported by Solid Phase To N-methyl-2-pyrrolidone (500 ml) was added the compound prepared in reference example 4 (1350 portions, 21.6 mmol) and to the mixture was added diphenoic anhydride (48.4 g) and the reaction mixture was stirred for 60 hours at 50° C. The solid phase carrier was filtrated from the reaction mixture and washed with N,N-dimethylformamide (500 ml×4) and methylene chloride (500 ml×3). The given solid carrier was air-dried to give 3-(N-((2-(2-carboxyphenyl) phenyl)carbonyl)-N-(benzyl)amino)propanoic acid ester supported by the solid phase.

REFERENCE EXAMPLE 6

3-(N-((2-(2-((3-methylbenzylamino)carbonyl)phenyl)phenyl)carbonyl)-N-(benzyl)amino)propanoic acid Ester Supported by Solid Phase To N,N-dimethylformamide (10 ml) was added the compound prepared in reference example 5 (30 portions, 0.48 mmol) and thereto were added 3-methylbenzylamine (2.40 mmol), 1-hydroxybenztriazole monohydrate (368 mg) and N,N-diisopropylcarbodiimide (0.376 ml). The reaction mixture was stirred for 16 hours at room temperature. From the reaction mixture was solid carried collected by filtration and washed with N,N-dimethylformamide (10 ml×3) and methylene chloride (10 ml×3). The given solid carrier was air-dried to give 3-(N-((2-(2-((3-methylbenzylamino)carbonyl)phenyl)phenyl)carbonyl)-N-(benzyl)amino)propanoic acid ester supported by the solid phase.

PREPARATION EXAMPLE 3

3-(N-((2-(2-((3-methylbenzylamino)carbonyl)phenyl)phenyl)carbonyl)-N-(benzyl)amino)propanoic acid To trifluoroacetic acid (0.5 ml) was added the compound prepared in reference example 6 (1 portion, 0.016 mmol) and the mixture was treated for 1 hour at room temperature. The solid carried was removed and washed with trifluoroacetic acid (0.5 ml). The combined washed liquors were concentrated under reduced pressure to give the compound of the present invention having the following physical data. The conditions for analysis using high-performance liquid chromatography (HPLC) are shown below.

Column: Xterra(registered trademark) MS $C_{18}$, 4.6×50 mm I.D., 5 μm, 100 Å
Rate of Flow: 3 mL/min
Solvents
liquid A: 0.1% aqueous solution of trifluoroacetic acid
liquid B: 0.1% trifluoroacetic acid in acetonitrile After starting the measurement the ratio of liquid A and liquid B was fixed at 95/5. Then in 2.5 minutes the ratio of liquid A and liquid B was changed linearly into 0/100. And for 0.5 minutes the ratio of liquid A and liquid B was fixed at 0/100. In 0.01 minutes the ratio of liquid A and liquid B was changed linearly into 95/5.

HPLC retention time: 3.84 minutes;

MASS data (ESI, Pos., 20V): 507 $(M+H)^+$.

PREPARATION EXAMPLE 3(1) to (34)

By the same procedure as described in reference example 4 → reference example 5 using a corresponding amine in place of benzylamine, and then by the same procedure as described in reference example 6 → preparation example 3 using a corresponding amine in place of 3-methylbenzylamine, the following compounds were given.

HPLC Condition

Column: Xterra (Registered Trademark) MS $C_{18}$, 4.6×50 mm. I.D., 5 μm; 100 Å

Flow Rate: 3 mL/min

Solvent liquid A: 0.1% aqueous solution of trifluoroacetic acid liquid B: 0.1% solution of trifluoroacetic acid in acetonitrile After starting the measurement the ratio of liquid A and liquid B was fixed at 95/5. Then in 2.5 minutes the ratio of liquid A and liquid B was changed linearly into 0/100. And for 0.5 minutes the ratio of liquid A and liquid B was fixed at 0/100. In 0.01 minutes the ratio of liquid A and liquid B was changed linearly into 95/5.

PREPARATION EXAMPLE 3(1)

3-(N-((2-(2-((4-chlorobenzylamino)carbonyl)phenyl)phenyl)carbonyl)-N-(2-(2-methoxyphenyl)ethyl)amino)propanoic acid (compound (1))

HPLC retention time: 3.99 minutes;

MASS data (ESI, Pos., 20V):571 $(M+H)^+$.

PREPARATION EXAMPLE 3(2)

3-(N-((2-(2-((4-chlorobenzylamino)carbonyl)phenyl)phenyl)carbonyl)-N-(2-(2,4-dichlorophenyl)ethyl)amino)propanoic acid (compound (2))

HPLC retention time: 4.17 minutes;

MASS data (ESI, Pos., 20V):609 $(M+H)^+$.

PREPARATION EXAMPLE 3(3)

3-(N-((2-(2-(((1R)-1-(4-methylphenyl)ethylamino)carbonyl)phenyl)phenyl)carbonyl)-N-(2-(2,4-dichlorophenyl) ethyl)amino)propanoic acid (compound (3))

HPLC retention time: 4.22 minutes;

MASS data (ESI, Pos., 20V):603 $(M+H)^+$.

PREPARATION EXAMPLE 3(4)

3-(N-((2-(2-((pyridin-3-ylmethylamino)carbonyl)phenyl)phenyl)carbonyl)-N-(2-(4-ethoxyphenyl)ethyl)amino)propanoic acid (compound (4))

HPLC retention time: 3.25 minutes;

MASS data (ESI, Pos., 20V):552 (M+H)$^+$.

PREPARATION EXAMPLE 3(5)

3-(N-((2-(2-((4-chlorobenzylamino)carbonyl)phenyl)phenyl)carbonyl)-N-(2-(4-ethoxyphenyl)ethyl)amino)propanoic acid (compound (5))

HPLC retention time: 4.02 minutes;

MASS data (ESI, Pos., 20V):585 (M+H)$^+$.

PREPARATION EXAMPLE 3(6)

3-(N-((2-(2-((4-chlorobenzylamino)carbonyl)phenyl)phenyl)carbonyl)-N-(2-(2-methylphenyl)ethyl)amino)propanoic acid (compound (6))

HPLC retention time: 4.02 minutes;

MASS data (ESI, Pos., 20V):555 (M+H)$^+$.

PREPARATION EXAMPLE 3(7)

3-(N-((2-(2-((pyridin-3-ylmethylamino)carbonyl)phenyl)phenyl)carbonyl)-N-(2-(2,5-dimethoxyphenyl)ethyl)amino)propanoic acid (compound (7))

HPLC retention time: 3.20 minutes;

MASS data (ESI, Pos., 20V):568 (M+H)$^+$.

PREPARATION EXAMPLE 3(8)

3-(N-((2-(2-((4-chlorobenzylamino)carbonyl)phenyl)phenyl)carbonyl)-N-(2-(2,5-dimethoxyphenyl)ethyl)amino)propanoic acid (compound (8))

HPLC retention time: 3.97 minutes;

MASS data (ESI, Pos., 20V):601 (M+H)$^+$.

PREPARATION EXAMPLE 3(9)

3-(N-((2-(2-((4-methoxybenzylamino)carbonyl)phenyl)phenyl)carbonyl)-N-(2-(2,5-dimethoxyphenyl)ethyl)amino)propanoic acid (compound (9))

HPLC retention time: 3.80 minutes;

MASS data (ESI, Pos., 20V):597 (M+H)$^+$.

PREPARATION EXAMPLE 3(10)

3-(N-((2-(2-((4-methylbenzylamino)carbonyl)phenyl)phenyl)carbonyl)-N-(2-(2,5-dimethoxyphenyl)ethyl)amino)propanoic acid (compound (10))

HPLC retention time: 3.91 minutes;

MASS data (ESI, Pos., 20V):581 (M+H)$^+$.

PREPARATION EXAMPLE 3(11)

3-(N-((2-(2-((N-(1-methylethyl)-N-benzylamino)carbonyl)phenyl)phenyl)carbonyl)-N-(2-(2,5-dimethoxyphenyl)ethyl)amino)propanoic acid (compound (11))

HPLC retention time: 3.97 minutes;

MASS data (ESI, Pos., 20V):609 (M+H)$^+$.

PREPARATION EXAMPLE 3(12)

3-(N-((2-(2-((4-(tert-butyl)benzylamino)carbonyl)phenyl)phenyl)carbonyl)-N-(2-(2,5-dimethoxyphenyl)ethyl)amino)propanoic acid (compound (12))

HPLC retention time: 4.13 minutes;

MASS data (ESI, Pos., 20V):623 (M+H)$^+$.

PREPARATION EXAMPLE 3(13)

3-(N-((2-(2-((3-fluorobenzylamino)carbonyl)phenyl)phenyl)carbonyl)-N-(2-(2,5-dimethoxyphenyl)ethyl)amino)propanoic acid (compound (13))

HPLC retention time: 3.84 minutes;

MASS data (ESI, Pos., 20V):585 (M+H)$^+$.

PREPARATION EXAMPLE 3(14)

3-(N-((2-(2-((2-chlorobenzylamino)carbonyl)phenyl)phenyl)carbonyl)-N-(2-(2,5-dimethoxyphenyl)ethyl)amino)propanoic acid (compound (14))

HPLC retention time: 3.93 minutes;

MASS data (ESI, Pos., 20V):601 (M+H)$^+$.

PREPARATION EXAMPLE 3(15)

3-(N-((2-(2-((4-fluorobenzylamino)carbonyl)phenyl)phenyl)carbonyl)-N-(2-(2,5-dimethoxyphenyl)ethyl)amino)propanoic acid (compound (15))

HPLC retention time: 3.84 minutes;

MASS data (ESI, Pos., 20V):585 (M+H)$^+$.

PREPARATION EXAMPLE 3(16)

3-(N-((2-(2-((3-chlorobenzylamino)carbonyl)phenyl)phenyl)carbonyl)-N-(2-(2,5-dimethoxyphenyl)ethyl)amino)propanoic acid (compound (16))

HPLC retention time: 3.95 minutes;

MASS data (ESI, Pos., 20V):601 (M+H)$^+$.

PREPARATION EXAMPLE 3(17)

3-(N-((2-(2-(((1R)-1-(4-methylphenyl)ethylamino)carbonyl)phenyl)phenyl)carbonyl)-N-(2-(2,5-dimethoxyphenyl)ethyl)amino)propanoic acid (compound (17))

HPLC retention time: 3.97 minutes;

MASS data (ESI, Pos., 20V):595 (M+H)$^+$.

PREPARATION EXAMPLE 3(18)

3-(N-((2-(2-((1-(4-fluorophenyl)ethylamino)carbonyl)phenyl)phenyl)carbonyl)-N-(2-(2,5-dimethoxyphenyl)ethyl)amino)propanoic acid (compound (18))

HPLC retention time: 3.93 minutes;

MASS data (ESI, Pos., 20V):599 (M+H)$^+$.

PREPARATION EXAMPLE 3(19)

3-(N-((2-(2-((pyridin-3-ylmethylamino)carbonyl)phenyl)phenyl)carbonyl)-N-(2-(3-ethoxy-4-methoxyphenyl)ethyl)amino)propanoic acid (compound (19))

HPLC retention time: 3.14 minutes;

MASS data (ESI, Pos., 20V):582 (M+H)$^+$.

PREPARATION EXAMPLE 3(20)

3-(N-((2-(2-((pyridin-3-ylmethylamino)carbonyl)phenyl)phenyl)carbonyl)-N-(2-(3-methoxy-4-ethoxyphenyl)ethyl)amino)propanoic acid (compound (20))

HPLC retention time: 3.16 minutes;

MASS data (ESI, Pos., 20V):582 (M+H)$^+$.

PREPARATION EXAMPLE 3(21)

3-(N-((2-(2-((4-chlorobenzylamino)carbonyl)phenyl)phenyl)carbonyl)-N-(2-(3-methoxy-4-ethoxyphenyl)ethyl)amino)propanoic acid (compound (21))

HPLC retention time: 3.89 minutes;

MASS data (ESI, Pos., 20V):615 (M+H)$^+$.

PREPARATION EXAMPLE 3(22)

3-(N-((2-(2-((4-methoxybenzylamino)carbonyl)phenyl)phenyl)carbonyl)-N-(2-(3-methoxy-4-ethoxyphenyl)ethyl)amino)propanoic acid (compound (22))

HPLC retention time: 3.75 minutes;

MASS data (ESI, Pos., 20V):611 (M+H)$^+$.

PREPARATION EXAMPLE 3(23)

3-(N-((2-(2-((4-methylbenzylamino)carbonyl)phenyl)phenyl)carbonyl)-N-(2-(3-methoxy-4-ethoxyphenyl)ethyl)amino)propanoic acid (compound (23))

HPLC retention time: 3.86 minutes;

MASS data (ESI, Pos., 20V):595 (M+H)$^+$.

PREPARATION EXAMPLE 3(24)

3-(N-((2-(2-((4-fluobenzylamino)carbonyl)phenyl)phenyl)carbonyl)-N-(2-(3-methoxy-4-ethoxyphenyl)ethyl)amino)propanoic acid (compound (24))

HPLC retention time: 3.78 minutes;

MASS data (ESI, Pos., 20V):599 (M+H)$^+$.

PREPARATION EXAMPLE 3(25))

3-(N-((2-(2-(((1R)-1-(4-methylphenyl)ethylamino)carbonyl)phenyl)phenyl)carbonyl)-N-(2-(3-methoxy-4-ethoxyphenyl)ethyl)amino)propanoic acid (compound (25))

HPLC retention time: 3.91 minutes;

MASS data (ESI, Pos., 20V):609 (M+H)$^+$.

PREPARATION EXAMPLE 3(26)

3-(N-((2-(2-((1-(4-fluorophenyl)ethylamino)carbonyl)phenyl)phenyl)carbonyl)-N-(2-(3-methoxy-4-ethoxyphenyl)ethyl)amino)propanoic acid (compound (26))

HPLC retention time: 3.86 minutes;

MASS data (ESI, Pos., 20V):613 (M+H)$^+$.

PREPARATION EXAMPLE 3(27)

3-(N-((2-(2-((pyridin-3-ylmethylamino)carbonyl)phenyl)phenyl)carbonyl)-N-(2-(3,5-dimethoxyphenyl)ethyl)amino)propanoic acid (compound (27))

HPLC retention time: 3.20 minutes;

MASS data (ESI, Pos., 20V):568 (M+H)$^+$.

PREPARATION EXAMPLE 3(28)

3-(N-((2-(2-((4-chlorobenzylamino)carbonyl)phenyl)phenyl)carbonyl)-N-(2-(3,5-dimethoxyphenyl)ethyl)amino)propanoic acid (compound (28))

HPLC retention time: 3.93 minutes;

MASS data (ESI, Pos., 20V):601 (M+H)$^+$.

PREPARATION EXAMPLE 3(29)

3-(N-((2-(2-(((1R)-1-(4-methylphenyl)ethylamino)carbonyl)phenyl)phenyl)carbonyl)-N-(2-(3,5-dimethoxyphenyl)ethyl)amino)propanoic acid (compound (29))

HPLC retention time: 3.95 minutes;

MASS data (ESI, Pos., 20V):595 (M+H)$^+$.

PREPARATION EXAMPLE 3(30)

3-(N-((2-(2-((4-chlorobenzylamino)carbonyl)phenyl)phenyl)carbonyl)-N-(2-(2-ethoxyphenyl)ethyl)amino)propanoic acid (compound (30))

HPLC retention time: 4.10 minutes;

MASS data (ESI, Pos., 20V):585 (M+H)$^+$.

PREPARATION EXAMPLE 3(31)

3-(N-((2-(2-((4-chlorobenzylamino)carbonyl)phenyl)phenyl)carbyl)-N-(2-(3-ethoxyphenyl)ethyl)amino)propanoic acid (compound (31))

HPLC retention time: 4.04 minutes;

MASS data (ESI, Pos., 20V):585 (M+H)$^+$.

PREPARATION EXAMPLE 3(32)

3-(N-((2-(2-(((1S)-1-phenyl-2-hydroxyethylamino)carbonyl)phenyl)phenyl)carbonyl)-N-(benzyl)amino)propanoic acid (compound (32))

HPLC retention time: 3.58 minutes;

MASS data (ESI, Pos., 20V):523 (M+H)$^+$.

PREPARATION EXAMPLE 3(33)

3-(N-((2-(2-((4-methylbenzylamino)carbonyl)phenyl)phenyl)carbonyl)-N-(2-(4-ethoxyphenyl)ethyl)amino)propanoic acid (compound (33))

HPLC retention time: 3.99 minutes;

MASS data (ESI, Pos., 20V):565 (M+H)$^+$.

PREPARATION EXAMPLE 3(34)

3-{[(2'-{[(3-chlorobenzyl)amino]carbonyl}-2-biphenylyl)carbonyl][2-(4-ethoxy-3-methoxyphenyl)ethyl]amino}propanoic acid (compound (34))

HPLC retention time: 3.88 minutes;

MASS data (ESI, Pos., 20V):615 (M+H)$^+$.

REFERENCE EXAMPLE 7

2-(4-formylphenyl)benzoic acid methyl ester

To a solution of 4-formylphenylboric acid (6.7 g) in N,N-dimethylformamide (100 ml) were added 2-bromobenzoic acid methyl ester (6.5 g), tetrakis(triphenylphosphine)palladium [Pd(PPh$_3$)$_4$] (1.0 g) and tripotassium phosphate (23 g). The reaction mixture was stirred for 5 hours at 75° C. The reaction mixture was filtrated and concentrated. To the residue were added 1N hydrochloric acid and ethyl acetate, and the mixture was concentrated. The residue was purified by column chromatography on silica gel (hexane:ethyl acetate=9:1) to give the title compound (4.1 g) having the following physical data.

TLC:Rf 0.50(hexane:ethyl acetate=2:1);

NMR (CDCl$_3$): δ 10.07 (s, 1H), 7.96-7.89 (m, 3H), 7.63-7.34 (m, 5H), 3.66 (s, 3H).

REFERENCE EXAMPLE 8

2-(4-(3-phenylpropylaminomethyl)phenyl)benzoic acid methyl ester

To a solution of the compound prepared in reference example 7 (1.2 g) in acetic acid (4 ml)-N,N-dimethylformamide (36 ml) were added 3-phenylpropylamine (1 g) and sodium borotriacetoxyhydride (1.6 g). The reaction mixture was stirred for 2.5 hours at room temperature. To the reaction mixture were added a saturated aqueous solution of sodium bicarbonate and ethyl acetate and extracted. The extract was washed with a saturated aqueous solution of sodium bicarbonate and anhydrous sodium sulfate and concentrated to give the title compound (1.8 g) having the following physical data.

TLC:Rf 0.59(dichloromethane:methanol=9:1).

PREPARATION EXAMPLE 4

2-(4-(N-(3,4,5-trimethoxyphenylcarbonyl)-N-(3-phenylpropyl)aminomethyl)phenyl)benzoic acid methyl ester To a solution of 3,4,5-trimethoxybenzoic acid (368 mg) in N,N-dimethylformamide (10 ml) were added the compound prepared in reference example 8 (416 mg) and 1-ethyl-3-[3-(dimethylamino)propyl]carbodiimide hydrochloride (461 mg) and 1-hydroxybenzotriazole hydrate (260 mg). The reaction mixture was stirred for 4 hours at room temperature. To the reaction mixture were added 1N hydrochloric acid and ethyl acetate and extracted. The extract was washed with a saturated aqueous solution of sodium bicarbonate and brine and dried over anhydrous sodium sulfate and concentrated. The residue was purified by column chromatography on silica gel (hexane:ethyl acetate=2:1) to give the compound (273 mg) having the following physical data.

TLC:Rf 0.33 (hexane:ethyl acetate=1:1);

NMR (CDCl$_3$): δ 8.20-7.00 (m, 13H), 6.64 (s, 2H), 4.80-4:50 (m, 2H), 4.00-3.20 (m, 14H), 2.80-2.40 (m, 2H), 2.20-1.80 (m, 2H).

PREPARATION EXAMPLE 5

4'-{[(3-phenylpropyl)(3,4,5-trimethoxybenzoyl)amino]methyl}-2-biphenylcarboxylic acid (compound (39))

To a solution of the compound prepared in preparation example 4 (270 mg) in methanol (2 ml)/tetrahydrofuran (4 ml) was added 1N aqueous solution of sodium hydroxide (2 ml) and the reaction mixture was refluxed for 4 hours. To the reaction mixture were added 1N hydrochloric acid and ethyl acetate and the mixture was extracted. The extract was washed with a saturated aqueous solution of sodium bicarbonate and brine, dried over anhydrous sodium sulfate and concentrated to give the following compound (246 mg) having the following physical data.

TLC:Rf 0.56 (dichloromethane:methanol=9:1);

NMR (DMSO-d$_6$): δ 7.75-7.00 (m, 13H), 6.65 (s, 2H), 4.80-4.50 (m, 2H), 3.90-3.50 (m, 9H), 3.50-3.10 (m, 2H), 2.70-2.30 (m, 2H), 2.00-1.80 (m, 2H).

PREPARATION EXAMPLE 5(1)-5(5)

By the same procedure as described in reference example 8→Preparation Example 4→Preparation Example 5 using a corresponding aldehyde compound in place of the compound prepared in reference example 7 and a corresponding amine compound in place of 3-phenylpropylamine, the following compounds were given.

PREPARATION EXAMPLE 5(1)

(4'-{[(3-phenylpropyl)(3,4,5-trimethoxybenzoyl)amino]methyl}-2-biphenylyl)acetic acid (compound (37))

TLC:Rf 0.80 (dichloromethane:methanol=9:2);

NMR (DMSO-d$_6$): δ 7.40-6.90 (m, 15H), 6.66 (s, 2H), 4.80-4.50 (m, 2H), 3.90-3.10 (m, 11H), 2.70-2.30 (m, 2H), 2.00-1.80 (m, 2H).

PREPARATION EXAMPLE 5(2)

4'-{[(3,5-dimethoxybenzyl)(3-phenylpropyl)amino]carbonyl}-2-biphenylcarboxylic acid (compound (43))

TLC:Rf 0.57 (dichloromethane:methanol=9:1);

NMR (DMSO-d$_6$): δ 12.8 (s, 1H), 7.80-6.95 (m, 13H), 6.58-6.25 (m, 3H), 4.75-4.40 (m, 2H), 3.72 (s, 6H), 3.45-3.10 (m, 2H), 2.65-2.35 (m, 2H), 1.98-1.72 (m, 2H).

PREPARATION EXAMPLE 5(3)

4'-{[(2,5-dichlorobenzyl)(3-phenylpropyl)amino]carbonyl}-2-biphenylcarboxylic acid (compound (44))

TLC:Rf 0.53(dichloromethane:methanol=9:1);

NMR (DMSO-d$_6$): δ 12.8 (s, 1H), 7.80-7.00 (m, 16H), 4.80-4.50 (m, 2H), 3.45-3.20 (m, 2H), 2.65-2.35 (m, 2H), 1.83(m, 2H).

PREPARATION EXAMPLE 5(4)

(4-{[(3,5-dimethoxy-4-methylbenzoyl)(3-phenylpropyl)amino]methyl}phenyl)acetic acid (compound (45))

TLC:Rf 0.61 (dichloromethane:methanol=9:1);

NMR (CDCl$_3$): δ 7.34-6.90 (m, 9H), 6.52 (s, 2H), 4.70, 4.50 (s, 2H), 3.78 (s, 2H), 3.64 (s, 6H), 3.63, 3.19 (s, 2H), 2.65, 2.41 (s, 2H), 2.13-1.78 (m, 5H).

PREPARATION EXAMPLE 5(5)

2-(4-{[(3,5-dimethoxy-4-methylbenzoyl)(3-phenylpropyl) amino]methyl}phenoxy)-4-methylbenzoic acid (compound (46))

TLC:Rf 0.54(dichloromethane:methanol=9:1);

NMR (CDCl$_3$): δ 8.10 (d, J=8.1 Hz, 1H), 7.40-6.90 (m, 10H), 6.66-6.59 (m, 1H), 6.54 (s, 2H), 4.81-4.45 (m, 2H), 3.90-3.65 (m, 6H), 3.61-3.15 (m, 2H), 2.78-2.36 (m, 2H), 2.32 (s, 3H), 2.18-1.79 (m, 5H).

PREPARATION EXAMPLE 6(1)-6(5)

By the same procedure as described in reference example 8 →preparation example 4 →preparation example 5 using the compound prepared in reference example 7 or a corresponding aldehyde compound and 3-phenylpropylamine or a corresponding amine compound, the following compounds were given.

PREPARATION EXAMPLE 6(1)

2-(3,5-dimethyl-4-{[(3-phenylpropyl)(2-propylpentanoyl) amino]methyl}-1H-pyrazol-1-yl)benzoic acid·hydrochloride (compound (36))

TLC:Rf 0.35 (chloroform:methanol=10:1);

NMR (CDCl$_3$): δ 11.39 (br s, 1H), 7.89 (d, J=7.5Hz, 1H), 7.70 (t, J=7.5Hz, 1H), 7.60 (t, J=7.5Hz, 1H), 7.40 (d, J=7.5Hz, 1H), 7.37-7.10 (m, 5H), 4.46 (s, 2H), 3.11 (m, 2H), 2.56 (t, J=6.5Hz, 2H), 2.46 (m, 1H), 2.05 (s, 3H), 1.96 (s, 3H), 1.85-1.60 (m, 2H), 1.60-1.35 (m, 2H), 1.35-1.00 (m, 6H), 0.80 (t, J=7.0Hz, 6H).

PREPARATION EXAMPLE 6(2)

2-(4-{[(3,5-dimethoxybenzoyl)(3-phenylpropyl)amino] methyl}phenoxy)benzoic acid (compound (38))

TLC:Rf 0.50 (dichloromethane:methanol=9:1);

NMR (DMSO-d$_6$): δ 7.85-6.40 (m, 16H), 4.70-4.30 (m, 2H), 3.80-3.60 (m, 6H), 3.40-3.30 (m, 2H), 2.60-2.30 (m, 2H), 1.90-1.70 (m, 2H).

PREPARATION EXAMPLE 6(3)

4'-({(2,5-dichlorobenzoyl)[3-(4-methoxyphenyl)propyl] amino}methyl)-2-biphenylcarboxylic acid (compound (40))

TLC:Rf 0.50(dichloromethane:methanol=15:1);

NMR (DMSO-d$_6$): δ 7.80-7.10 (m, 12H), 6.85-6.65 (m, 3H), 5.00-4.30 (m, 2H), 3.80-3.60 (m, 3H), 3.20-2.80 (m, 2H), 2.60-2.20 (m, 2H), 2.00-1.60 (m, 2H).

PREPARATION EXAMPLE 6(4)

4'-{[(3,5-dimethoxybenzyl)(3-phenylpropanoyl)amino]methyl}-2-biphenylcarboxylic acid (compound (41))

TLC:Rf 0.42(dichloromethane:methanol=9:1);

NMR (CDCl$_3$): δ 7.93 (dd, J=6.6, 6.6 Hz, 1H), 7.55 (m, 1H), 7.42 (m, 1H), 7.35 (d, J=7.5 Hz, 1H), 7.38-7.02 (m, 9H), 6.36(s, 2H), 6.21 (d, J=2.1 Hz, 1H), 4.64 (s, 1H), 4.55 (s, 1H), 4.43 (s, 1H), 4.35 (s, 1H), 3.75 (s, 3H), 3.74 (s, 3H), 3.02 (m, 2H), 2.72 (m, 2H).

PREPARATION EXAMPLE 6(5)

4'-{[(3,5-dichlorobenzyl)(3-phenylpropanoyl)amino]methyl}-2-biphenylcarboxylic acid (compound (42))

TLC:Rf 0.44(dichloromethane:methanol=9:1);

NMR (CDCl$_3$): δ 7.94 (m, 1H), 7.54 (m, 1H), 7.45-6.90 (m, 14H), 4.62-4.25 (m, 4H), 3.10-2.98 (m, 2H), 2.80-2.56 (m, 2H).

PREPARATION EXAMPLE 7

2-[2-(3,5-dimethoxybenzoyl)1-(2-phenylethyl)-1H-benzimidazole-6-yl]benzoic acid (compound (47))

2-[1-(2-phenylethyl)-1H-benzimidazole-6-yl]benzoic acid and N,3,5-trimethoxy-N-methylbenzamide were subjected to a reaction in the presence of lithium diisopropylamide to give the compound having the following physical data.

TLC:Rf 0.35 (dichloromethane: methanol=10:1);

NMR (CDCl$_3$): δ 8.73 (d, J=1.0Hz, 1H), 8.16 (dd, J=8.5, 1.5 Hz, 1H), 7.42 (d, J=8.5Hz, 1H), 7.38 (d, J=2.5Hz, 2H), 7.24-7.08 (m, 5H), 6.74 (t, J=2.5Hz, 1H), 4.84 (t, J=7.5Hz, 2H), 3.87 (s, 6H), 3.21 (t, J=7.5Hz, 2H).

PREPARATION EXAMPLE 7(1)

2-{[2-(3,5-dimethoxybenzoyl)-1-(2-phenylethyl)-1H-benzimidazole-6-yl]oxy}benzoic acid (compound (48))

By the same procedure as described in preparation example 7 using 2-{[1-(2-phenylethyl)-1H-benzimidazole-6-yl]oxy}benzoic acid in place of 2-[1-(2-phenylethyl)-1H-benzimidazole-6-yl]benzoic acid, the following compound of the present invention.

TLC:Rf 0.42 (dichloromethane:methanol=10:1);

NMR (CDCl$_3$): δ 8.27 (dd, J=8.0, 1.5Hz, 1H), 7.92 (d, J=9.0Hz, 1H), 7.50 (m, 1H), 7.40 (d, J=2.0Hz, 2H), 7.30-7.02 (m, 7H), 6.95 (d, J=2.0Hz, 1H), 6.78 (m, 1H), 6.74 (t, J=2.0Hz, 1H), 4.76 (t, J=7.5Hz, 2H), 3.87 (s, 6H), 3.18 (t, J7.5Hz, 2H).

EXAMPLE 1

Evaluation of EDG-2 Antagonistic Activity by Monitoring the Change of Intracellular Calcium Ion Concentration Chinese hamster ovary (CHO) cells which overexpressed human EDG-2 gene were cultured in Ham's F12 medium (GIBCO BRL) containing 10% FBS (fetal bovine serum), penicillin/streptomycin and blasticidin (5 µg/ml). Thus cultured cells were incubated in Fura2 (5 µM)-AM solution [Ham's F12 medium containing FBS (10%), HEPES buffer (20 mM, pH 7.4) and probenecid (2.5 mM)]. Next, it was washed with Hanks solution containing HEPES buffer (20 mM, pH 7.4) and probenecid (2.5 mM) once, and immersed into the Hanks solution. Plates were set in fluorescent drug screening system and intracellular calcium ion concentration was measured for 30 seconds with no stimulation. Five minutes after adding thereto a compound to be tested (final concentration: 1 nM to 10 µM, in dimethylsulfoxide (DMSO) solution), the increase of intracellular calcium ion concentrations before and after the addition of LPA (excitation wave length: 340 nM and 380 nM; fluorescent wave length: 500 nm) were measured every 3 seconds. 1-oleoyl (18:1)-LPA (Sigma) or 1-linolenoyl (18:3)-LPA was used as LPA. 1-linolenoyl (18:3)-LPA was synthesized and purified by either of the following two methods.

(i) a method of synthesizing LPA from 18:3-LPC (linolenoyl (18:3)-lisophosphatidylcholine) (Sedary) using PLD (phospholipase-D) or (ii) a method synthesizing 18:3-LPC (linolenoyl (18:3)-lisophosphatidylcholine from 18:3-PC (linolenoyl (18:3)-phosphatidylcholine) (Avanti Polar Lipids) by PLA2 first, and consequently synthesizing LPA by PLD (phospholipase D).

EDG-2 antagonistic activity was calculated as an inhibition rate (%) by the following equation, wherein the peak value of LPA (final concentration: 100 nM) in a well into which DMSO containing no test compound was added was regarded as a control value (A), and in the cells treated with the test compound the difference (B) between the value before addition of the test compound and that after the addition was obtained and compared with the control value.

Inhibition rate (%)=[(A−B)/A]×100

The IC$_{50}$ value was calculated as a concentration of the compound to be tested which showed 50% inhibition.

As a result, it was confirmed that the compound of the present invention showed EDG-2 antagonistic activity. For example, 3-(N-((2-(2-((pyridin-3-ylmethylamino)carbonyl)phenyl)phenyl)carbonyl)-N-(2-(2,5-dimethoxyphenyl)ethyl)amino)propanoic acid hydrochloride[hereafter abbreviated as compound (a)], methyl 3-({4-[4-({[1-(2-chlorophenyl)ethoxy]carbonyl}amino)-3-methyl-5-isoxazolyl]benzyl}sulfanyl)propanoate [abbreviated as compound (b) hereafter], and (4'-{[(3-phenylpropyl)(3,4,5-trimethoxybenzoyl)amino]methyl}-2-biphenylyl)acetic acid [abbreviated as compound (c) hereafter],] were 0.78 µM, 1.5 µM and 0.19 µM respectively.

EXAMPLE 2

Proliferating Effect of Human Prostate Stroma Cells Depending on LPA

Proliferating activity by LPA was measured using normal human prostate stroma cells (PrSC 5685; Clonetics) by making uptaking activity of deoxybromouridine (BrdU) into index.

To an MEM-α medium containing 10% FBS (fetal bovine serum), gentamicin (50 µg/ml), amphortercin B (50 ng/mL) and human bFGF and human insulin)(GIBCO Inc.) was added PrSC 5685 in a concentration of 1×10$^4$ cells/well in a 96-well plate and the mixture was cultured for 24 hours. Afterwards, it was washed with Hanks solution twice and the medium was exchanged with a serum-free medium (MEM-α containing gentamicin (50 µg/ml) and amphotercin B (50 ng/ml)) and cultured for another 24 hours. Thereto was added LPA (final concentration: 1 nM-10 µM) and at the same time was added BrdU and the mixture was cultured for 24 hours. The same amount of physiological saline was added in place of LPA as a control.

Uptaking of BrdU was measured by using cell proliferation ELISA kit (Amersham Inc.). Specifically, the cells were treated with BrdU and the cultured serum was discarded and to each well was added a cell anchorage/DNA denaturation solution (150 µl) and the mixture was allowed to stand for 30 minutes. The cell anchorage/DNA denaturation solution was removed and to the mixture was added Blocking buffer (150 µl) and the mixture was allowed to stand for another 30 minutes. Next the Blocking buffer was removed and thereto was added anti-BrdU antibody solution (100 µL) labeled with peroxidase and the mixture was allowed to stand for 30 minutes. Next the antibody solution was removed and the mixture was washed with Wash buffer (PBS(−); 150 µl) three times, moisture was removed enough by tapping and thereto was added a solution of a reaction substance (3,3',5,5',-tetramethylbenzidine, TMB 15% solution in DMSO; 100 µL). Thereto was added 2N solution of sulfuric acid (25 µL) and the absorbance was measured at 450 nm by microplate reader SPECTRAMAXPRO. The results are shown in FIG. 1.

EXAMPLE 3

Inhibitory Effect of Proliferating Effect of Human Prostate Stroma Cells Depending on LPA by an EDG-2 Antagonist Human-prostate stroma cells were cultured by the method described in example 2, just before adding LPA the test compound (final concentration: 1 nM to 10 µM) were added. The compound (a), compound (b) and compound (c) were used as the test compound. LPA was used in a concentration of 1 µM. After adding LPA was added BrdU and it was cultured for another 24 hours and the uptaking activity of BrdU was measured.

Figure 2:
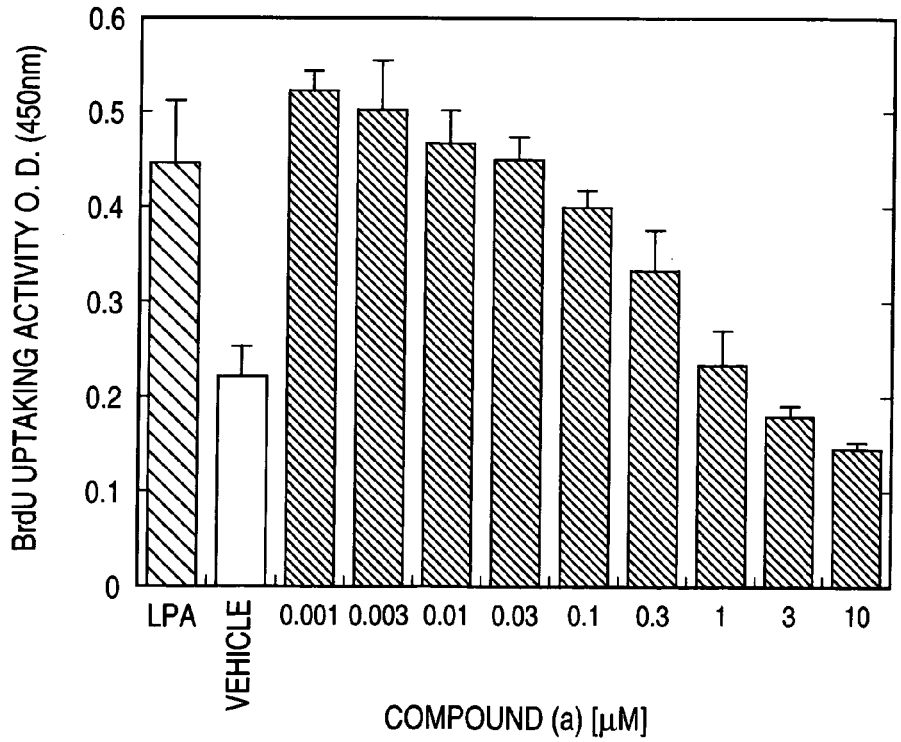
FIG. 2 shows that 3-(N-((2-(2-((pyridin-3-ylmethylamino)carbonyl)phenyl)phenyl)carbonyl)-N-(2-(2,5-dimethoxyphenyl)ethyl)amino)propanoic acid hydrochloride (compound (a)) suppresses the proliferation effect of normal human prostate stroma cells by LPA, depending on the concentration.
Figure 3:
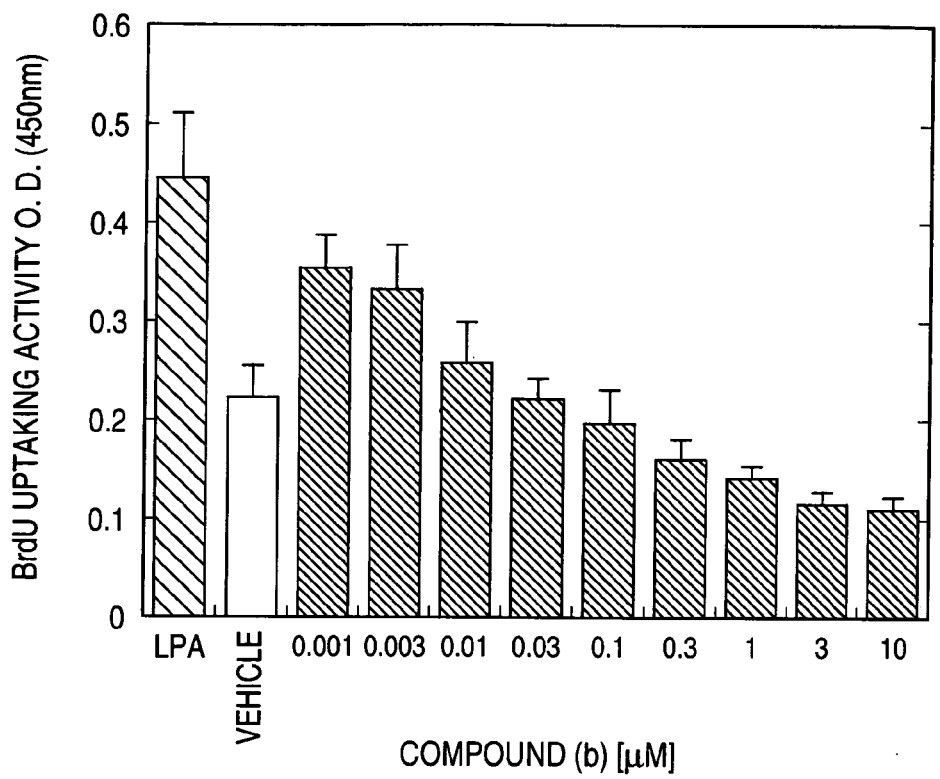
FIG. 3 shows that methyl 3-({4-[4-({[1-(2-chlorophenyl)ethoxy]carbonyl}amino)-3-methyl-5-isoquinazolyl]benzyl}sulfanyl)propanoate (compound (b)) suppresses the proliferation effect of normal human prostate stroma cells by LPA, depending on the concentration.
Figure 4:
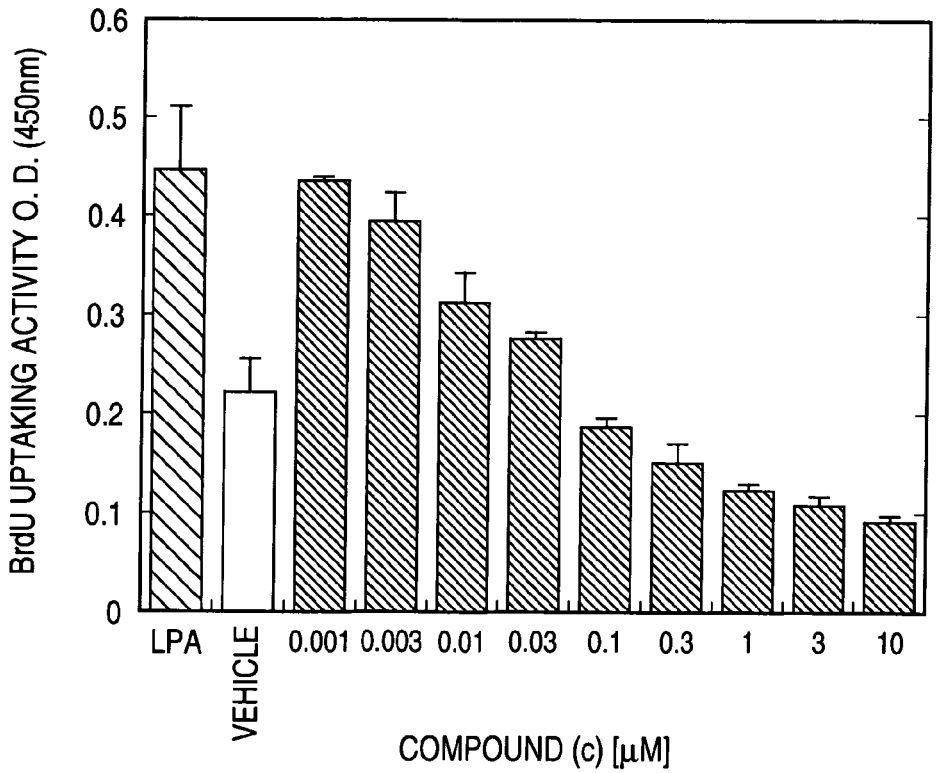
FIG. 4 shows that (4'-{[(3-phenylpropyl)(3,4,5-trimethoxybenzoyl)amino]methyl}-2-biphenylyl)acetic acid (compound (c)) suppresses the proliferation effect of normal human prostate stroma cells by LPA, depending on the concentration.

As a result, as shown in FIG. 2, FIG. 3 and FIG. 4, the test compound inhibited the proliferation of human prostate stroma cells by the LPA stimulation depending on the concentration.

Next, the cytotoxicity was evaluated measuring free LDH (Lactate dehydrogenase) in the supernatant of the medium. As a result, no cytotoxicity nonspecific to the test compound was observed, therefore it was found that the test compound inhibited the cell proliferation by antagonizing LPA.

From the results shown above, LPA promoted the proliferation of human prostate stroma cells and it was found the receptor in its charge was EDG-2.

EXAMPLE 4

Proliferating Effect of Human Airway Smooth Muscle Cells Depending on LPA

Proliferating activity of human airway smooth muscle cells by LPA was measured by BrdU uptaking activity of the cells (BSMC; Bio Whittaker Inc.).

BSMC was sowed to an MEM-α medium (GIBCO) containing 10% FBS (fetal bovine serum), gentamicin (50 μg/ml), amfortercin B (50 ng/ml), human bFGF and human insulin in a concentration of $1 \times 10^4$ cells/well in a 96-well plate and the mixture was cultured for 24 hours. Afterwards, it was washed with Hanks solution twice, and the medium was exchanged with a serum-free medium (an MEM-α containing gentamicin (50 μg/ml) and amphortecin B (50 ng/ml)) and the mixture was cultured for another 24 hours. Thereto was added LPA (final concentration: 3 nM-10 μM) and simultaneously was added BrdU and the mixture was cultured for another 6 hours. The same amount of physiological saline was added as a control in place of LPA.

Figure 5:
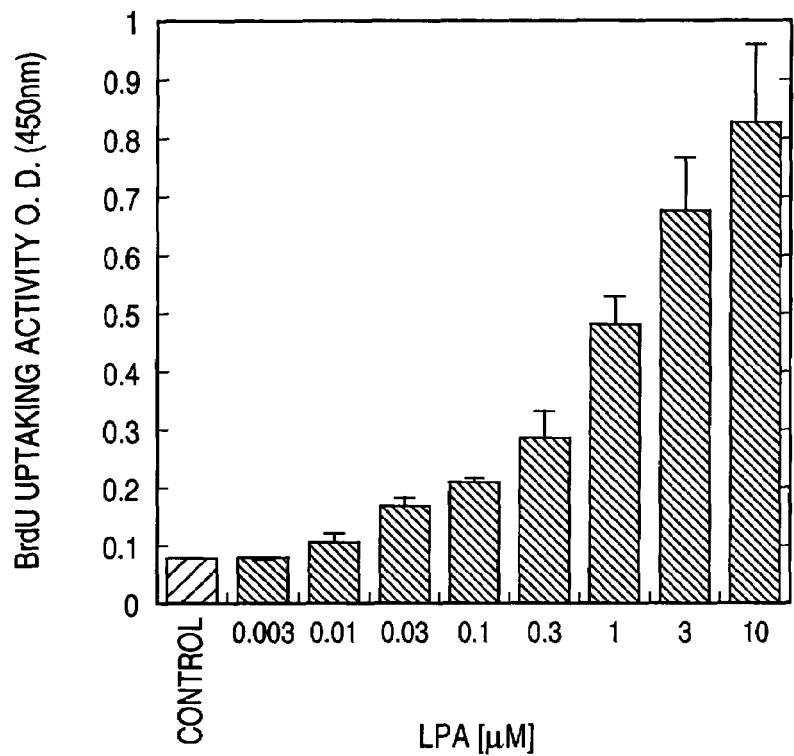
FIG. 5 shows the proliferation effect of normal human airway smooth muscle cells by LPA.

Uptaking of BrdU was measured by using cell proliferation ELISA kit (Amersham Inc.). Specifically, the cells were treated with BrdU and the cultured serum was discarded and to each well was added a cell anchorage/DNA denaturation solution (150 μl) and the mixture was allowed to stand for 30 minutes. The cell anchorage/DNA denaturation solution was removed and to the mixture was added a blocking buffer (150 μl) and the mixture was allowed to stand for another 30 minutes. Next the blocking buffer was removed and thereto was added anti-BrdU antibody solution (100 μL) labeled With peroxidase and the mixture was allowed to stand for 30 minutes. Next the antibody solution was removed and the mixture was washed with a wash buffer (PBS(-); 150 μl) three times, and the moisture was removed enough by tapping and then thereto was added a solution of a reaction substance (3,3',5,5',-tetramethylbenzidine, TMB 15% solution in DMSO; 100 μL). Thereto was added 2N solution of sulfuric acid (25 μL) and the absorbance was measured at 450 nm by microplate reader SPECTRAMAXPRO. The results are shown in FIG. 5.

EXAMPLE 5

Inhibition Effect of Proliferating Effect of Human Airway Smooth Muscle by an EDG-2 Antagonist Depending on LPA By the method shown in example 4 BSMC was cultured and the test compound (final concentration: 1 nM-10 μM) was added just before adding LPA. The above compound (a) and compound (b) were used as test compounds. LPA was used in a concentration of 3 μM. After adding LPA, BrdU was added and it was cultured for 6 hours and the uptaking activity of BrdU was measured.

Figure 6:
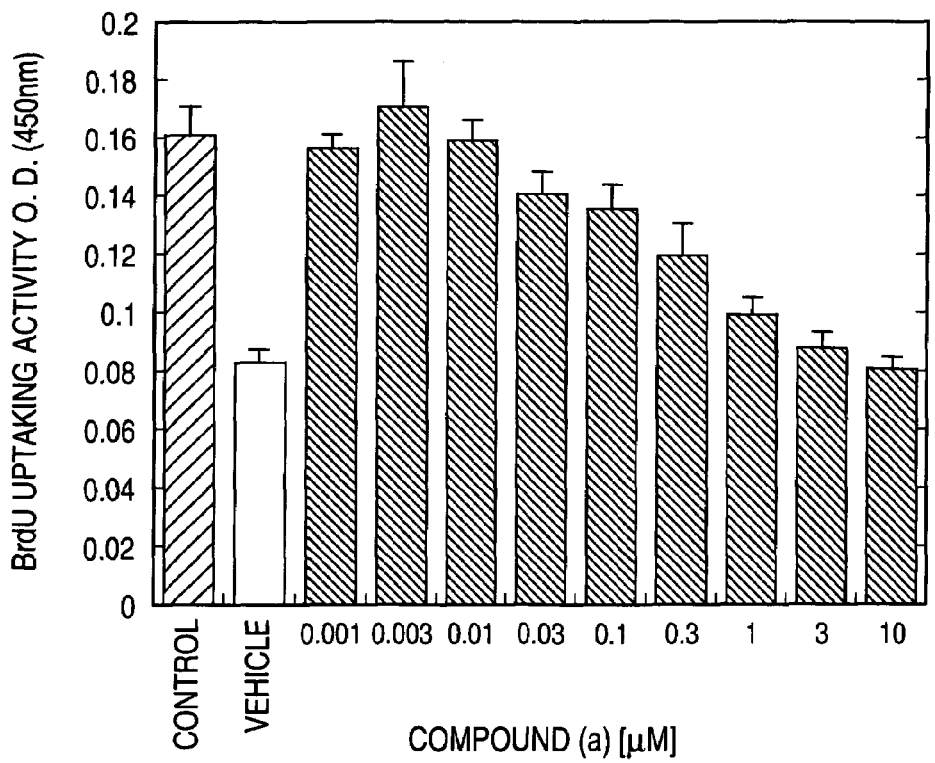
FIG. 6 shows that the compound (a) suppresses the proliferation effect of normal human airway smooth muscle cells by LPA, depending on the concentration.
Figure 7:
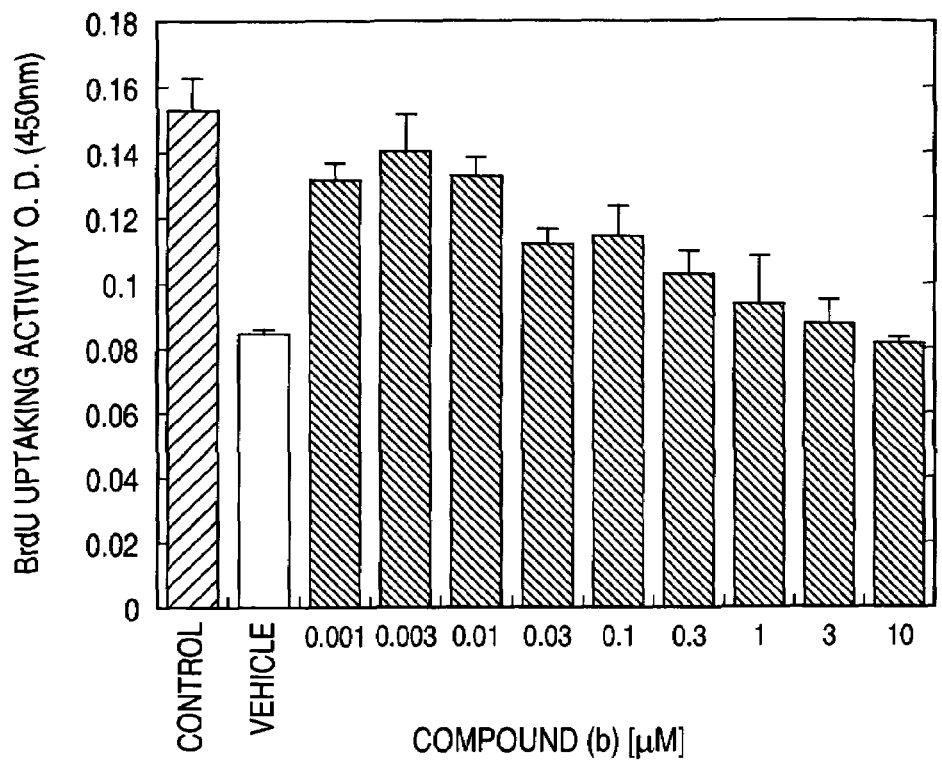
FIG. 7 shows that the compound (b) inhibits the proliferation effect of normal human airway smooth muscle cells induced by LPA depending on the concentration.

As a result, as shown in FIG. 6 and FIG. 7, it was found that the test compounds inhibited the proliferation of human airway smooth muscle cells by LPA stimulation depending on the concentration.

From the above results, it was found that LPA promotes the proliferation of human airway smooth muscle cells and that the receptor in its charge is EDG-2.

EXAMPLE 6

Proliferation Effect of Human Artery Smooth Muscle Depending on LPA

Figure 8:
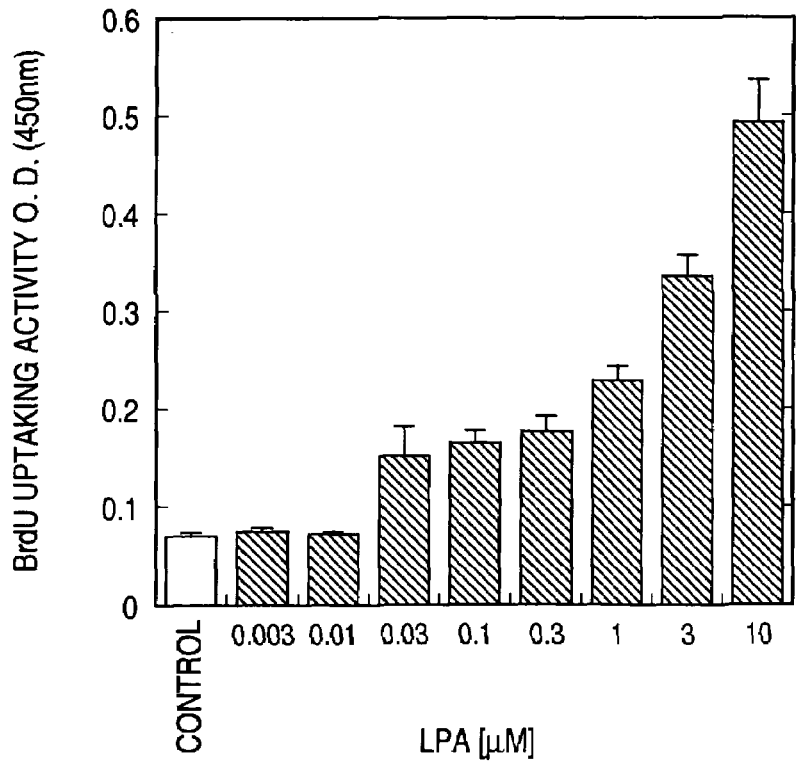
FIG. 8 shows the proliferation effect of normal human coronary artery smooth muscle cells induced by LPA.

Proliferating activity of human artery smooth muscle cells by LPA was measured by BrdU uptaking activity of the cells (CASMC Clonetics; lot #1F1808). In a medium (MEM-α/ FBS (50 μg/ml); gentamicin (50 ng/mL); amphotericin B) the cells were suspended and the suspension was sowed in a concentration of $1 \times 10^4$ cells/well in a 96-well plate and in 24 hours it was washed with Hanks solution (150 μL) twice and the medium was exchanged with serum-free medium (MEM-α (50 μg/mL); gentamicin (50 ng/mL); amphotericin B) in a volume of 100 μL/well and it was cultured for 24 hours. Thereto was added LPA in a final concentration of 0.03 μM-10 μM and 18 hours later was added BrdU and 24 hours later the uptaking of BrdU was measured. The results are shown in FIG. 8.

EXAMPLE 7

Inhibitory Effect of Proliferation of Mouse Precursor Fat Cells Depending on LPA by an EDG-2 Antagonist Proliferating activity of mouse precursor fat cells by LPA was measured by BrdU uptaking activity of the cells (3T3-L1). In a medium containing serum (DMEM/10% FBS (50 μg/mL); gentamicin (50 ng/mL); amphotericin B) the cells were suspended and the suspension was sowed in a concentration of $1 \times 10^4$ cells/well in a 96-well plate and it was cultured for 24 hours, and then it was washed with Hanks solution (150 μL) twice and the medium was exchanged with serum-free medium (DMEM (50 μg/mL); gentamicin (50 ng/mL); amphotericin B) and it was cultured for another 24 hours. Thereto was added the compound (b) or compound (c) in a final concentration of 0.001 μM-10 μM and 20 hours later thereto was added BrdU and 24 hours later, the uptaking of BrdU was measured.

Figure 9:
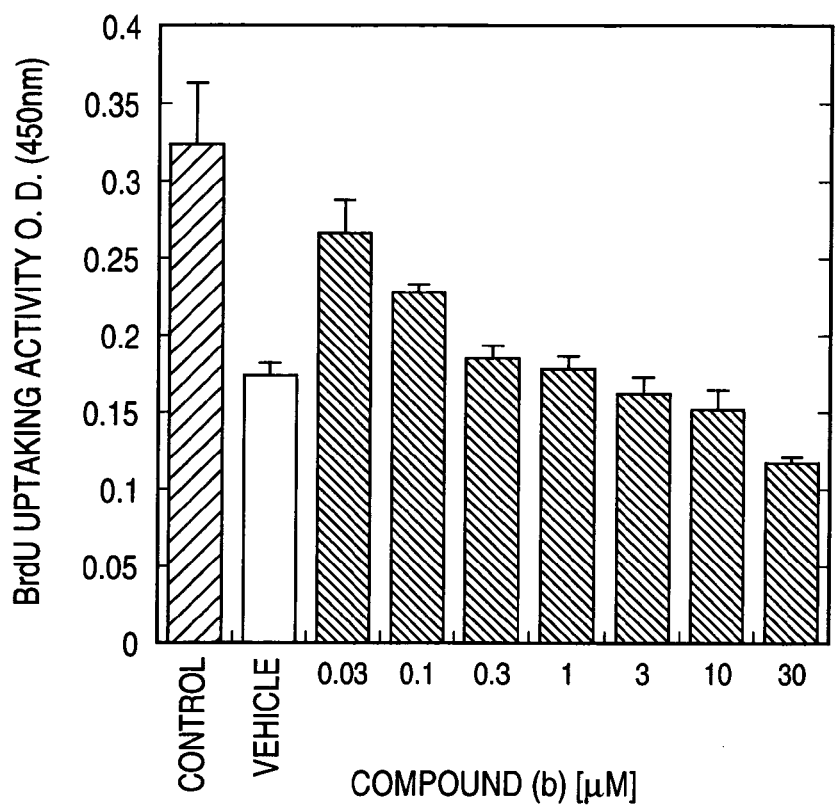
FIG. 9 shows that the compound (b) inhibits the proliferation effect of normal human precursor fat cells induced by LPA depending on the concentration.
Figure 10:
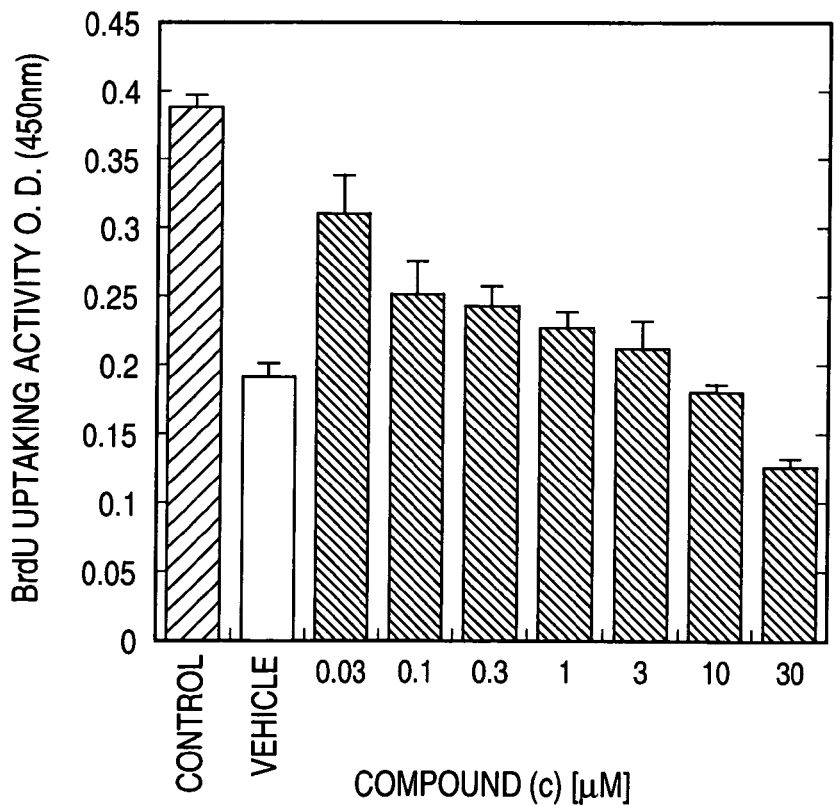
FIG. 10 shows that the compound (c) inhibits the proliferation effect of normal human precursor fat cells induced by LPA depending on the concentration.

As a result, as shown in FIG. 9 and FIG. 10, the compound (b) and compound (c) inhibited the proliferation of mouse precursor fat cells by LPA stimulation depending on the concentration.

EXAMPLE 8

Inhibitory Effect of Proliferation of Human Synovial Cells Depending on LPA by EDG-2 Antagonist Proliferating activity of human synovial cells by LPA was measured by BrdU uptaking activity of the cells (HFLS CELL APPLICATION Inc.). In a medium containing serum (Synoviocyte Basal Medium/Synoviocyte Growth Supplement) the cells were suspended and they were sowed in a collagen-coated 96-well plate in a concentration of $1 \times 10^4$ cells/well and 24 hours after it was washed with Hanks solution (150 μl) twice and the medium was exchanged with serum-free medium (Synoviocyte Basal Medium) in a volume of 100 μL/well and it was cultured for 24 hours. The compound (b) or compound (c) (each in a concentration of 0.001 μM-10 μM) was simultaneously added with LPA (in a concentration of 3 μM) and 18 hours after, thereto was added BrdU and the uptaking of BrdU was measured.

Figure 11:
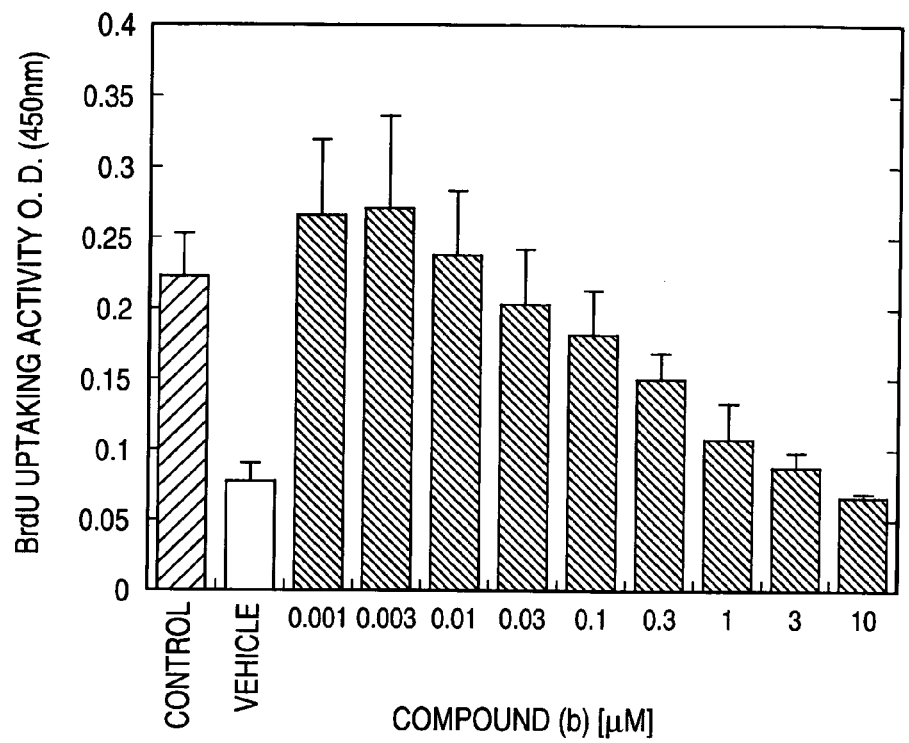
FIG. 11 shows that the compound (b) inhibits the proliferation effect of normal human precursor fat cells depending on the concentration.
Figure 12:
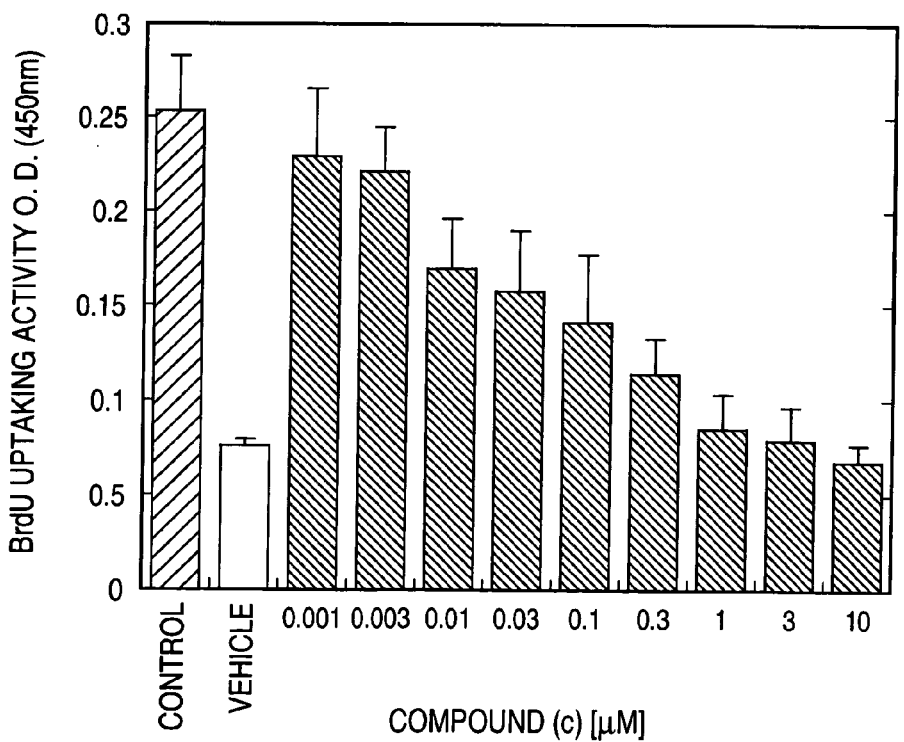
FIG. 12 shows that the compound (c) inhibits the proliferation effect of normal human synovial membrane depending on the concentration.

As a result, as shown in FIG. 11 and FIG. 12, the compounds (a) and (b) inhibited the proliferation of human synovial cells by stimulation of LPA.

FORMULATION EXAMPLE 1

The following components were admixed in a conventional manner and punched out to give 100 tablets each containing 50 mg of active ingredient.

| | |
|---|---|
| 3-(N-((2-(2-((pyridin-3-ylmethylamino)carbonyl)phenyl)-phenyl)carbonyl)-N-(2-(2,5-dimethoxyphenyl)ethyl)amino)-propanoic acid | 5.0 g |
| carboxymethylcellulose calcium (disintegrating agent) | 0.2 g |
| magnesium stearate (lubricating agent) | 0.1 g |
| microcrystalline cellulose | 4.7 g |

FORMULATION EXAMPLE 2

The following components were admixed in a conventional manner, and the solution was sterilized in a conventional manner, placed at 5 ml into ampoules and freeze-dried in a conventional method to thereby obtain 100 ampoules each containing 20 mg of the active ingredient.

| | |
|---|---|
| 3-(N-((2-(2-((pyridin-3-ylmethylamino)carbonyl)phenyl)-phenyl)carbonyl)-N-(2-(2,5-dimethoxyphenyl)ethyl)amino)-propanoic acid | 2.0 g |
| mannitol | 20 g |
| distilled water | 1000 ml |

The invention claimed is:

1. A pharmaceutical composition comprising an EDG-2 antagonist in combination with one or more selected from LPA receptor antagonist, anti-androgenergic agent, α1 receptor blocker or 5α-reductase inhibitor,
   wherein the EDG-2 antagonist is a β-alanine derivative of formula (I)

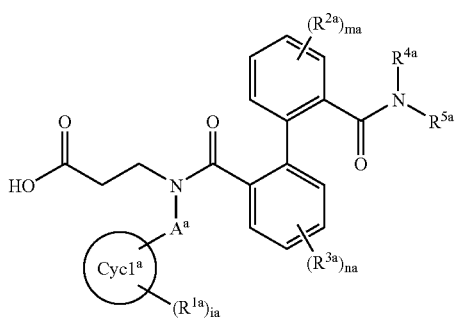

wherein $A^a$ is, (1) C1-6 alkeylene, (2) C2-6 alkenylene, or (3) C2-6 alkynylene, wherein $A^a$ may be substituted with 1-3 of C1-4 alkyl,
   $Cyc1^a$ is, (1) C3-15 carboring, or (2) 3-15 membered heteroring having 1-4 of nitrogen, 1-2 of oxygen and/or 1-2 of sulfur,
   $R^{1a}$ is (1) C1-4 alkyl, (2) halogen, (3) cyano, (4) trihalomethyl, (5) —$OR^{6a}$, (6) —$SR^7$, (7) —$NR^{8a}R^{9a}$, (8) nitro, (9) —$COOR^{10a}$, (10) —$CONR^{11a}R^{12a}$, (11) —$NR^{13a}COR^{14a}$, (12) —$SO_2NR^{15a}R^{16a}$, (13) —$NR^{17a}SO_2R^{18a}$, (14) —$S(O)R^{19a}$, or (15) —$SO_2R^{20a}$,
   $R^{6a}$, $R^{7a}$, $R^{8a}$, $R^{9a}$, $R^{10a}$, $R^{11a}$, $R^{12a}$, $R^{13a}$, $R^{14a}$, $R^{15a}$, $R^{16a}$, $R^{17a}$, $R^{18a}$, $R^{19a}$ and $R^{20a}$ are each independently, (1) hydrogen, or (2) C1-4 alkyl,
   $R^{2a}$ and $R^{3a}$ are each independently, (1) C1-4 alkyl, (2) C1-4 alkoxy, or (3) halogen,
   $R^{4a}$ and $R^{5a}$ are each independently, (1) hydrogen, (2) C1-4 alkyl, (3) C2-4 alkenyl, (4) C2-4 alkynyl, (5) C1-4 alkyl substituted with —$OR^{21a}$, (6) C1-4 alkyl substitute with —$NR^{22a}R^{23a}$ or

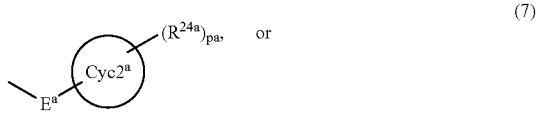

(7)

$R^{4a}$ and $R^{5a}$ are taken together with the nitrogen to which they are attached to form a 3-15 membered mono-, bi- or tri-cyclic heteroring, wherein the heteroring represents at least one nitrogen and it may be substituted with C1-4 alkyl substituted with —$OR^{25a}$,
   $R^{21a}$, $R^{22a}$, $R^{23a}$ and $R^{25a}$ are each independently, (1) hydrogen, (2) C1-4 alkyl, (3) C2-6 acyl, or (4) trihaloacetyl,
   $E^a$ is (1) a bond, (2) C1-6 alkylene, (3) C2-6 alkenylene, or (4) C2-6 alkynylene, wherein $E^a$ may be substituted with 1-3 of (1) C1-4 alkyl, or (2) C1-4 alkyl substituted with —$OR^{26a}$,
   $R^{26a}$ is (1) hydrogen, (2) C1-4 alkyl, (3) C2-6 acyl, or (4) trihaloacetyl, $Cyc2^a$ is (1) C3-15 carboring, or (2) 3-15 metered heteroring having 1-4 of nitrogen, 1-2 of oxygen and/or 1-2 of sulfur,
   $R^{24a}$ is (1) C1-4 alkyl, (2) halogen, (3) cyano, (4) trihalomethyl, (5) —$OR^{27a}$, (6) —$SR^{28a}$, (7) —$NR^{29a}R^{30a}$, (8) nitro, (9) —$COOR^{31a}$, (10) —$CONR^{32a}R^{33a}$, (11) —$NR^{34a}COR^{35a}$, (12) —$SO_2NR^{36a}R^{37a}$, (13) —$NR^{38a}SO_2R^{39a}$, (14) —$S(O)_2R^{40a}$, or (15) —$SO_2R^{41a}$,
   $R^{27a}$, $R^{28a}$, $R^{29a}$, $R^{30a}$, $R^{31a}$, $R^{32a}$, $R^{33a}$, $R^{34a}$, $R^{35a}$, $R^{36a}$, $R^{37a}$, $R^{38a}$, $R^{39a}$, $R^{40a}$ and $R^{41a}$ are each independently (1) hydrogen, or (2) C1-4 alkyl,
   ia is 0 or an integer of 1 to 5, ma is 0 or an integer of 1 to 4, and
   na is 0 or an integer of 1 to 4, pa is 0 or an integer of 1 to 5, and
   wherein when ia is 2 or more, $R^{1a}$'s are the same or different,
   when ma is 2 or more, $R^{2a}$'s are the same or different,
   when na is 2 or more, $R^{3a}$'s are the same or different, and
   when pa is 2 or more, they are the same or different, or a prodrug thereof or a salt thereof.

2. The pharmaceutical composition according to claim 1, wherein the pharmaceutical composition is effective for treatment of a chronic disease selected from the group consisting of chronic asthma, glomerular nephritis, obesity, prostate hyperplasia, a disease induced by the progress of arteriosclerosis, and rheumatoid or atopic dermatitis.

3. The pharmaceutical composition according to claim 2, wherein the composition is effective for the treatment of prostate hyperplasia.

4. A method for the treatment of a chronic disease selected from the group consisting of chronic asthma, glomerular nephritis, obesity, prostate hyperplasia, a disease induced by the progress of arteriosclerosis, and rheumatoid or atopic dermatitis, wherein said method comprises administering to a mammal having said chronic disease an effective amount of an EDG-2 antagonist, wherein the EDG-2 antagonist is a β-alanine derivative of formula (I)

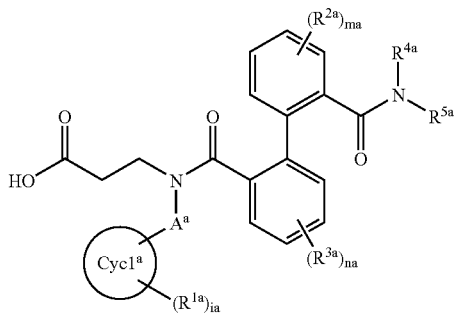

wherein $A^a$ is, (1) C1-6 alkylene, (2) C2-6 alkenylene, or (3) C2-6 alkynylene, wherein $A^a$ may be substituted with 1-3 of C1-4 alkyl, $Cyc1^a$ is, (1) C3-15 carboring, or (2) 3-15 membered heteroring having 1-4 of nitrogen, 1-2 of oxygen and/or 1-2 of sulfur, $R^{1a}$ is (1) C1-4 alkyl, (2) halogen, (3) cyano, (4) trihalomethyl, (5) —$OR^{6a}$, (6) —$SR^{7a}$, (7) —$NR^{8a}R^{9a}$, (8) nitro, (9) —$COOR^{10a}$, (10) —$CONR^{11a}R^{12a}$, (11) —$NR^{13a}COR^{14a}$, (12) —$SO_2NR^{15a}R^{16a}$, (13) —$NR^{17a}SO_2R^{18a}$, (14) —$S(O)R^{19a}$, or (15) —$SO_2R^{20a}$, $R^{6a}, R^{7a}, R^{8a}, R^{9a}, R^{10a}, R^{11a}, R^{12a}, R^{13a}, R^{14a}, R^{15a}R^{16a}, R^{17a}, R^{18a}, R^{19a}$ and $R^{20a}$ are each independently, (1) hydrogen, or (2) C1-4 alkyl, $R^{2a}$ and $R^{3a}$ are each independently, (1) C1-4 alkyl, (2) C1-4 alkoxy, or (3) halogen, $R^{4a}$ and $R^{5a}$ are each independently, (1) hydrogen, (2) C1-4 alkyl, (3) C2-4 alkenyl, (4) C2-4 alkynyl, (5) C1-4 alkyl substituted with —$OR^{21a}$, (6) C1-4 alkyl substituted with —$NR^{22a}R^{23a}$ or

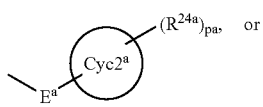  (7)

$R^{4a}$ and $R^{5a}$ are taken together with the nitrogen to which they are attached to form a 3-15 membered mono-, bi- or tri-cyclic heteroring, wherein the heteroring represents at least one nitrogen and it may be substituted with C1-4alkyl substituted with —$OR^{25a}$, $R^{21a}, R^{22a}, R^{23a}$ and $R^{25a}$ are each independently, (1) hydrogen, (2) C1-4 alkyl, (3) C2-6 acyl, or (4) trihaloacetyl, $E^a$ is (1) a bond, (2) C1-6 alkylene, (3) C2-6 alkenylene, or (4) C2-6 alkynylene, wherein $E^a$ may be substituted with 1-3 of (1) C1-4 alkyl, or (2) C1-4 A alkyl substituted with —$OR^{26a}$, $R^{26a}$ is (1) hydrogen, (2) C1-4 alkyl, (3) C2-6 acyl, or (4) trihaloacetyl, $Cyc2^a$ is (1) C3-15 carboring, or (2) 3-15 membered heteroring having 1-4 of nitrogen, 1-2 of oxygen and/or 1-2 of sulfur, $R^{24a}$ is (1) C1-4 alkyl, (2) halogen, (3) cyano, (4) trihalomethyl, (5)—$OR^{27a}$, (6) —$SR^{28a}$, (7) —$NR^{29a}R^{30a}$, (8) nitro, (9) —$COOR^{31a}$, (10) —$CONR^{32a}R^{33a}$, (11) —$NR^{34a}COR^{35a}$, (12) —$SO_2NR^{36a}R^{37a}$, (13) —$NR^{38a}SO_2R^{39a}$, (14) —$S(O)R^{40a}$, or (15) —$SO_2R^{41a}$, $R^{27a}, R^{28a}, R^{29a}, R^{30a}, R^{31a}, R^{32a}, R^{33a}, R^{34a}, R^{35a}, R^{36a}, R^{37a}, R^{38a}, R^{39a}, R^{40a}$, and $R^{41a}$ are each independently (1) hydrogen, or (2) C1-4 alkyl, ia is 0 or an integer of 1 to 5, ma is 0 or an integer of 1 to 4, and na is 0 or an integer of 1 to 4, pa is 0 or an integer of 1 to 5, and wherein when ia is 2 or more, $R^{1a}$'s are the same or different, when ma is 2 or more, $R^{2a}$'s are the same or different, when na is 2 or more, $R^{3a}$'s are the same or different, and when pa is 2 or more, they are the same or different, or a prodrug thereof or a salt thereof.

5. The method according to claim 4, wherein the chronic disease is prostate hyperplasia.

6. The method according to claim 4, wherein the method comprises administering to said mammal one or more members selected from the group consisting of an LPA receptor antagonist, an anti-androgenergic agent, an β1 receptor blocker, and an 5β-reductase inhibitor, in combination with the EDG-2 antagonist.

* * * * *